United States Patent
Gertler et al.

(10) Patent No.: US 10,443,054 B2
(45) Date of Patent: Oct. 15, 2019

(54) METHODS FOR IDENTIFYING AND TREATING INVASIVE/METASTATIC BREAST CANCERS

(71) Applicants: Massachusetts Institute of Technology, Cambridge, MA (US); King's College London, London (GB)

(72) Inventors: Frank B. Gertler, Boston, MA (US); Guillaume Carmona, Boston, MA (US); Matthias Krause, London (GB); Upamali Perera, London (GB)

(73) Assignees: MASSACHUSETTS INSTITUTE OF TECHNOLOGY, Cambridge, MA (US); KING'S COLLEGE LONDON, London, England (GB)

( * ) Notice: Subject to any disclaimer, the term of this patent is extended or adjusted under 35 U.S.C. 154(b) by 0 days.

(21) Appl. No.: 15/451,374

(22) Filed: Mar. 6, 2017

(65) Prior Publication Data
US 2017/0269093 A1   Sep. 21, 2017

Related U.S. Application Data
(60) Provisional application No. 62/304,243, filed on Mar. 6, 2016.

(51) Int. Cl.
*C12N 15/113* (2010.01)
*C12Q 1/6886* (2018.01)
*G01N 33/574* (2006.01)
*G01N 30/88* (2006.01)

(52) U.S. Cl.
CPC ......... *C12N 15/113* (2013.01); *C12Q 1/6886* (2013.01); *G01N 33/57484* (2013.01); *C12N 2310/14* (2013.01); *C12N 2310/315* (2013.01); *C12N 2310/531* (2013.01); *C12Q 2600/112* (2013.01); *C12Q 2600/118* (2013.01); *C12Q 2600/158* (2013.01); *G01N 2030/8813* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,530,101 A | 6/1996 | Queen et al. | |
| 5,585,089 A | 12/1996 | Queen et al. | |
| 5,693,761 A | 12/1997 | Queen et al. | |
| 5,693,762 A | 12/1997 | Queen et al. | |
| 5,807,715 A | 9/1998 | Morrison et al. | |
| 5,866,692 A | 2/1999 | Shitara et al. | |
| 5,876,949 A | 3/1999 | Dreyfuss et al. | |
| 5,939,598 A | 8/1999 | Kucherlapati et al. | |
| 5,997,867 A | 12/1999 | Waldmann et al. | |
| 6,054,297 A | 4/2000 | Carter et al. | |
| 6,075,181 A | 6/2000 | Kucherlapati et al. | |
| 6,114,598 A | 9/2000 | Kucherlapati et al. | |
| 6,150,584 A | 11/2000 | Kucherlapati et al. | |
| 6,162,963 A | 12/2000 | Kucherlapati et al. | |
| 6,180,370 B1 | 1/2001 | Queen et al. | |
| 6,180,377 B1 | 1/2001 | Morgan et al. | |
| 6,210,671 B1 | 4/2001 | Co | |
| 6,331,415 B1 | 12/2001 | Cabilly et al. | |
| 6,350,861 B1 | 2/2002 | Co et al. | |
| 6,982,321 B2 | 1/2006 | Winter | |
| 7,087,409 B2 | 8/2006 | Barbas, III et al. | |
| 7,192,698 B1 | 3/2007 | Kinch et al. | |
| 2012/0165390 A1 | 6/2012 | Sahin et al. | |

FOREIGN PATENT DOCUMENTS

| | | |
|---|---|---|
| EP | 0519596 | 4/2006 |
| WO | WO 1999/058572 | 11/1999 |
| WO | WO 2001/027160 | 4/2001 |
| WO | WO 2002/043478 | 6/2002 |
| WO | PCT/US2008/000310 | 7/2008 |

OTHER PUBLICATIONS

Chou et al. Optimization of probe length and the number of probes per gene for optimal microarray analysis of gene expression. Nucl. Acid Res. 32, e99, 2004 (Year: 2004).*
Amado, R. G. and I. S. Chen. 1999. Science 285:674-676.
Arjonen A, Kaukonen R, Mattila E, Rouhi P, Hognas G, Sihto H et al. Mutant P53-Associated Myosin-X Upregulation Promotes Breast Cancer Invasion and Metastasis. Jclin Invest 2014; 124: 1069-1082.
Bailly M. Macaluso F, Cammer M. Chan A. Segall Je. Condeelis Js. Relationship Between Arp2/3 Complex and the Barbed Ends of Actin Filaments at the Leading Edge of Carcinoma Cells After Epidermal Growth Factor Stimulation. Jcell Biol 1999: 145: 331-345.
Barry Dj, Durkin Ch, Abella Jv, Way M. Open Source Software for Quantification of Cell Migration, Protrusions, and Fluorescence Intensities. Jcell Biol 2015.
Barzik M, Kotovati, Higgs Hn, Hazelwood L, Hanein D, Gertler Fbetal. Enajvasp Proteins Enhance Actin Polymerization in the Presence of Barbed End Capping Proteins. Jbiol Chem 2005; 280: 28653-28662.
Bear Je, Loureiro Jj, Libova I, Fassler R, Wehland J, Gertler Fb. Negative Regulation of Fibroblast Motility by Enanasp Proteins. Cell 2000; 101: 717-728.

(Continued)

*Primary Examiner* — Elly-Gerald Stoica
(74) *Attorney, Agent, or Firm* — Bryan D. Zerhusen, Esq.; Cantor Colburn LLP

(57) ABSTRACT

Cancer invasion is a hallmark of metastasis. The mesenchymal mode of cancer cell invasion is mediated by elongated membrane protrusions driven by the assembly of branched F-actin networks. Described herein are compositions and methods for assessing and treating a subject having metastatic cancer or at risk of developing metastatic cancer, e.g., metastatic breast cancer, through the determination of Lamellipodin protein or gene expression levels in the subject.

11 Claims, 47 Drawing Sheets
Specification includes a Sequence Listing.

(56) References Cited

OTHER PUBLICATIONS

Bear Je, Svitkina Tm, Krause M, Schafer Da, Loureiro Jj, Strasser Gaet Al. Antagonism Between Enajvasp Proteins and Actin Filament Capping Regulates Fibroblast Motility. Cell 2002; 109: 509-521.
Beaty Bt. Condeelis J. Digging A Linle Deeper: The Stages of Invadopodium Formation and Maturation. Eur Jcell Biol 2014.
Bisi S, Disanza A, Malinverno C, Frinoli E, Palamidessi A, Scita G. Membrane and Actin Dynamics Interplay at Lamellipodia Leading Edge. Curr Opin Cell Bi0l 2013; 25: 565-573.
Boerner et al., J. Immunol., 147(1):86-95 (1991).
Bradley Wd, Koleske Aj. Regulation of Cell Migration and Morphogenesis by Abl-Family Kinases: Emerging Mechanisms and Physiological Contexts. J Cell Sci 2009; 122: 3441-3454.
Breitsprecher D, Kieseweher Ak, Linkner J, Urbanke C, Resch Gp, Small Jv et al. Clustering of Vasp Actively Drives Processive, Wh2 Domain-Mediated Actin Filament Elongation. Embo J 2008; 27: 2943-2954.
Breitsprecher O, Kiesewener Ak, Linkner J, Vinzenz M, Stradal Te, Small Jv et al. Molecular Mechanism of Enaivasp-Mediated Actin-Filament Elongation. Embo J 2011; 30: 456-467.
Brown et al. Cancer Res. 47: 3577-3583 (1987).
Chen et al., 1992, Nucleic Acids Res., 20, 4581 9.
Chereau D, Dominguez R. Understanding the Role of the G-Actin-Binding Domain of Ena/Vaspin Actin Assembly. Jstruct Biol 2006; 155: 195-201.
Chothia and Lesk, J. Mol. Biol. 196:901-917 (1987).
Cole et al., Monoclonal Antibodies and Cancer Therapy, Alan R. Liss, p. 77 (1985).
Daugherty et al., Nucl. Acids Rcs. 19: 2471-2476 (1991).
Derivery E. Lombard B, Loew D, Gautreau A. The Wave Complex Is Intrinsically Inactive. Cell Motil Cytoskeleton 2009; 66: 777-790.
Di Modugno F Mottolese M, Di Benedetto A, C0nidi A, Novelli F, Perracchio Letal. The Cytoskeleton Regulatory Protein Hmena (Enah) Is Overexpressed in Human Benign Breast Lesions With High Risk of Transformation and Human Epidermal Growth Factor Receptor-2-Positive/Hormonal Receptor-Negative Tumors. Clin Cancer Res 2006: 12:1470-1478.
Dickins Ra, Hemann Mi, Zilfou It, Simpson Dr. )Barra I, Hannon Gietal. Probing Tumor Phenotypes Using Stable and Regulated Synthetic Microrna Precursors. Nat Genet 2005; 37: 1289-1295.
Dropulic et al., 1992, J. Virol., 66, 1432 41.
Eccles Sa, Aboagye Eo, All 5, Anderson As, Armes J, Berditchevski Fet Al. Critical Research Gaps and Translational Priorities for the Successful Prevention and Treatment of Breast Cancer. Breast Cancer. Res 2013; 15: R92.
Elroy-Stein and Moss, 1990, Proc. Natl. Acad. Sci. USA, 87, 6743 7.
Friedl P, Alexander S. Cancer Invasion and the Microenvironment: Plasticity and Reciprocity. Cell 2011; 147: 992-1009.
Gao and Huang 1993, Nucleic Acids Res., 21, 2867 72.
Gligorijevic B, Wyckoff J, Yamaguchi H, Wang Y, R0uss0s Et, Condeelis J. N-Wasp-Mediated Invadopodium Formation is Involved in Intravasation and Lung Metastasis of Mammary Tumors. Jcell Sci 2012; 125: 724-734.
Good et al., 1997, Gene Therapy, 4, 45.
Goswami S. Sahai E. Wyckoff Jb. Cammer M. Cox D, Pixley Ed et al. Macrophages Promote the Invasion of Breast Carcinoma Cells via a Colony-Stimulating Factor-I /Epidermal Growth Factor Paracrine Loop. Cancer Res 2005; 65: 5278-5283.
Greuber Ek, Smith-Pearson P, Wang J, Pendergast Am. Role of Abl Family Kinases in Cancer: From Leukaemia to Solid Tumours. Nat Rev Cancer 2013:13:559-571.
Grimm, D. et al. 2007. Am. Soc. Hematol. Educ. Program 473-481.
Hamers-Casterman et al., Nature 363:446¬448 (1993).
Hannon, G. J. et al. 2004. Methods Mol. Biol. 257:255-266.
Hansen Sd, Mullins Rd. Vasp Is a Processive Actin Polymerase That Requires Monomeric Actin for Barbed End Association. J Cell Biol 2010; 191: 571-584.
Harris, Biochem. Soc. Transactions 23:1035-1038 (1995).

Heid, C, et al.; TaqMan PCR, Genome Res., 6 (10), 986 (1996), ABI PRISM.TM. Sequence Detection System, Applied Biosystems.
Hennigan Re, Hawker Kl, Ozanne Bw. Fos-Transformaton Activates Genes Associated With Invasion. Oncogene 1994; 9:3591-3600.
Hoogenboom and Winter, J. Mol. Biol., 227:381 (1991).
Hurle and Gross, Curr. Op. Biotech. 5:428-433 (1994).
Iglesias Pa. Devreotes Pn. Navigating Through Models of Chemotaxis. Curr Opin Cell Biol 2008; 20: 35-40.
Ignatoski Km. Ethier Sp. Constitutive Activation of Pp125fak in Newly Isolated Human Breast Cancer Cell Lines. Breast Cancer Res Treat 1999; 54:173-182.
Insall Rh, Machesky Lm. Actin Dynamics at the Leading Edge: From Simple Machinery to Complex Networks. Dev Cell 2009; 17: 310-322.
Izant and Weintraub, 1985, Science, 229, 345.
Janetopoulos C, Firtel Ra. Directional Sensing During Chemotaxis. Febs Len 2008; 582: 2075-2085.
Johnson and Wu, in Methods in Molecular Biology 248:1-25 (Lo, ed., Human Press, Totowa, N.J., 2003).
Jones et al., Nature 321:522-525 (1986).
Kashani-Sabet et al., 1992, Antisense Res. Dev., 2, 3 15.
Kim Lc, Song L, Haura Es. Src Kinases as Therapeutic Targets for Cancer. Nat Rev Clin Oncol 2009; 6: 587-595.
Koleske Aj, Gifford Am, Scott Ml, Nee M, Bronson Rt, Miczek Kaet Al. Essential Roles for the Abl and Arg Tyrosine Kinases in Neurulation. Neuron 1998; 21:1259-1272.
Krause M, Leslie Ud, Stewart M, Lafuente Em. Valderrama F, Jagannathan R et al. Lamellipodin, An Enajvasp Ligand, Is Implicated in the Regulation of Lamellipodial Dynamics. Dry Cell 2004; 7: 571-583.
Krause M, Sautreau A. Steering Cell Migration: Lamellipodium Dynamics and the Regulation of Directional Persistence. Nature Reviews. Molecular Cell Biology 2014; 15: 577-590.
Krause M. Dent Ew. Bear Je, Loureiro Ii. Gertler Fr. Enanasp Proteins: Regulators of the Actin Cytoskeleton and Cell Migration. Annu Revcell Devbiol 2003: 19: 541-564.
Lamar Jm, Stern P, Liu H, Schindler Jw, Jiang Zg, Hynes Ro. The Hippo Pathway Target, Yap, Promotes Metastasis Through Its Tead-Interaction Domain. Proc Natl Acad Sd U S A 2012; 109: E2441-2450.
Law Al, Vehlow A, Kotini M, Dodgson L. Soong D. Theveneau E et al. Lamellipodin and the Scar/Wave Complex Cooperate to Promote Cell Migration In Vivo. Jcell Biol 2013; 203: 673-689.
Lebrand C. Dent Ew, Strasser Ga, Lanier Lm, Krause M, Svitkina Tmetal. Critical Role of Enarjasp Proteins for Filopodia Formation in Neurons and in Function Downstream of Netrin-1. Neuron 2004; 42: 37-49.
Lee Si, Rouhi P, Dahl Jensen U, Zhang D, Ji H, Hauptmann Cetal. Hypoxia-Induced Pathological Angiogenesis Mediates Tumor Cell Dissemination, Invasion, and Metastasis in a Zebrafish Tumor Model. Proc Natl Acad Sci Usa 2009; 106: 19465-19490.
L'Huillier et al., 1992, EMBO J., 11, 4411 8.
Li et al., Proc. Natl. Acad. Sci. USA, 103:3557-3562 (2006).
Lieber et al., 1993, Methods Enzymol., 217, 47 66.
Lisziewicz et al., 1993, Proc. Natl. Acad. Sci. U.S.A, 90, 8000 4.
Lobuglio et al. Proc. Nat. Acad. Sci. USA 86: 4220-4224 (1989).
Loi S., Haibe-Kains B, Desmedt C, Wirapati P, Lallemand F, Tutt Am et al. Predicting Prognosis Using Molecular Profiling in Estrogen Receptor-Positive Breast Cancer Treated With Tamoxifen. Bmc Genomics 2006: 9:239.
Lu P. Weaver Vm, Were 1 the Extracellular Matrix: A Dynamic Niche in Cancer Progression. Jcell Biol 2012; 196: 395-406.
Lyulcheva E, Taylor E, Michael M, Vehlow A, Tan 5, Fletcher A et al. *Drosophila pico* and Its Mammalian Ortholog Lamellipodin Activate Serum Response Factor and Promote Cell Proliferation. Dev Cell 2008; 15: 680-690.
Magdalene, M., Vehlow, A., Navarro C., Krause M. C-Abl, Lamellipodin, and Ennvasp Proteins Cooperate in Dorsal Ruffling of Fibroblasts and Axonal Morphogenesis. Curr Bi0l 2010; 20: 783-791.
Marks et al., J. Mol. Biol., 222:581 (1991).
McGarry and Lindquist, 1986, Proc. Natl. Acad. Sci., USA 83, 399.

(56) References Cited

OTHER PUBLICATIONS

Miller Ld, Smeds J. George J, Vega Vb. Vergara L. Ploner A et al. An Expression Signature for P53 Status in Human Breast Cancer Predictsmutation Status, Transcriptional Effects, and Patient Survival. Proc Natl Acadsciusa2005; 102:13550-13555.

Minn Aj. Gupta Gp, Siegel Pm. B0s Pd. Shu W. Girl Dd et al. Genes That Mediate Breast Cancer Metastasis to Lung. Nature 2005; 436: 516-524.

Mouneimne G, Soon L, Desmarais V, Sidani M, Song X, Yip Sc et al. Phospholipase C and Cofilin are Required for Carcinoma Cell Directionality in Response to Egfstimulation. Jcell Bi0l 2004; 166: 697-708.

Mouneimne G. Desmarais V, Sidani M, Scemes E, Wang W, Song X et al. Spatial and Temporal Control of Cofilin Activity is Required for Directional Sensing During Chemotaxis. Curr Bi0l 2006; 16: 2193-2205.

Newsome Tp. Weisswange I, Frischknecht F, Way M. Abl Collaborates With Src Family Kinases to Stimulate Actin-Based Motility of Vaccinia Virus. Cell Micr0biol 2006; 8: 233-241.

Nishikura, K. 2001. Cell 107:415-418).

Ojwang et al., 1992, Proc. Natl. Acad. Sci. USA, 89, 10802 6.

Pasic L, Kotova T, Schafer Da. Enanaspproteins Capture Actin Filament Barbed Ends. Jbi0l Chem 2008; 283: 9814-9819.

Philippar U, Roussos Et, Oser M, Yamaguchi H, Kim Hd, Giampieri Setal. A Mena Invasion Isoform Potentiates Egf-Induced Carcinoma Cell Invasion and Metastasis. Dev Cell 2008; 15: 813-828.

Poincloux R, Lizarraga F. Chavrier P. Matrix Invasion by Tumour Cells: A Focus on Mt1-Mmp Trafficking to Invadopodia. Jcell Sci 2009: 122: 3015-3024.

Presta, Curr. Op. Struct. Biol. 2:593-596 (1992).

Rhodes Dr, Yu J, Shanker K, Deshpande N, Varambally R, Ghosh D Etal. Oncomine: A Cancer Microarray Database and Integrateo Data-Mining Platform. Ne0plasia2004;6: 1-6.

Ridley Aj. Life at the Leading Edge. Cell 2011; 145: 1012-1022.

Riechmann et al., Nature 332:323-329 (1988).

Roussos Et, Balsamo M, Alford 5k, Wyckoff Jb, Gligorijevic B, Wang Y Er Al. Mena Invasive (Menainv) Promotes Multicellular Streaming Motility and Transendothelial Migration in a Mouse Model of Breast Cancer. Jcell Sd 2011; 124: 2120-2131.

Roussos Et, Condeelis Js, Patsialou A. Chemotaxis in Cancer. Nat Rev Cancer 2011; 11: 573-587.

Roussos Et, Wang N', Wyckoff Is. Sellers Rs. Wang W. Li J Etal. Mena Deficiency Delays Tumor Progression and Decreases Metastasis in Polyoma Middle-T Transgenic Mouse Mammary Tumors. Breast Cancer Res 2010; 12:R101.

Sanz-Moreno V. Gadea G, Ahn J, Paterson H. Marra P, Pinner Setal. Rac Activation and Inactivation Control Plasticity of Tumor Cell Movement. Cell 2008: 135: 510-523.

Sarver et al., 1990 Science, 247, 1222 1225.

Scanlon et al., 1991, Proc. Natl. Acad. Sci. USA, 88, 10591-5.

Sharma Vp. Eddy R, Entenberg D, Kai M, Gertler Fb, Condeelis J. Tks5 and Ship2 Regulate Invadopodium Maturation, but Not Initiation, in Breast Carcinoma Cells. Curr Biol 2013; 23:2079-2089.

Shaw et al. J. Immunol. 138: 4534-4538 (1987).

Sheriff et al., Nature Struct. Biol. 3:733-736 (1996).

Sikorski, R. et al. 1998. Science 282:1438.

Sullenger & Cech, 1993, Science, 262, 1566).

Symons Mh, Mitchi50n Tj. Control of Actin Polymerization in Live and Permeabilized Fibroblasts. Jcell Biol 1991; 114: 503-513.

Thompson et al., 1995, Nucleic Acids Res., 23, 2259.

Tomizuka et al. (2000) Proc. Natl. Acad. Sci. USA 97:722-727.

Van De Vijver Mj, He 'I'd, Vant Veer U, Dai H, Hartaa, Voskuil Dwetal. A Gene-Expression Signature as a Predictor of Survival in Breast Cancer. N Engl J Med 2002; 347: 1999-2009.

Van Dijk and Van de Winkel, Curr. Opin. Pharmacol., 5: 368-74 (2001).

Vaswani and Hamilton, Ann. Allergy, Asthma & Immunol. 1:105-115 (1998).

Vehlow A. Soong D, Vizcay-Barrena G, B0d0 C. Law Al, Perera U et al. Endophilin. Lamellipodin. And Mena Cooperate to Regulate F-Actin Dependent Egf-Receptor Endocytosis. Embo J 2013: 32: 2722-2734.

Verhoeyen et al. Science 239: 1534-1536 (1988).

Weerasinghe et al., 1991, J. Virol., 65, 5531 4.

Winter et al. Nature 349: 293-299 (1991).

Xu et al., Immunity 13:37-45 (2000).

Youssef G, Gille1j C, Agbaje 0, Crompton T, Montano X. Phosphorylation of Ntrk1 at Y674/Y675 Induced by Tps3-Dependent Repression of Ptpn6 Expression: A Potential Novel Prognostic Marker for Breast Cancer. Mod Pathol 2014; 27: 361-374.

Yu et al., 1993, Proc. Natl. Acad. Sci. USA, 90, 6340 4.

Zhou et al., 1990, Mol. Cell. Biol., 10, 4529 37.

Mena Accession No. AY345143 https://www.ncbi.nlm.nih.gov/nuccore/AY345143 Title—"Human Mena: cDNA cloning, expression and promoter characterization".

Lpd Accession No. AY494951 https://www.ncbi.nlm.nih.gov/nuccore/AY494951 Title—"Lamellipodin, an Ena/VASP ligand, is implicated in the regulation" of lamellipodial dynamics.

\* cited by examiner

FIGURE 1E

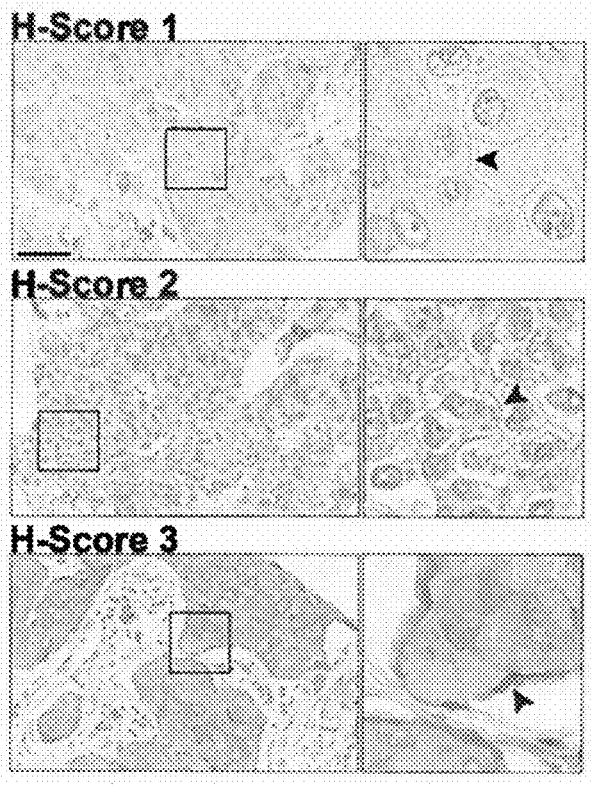

FIGURE 1F

| Tumor type and comparison tissue | Fold change | p value | Reference |
|---|---|---|---|
| Ductal Breast Carcinoma in Situ vs. Normal | 2.844 | 0.022 | Radvanyi |
| Invasive Breast Carcinoma Stroma vs. Normal | 5.256 | 1.60E-10 | Finak |
| Invasive Ductal Breast Carcinoma vs. Normal | 1.53 | 3.20E-15 | TCGA |
| Invasive Breast Carcinoma vs. Normal | 1.469 | 4.29E-09 | TCGA |
| Mucinous Breast Carcinoma vs. Normal | 1.74 | 0.02 | TCGA |
| Mixed Lobular and Ductal Breast Carcinoma vs. Normal | 1.373 | 0.006 | TCGA |
| Invasive Lobular Breast Carcinoma vs. Normal | 1.301 | 2.85E-04 | TCGA |
| Invasive Ductal Breast Carcinoma Epithelia vs. Normal | 1.229 | 0.036 | Ma |

| Group | Mice with visible lung metastases |
|---|---|
| Ctrl-shRNA | 9/10 |
| Lpd-shRNA1 | 1/9 |
| Lpd-shRNA2 | 2/11 |

FIGURE 2M

Clinical and pathological features of 312 primary breast carcinoma samples.

| | | |
|---|---|---|
| Total Number | 312 | |
| Clinical Tumor Size[a] (cm) | | |
| Range | 0.4 – 7.5 | |
| Mean | 2.53 | |
| <2 | 42 | 15% |
| 2-5 | 225 | 80% |
| >5 | 13 | 5% |
| Histological Tumor Type | | |
| Ductal NOS[b] | 257 | 82% |
| Lobular | 37 | 12% |
| Pure Special Type | 14 | 5% |
| Mixed/Other | 4 | 1% |
| Histological Grade | | |
| Grade I | 52 | 17% |
| Grade II | 122 | 39% |
| Grade III | 113 | 36% |
| Unknown | 25 | 8% |
| Positive Axillary Lymph Nodes[c] | | |
| 0 | 131 | 45% |
| 1-3 | 97 | 33% |
| 4+ | 63 | 22% |
| Biomarkers[d] | | |
| ER | 223 | 73% |
| PR | 187 | 61% |
| HER2 | 248 | 79% |
| Survival Status | | |
| Alive | 152 | |
| Died – Breast Cancer Cause | 92 | |
| Died – Other Causes | 68 | |

[a] clinical size available for 280 cases.
[b] DuctalNOS = Ductal not otherwise specified.
[c] Nodal status available for 291 cases.
[d] Biomarker available for 306 cases.

FIGURE 7A

| | c-Src | c-Abl |
|---|---|---|
| Y67 MANFSYKFSIYN | | (-) |
| Y72 YKFSIYNLNEAL | | (-) |
| Y151 PSKASYSLDDVT | | (-) |
| Y308 KSHCGYSLDWSL | | (-) |
| Y357 ERIEKYALFKNP | | (+) |
| Y366 KNPQSYLLGKKE | | (+) |
| Y417 SWKKRYFLIAAS | | (-) |
| Y426 RASGIYYVPKGE | | (+++) |
| Y451 DHVNVYYGQDYR | | (-) |
| Y456 YYGQDYRNKYKA | | (++) |
| Y460 DYRNKYKAPTDY | | (+) |
| Y466 KAPTDYCLVLKE | | (+) |
| Y481 QKKSQYIKYLCC | | (+) |
| Y484 SQYIKYLCCDDV | | (-) |
| Y505 IRIAKYGKQLYN | | (+) |
| Y510 YGKQLYNFYQEA | | (+) |
| Y513 QLYNFYQEALKR | | (+++) |
| Y524 RTESAYDQTSLS | | (-) |
| Y602 SMNRFYTSIVPP | | (-) |
| Y619 KIVTFYTASQPS | | (-) |
| Y667 PMFVKYSTIRL | | (+) |
| Y823 AFRASYIPPSPP | | (-) |
| Y1218 QQKAGYGGSSIS | | (-) |
| Y1226 SHISCYATLRRG | | (++) |

METHODS FOR IDENTIFYING AND TREATING INVASIVE/METASTATIC BREAST CANCERS

CROSS-REFERENCE TO RELATED APPLICATION

Under 35 U.S.C. § 119(e) this application claims the benefit of U.S. Provisional Patent Application No. 62/304,243 filed 6 Mar. 2016, which is hereby incorporated by reference in its entirety for all purposes.

INCORPORATION BY REFERENCE

In compliance with 37 C.F.R. § 1.52(e)(5), the sequence information contained in electronic file name: 1515028.104US2_Sequence_Listing_ST25.txt; size 25.6 KB; created on: 24 May 2017; using Patent-In 3.5, and Checker 4.4.0 is hereby incorporated herein by reference in its entirety.

STATEMENT REGARDING FEDERALLY FUNDED RESEARCH

This invention was made with government support under grant no.: U54-CA112967 awarded by National Institutes of Health. The government has certain rights in the invention.

BACKGROUND

1. Field of the Discovery

Presently described are methods for the identification and treatment of invasive and/or metastatic cancers, e.g., breast cancer. In particular, the description provides methods of diagnosing a metastatic cancer, e.g., metastatic breast cancer, or assessing the risk of developing the same by detecting the amount of Lamellipodin (Lpd) protein or Lpd gene expression or both in a subject.

2. Background Information

Cancer cell invasion is a hallmark of metastasis, and remains a significant health problem and complicate the decisions regarding therapy for cancer sufferers. In particular, breast cancer metastasis is one of the leading causes of cancer-associated mortality in women worldwide. Metastatic breast cancer is also classified as Stage 4 breast cancer that spreads to lungs, liver, bones or other parts of the body. Cancer cell metastasis requires modulation of protein regulators of cellular mobility, including actin filaments and associated cytoskeletal regulators. The mesenchymal mode of cancer cell invasion is mediated by elongated membrane protrusions driven by the assembly of branched F-actin networks. How deregulation of actin regulators promotes cancer cell invasion is still enigmatic.

The lamellipodium is the protrusion of a cell enabling the cell to migrate and is driven by the polymerization of a cytoskeletal protein, actin, at the leading edge of the cell. It contains a three-dimensional actin mesh, which pushes the membrane forward. The protrusion of the lamellipodium is coupled to the attachment of the cell to the substratum directly behind the leading edge. Finally, the turnover of adhesions at the rear of the cell allows the cell to translocate. Thus, the lamellipodium is pivotal for efficient mesenchymal cell migration and it also acts as a steering device for cells in the process of chemotaxis.

Lamellipodin (Lpd) has been shown to be an important component of the lamellipodia and is essential for lamellipodia formation. Thus, Lpd is required for mesenchymal cell migration in two dimensions and neural crest migration in vivo. It localises to the very edge of lamellipodia and functions to recruit Ena/VASP proteins (Ena, Mena, VASP, EVL) to the leading edge of cell. Furthermore, Lpd binds to the Scar/WAVE complex, an actin nucleation promoting factor, which is mediates lamellipodium formation. As demonstrated herein, overexpression of Lpd in cancer cell lines in vitro increases cellular mobility in three dimensions via both Ena/VASP proteins and the Scar/WAVE complex. Lpd promotes metastasis by supporting tumor invasion and intravasation. Furthermore, Lpd appears to be involved in the regulation of cell proliferation. Moreover, two studies with limited patient numbers were not conclusive whether Lpd is overexpressed in breast cancer.

Lamellipodin (Lpd) or RAPH1 (Ras-associated and pleckstrin homology domains-containing protein 1) is required for lamellipodium formation. The lamellipodium is a cytoskeletal protein actin projection on the leading edge of the cell. It contains a quasi-two-dimensional actin mesh, which propels the cell across a substrate. The lamellipodium is born of actin nucleation in the plasma membrane of the cell and is the primary area of actin incorporation or microfilament formation of the cell. Lamellipodia are found primarily in very mobile cells, they are believed to be the actual motor which pulls the cell forward during the process of cell migration. It also acts as a steering device for cells in the process of chemotaxis.

Lpd has been shown to be an important component of the lamellipodia. For example, Lamellipodin (Lpd) helps regulate cell motility and recruits Ena/VASP proteins (Ena, Mena, VASP, EVL) to the leading edge of cell. Overexpression of Lpd in cancer cell lines in vitro has been demonstrated to increase cellular mobility. Conventional wisdom is that Lpd promotes metastasis by supporting tumor invasion and intravasation. However, experimental evidence suggests that Lpd expression does not affect tumor growth. Moreover, multiple studies have suggested that Lpd is not overexpressed in breast cancer.

Because of the crucial role that cellular mobility plays in cancer metastasis, especially breast cancer metastasis, it remains critical to develop assays capable of accurately diagnosing and predicting when cancer cells are or may be at risk of becoming metastatic. Despite the large number of published articles on breast cancer biomarkers, there is a great need for a reliable marker for use in routine clinical practice. Thus, an immediate need exists for the identification of biomarkers with the potential to enhance early diagnosis and to predict patient prognosis, drug resistance development and treatment choice because of high mortality rate due to metastasis.

SUMMARY

The present disclosure provides compositions and methods for improved diagnosis and treatment of metastatic cancer, e.g., metastatic breast cancer. In particular, presently described is a reliable biomarker for use in methods of diagnosing or prognosing metastatic cancer at early stage for improved survivability and better treatment.

As described herein, increased Lpd levels (i.e., amount of protein, gene expression or both) correlate with reduced metastasis-free survival and increased breast cancer associated death in breast cancer patients. As indicated above, Lpd is believed to promote metastasis by supporting tumor invasion and intravasation. Mechanistically, it is thought that Lpd functions as an essential component of a pro-metastatic signaling pathway, and can be used alone as a reliable marker for early diagnosis or prognosis of metastatic cancer.

As such, in certain aspects, the description provides methods for assessing, (i.e., diagnosing or prognosing) a metastatic cancer. In certain embodiments, the method comprises first obtaining a biological sample from a subject. In additional embodiments, the method involves determining the amount of Lamellipodin (Lpd) protein or Lpd gene expression level or both in the sample, e.g., by detecting the presence of Lpd and/or measuring the amount of Lpd. In further embodiments, the method involves correlating the amount of Lpd protein or gene expression level or both to the metastatic state or capacity of cells in the sample, wherein an enhanced amount of Lpd protein or upregulated gene expression of Lpd is indicative of a metastatic cancer or a cancer at risk of becoming metastatic.

In an additional aspect, the description provides methods for diagnosing or prognosing metastatic cancer in a subject comprising obtaining a biological sample from a subject; determining the amount of Lamellipodin (Lpd) protein or expression level or both in the sample; comparing the amount of Lpd protein or gene expression level or both in the sample with that of a control; and correlating the amount of Lpd protein or gene expression level or both to the metastatic state or capacity of cells in the sample, wherein an enhanced amount of Lpd protein or upregulated gene expression of Lpd relative to the control is indicative of a metastatic cancer or a cancer at risk of becoming metastatic.

In any of the aspects or embodiments described herein, the method may include a step of diagnosing the subject as having no metastatic cancer or having metastatic cancer or making a prognosis that the subject is at risk of developing metastatic cancer.

The description further provides methods for diagnosing or prognosing metastatic cancer in a subject, the method comprises obtaining a biological sample from a subject; detecting and/or measuring the amount of Lamellipodin (Lpd) protein with an Lpd-specific antibody or Lpd-binding polypeptide; determining the amount of Lamellipodin (Lpd) protein in the sample; and correlating the amount of Lpd protein to the metastatic state or capacity of cells in the sample, wherein an enhanced amount of Lpd protein is indicative of a metastatic cancer or a cancer at risk of becoming metastatic. In certain embodiments, the step of detecting the amount of Lpd protein comprises detecting the Lpd by Western blotting, dot blotting, precipitation, agglutination, ELISA assay, immunohistochemistry, immunocytochemistry, flow cytometry or FACS sorting, or the like.

In another aspect, the description provides methods for diagnosing or prognosing metastatic cancer in a subject. In an embodiment, the method includes obtaining a biological sample from a subject; detecting the level of Lamellipodin (Lpd) gene expression with a nucleic acid that hybridizes specifically to or is complementary to an Lpd encoding nucleic acid; determining the level of Lpd gene expression in the sample; and correlating the level of Lpd gene expression to the metastatic state or capacity of cells in the sample, wherein an enhanced level of Lpd gene expression is indicative of a metastatic cancer or a cancer at risk of becoming metastatic.

In an additional aspect, the description provides methods for diagnosing metastatic cancer in a subject. In certain embodiments, the method comprises obtaining a biological sample from a subject; extracting total RNA or protein or both from the sample; determining the amount of Lamellipodin (Lpd) protein or gene expression level or both in the sample by contacting the sample with at least one of i) a nucleic acid capable of hybridizing specifically to an Lpd-encoding nucleic acid; ii) an anti-Lpd antibody or Lpd-binding polypeptide capable of binding specifically to Lpd protein; and correlating the amount of Lpd protein or gene expression level or both to the metastatic state or capacity of cells in the sample, wherein an enhanced amount of Lpd protein or upregulated gene expression of Lpd is indicative of a metastatic cancer or a cancer at risk of becoming metastatic.

In certain embodiments, the detection and/or measuring of Lpd protein is performed by detecting the amount of binding of an anti-Lpd antibody to Lpd protein as mentioned above. In certain other embodiments, the detection and/or measuring of Lpd gene expression is performed by hybridizing a nucleic acid probe, e.g., labeled probe, to a nucleic acid that encodes a Lpd protein or portion thereof. In certain aspects, the nucleic acid is an Lpd-encoding mRNA or portion thereof. In certain aspects, the nucleic acid is an Lpd-encoding cDNA or portion thereof.

In any of the aspects or embodiments described herein, the method may further comprise the step of administering a therapeutic or therapeutic intervention (e.g., surgery) to the subject.

In another aspect, the description provides methods for diagnosing or prognosing metastatic cancer in a subject. In embodiments, the method comprises obtaining a biological sample from a subject; extracting total RNA or protein or both from the sample; determining the amount of Lamellipodin (Lpd) protein or expression level or both in the sample by contacting the sample with at least one of i) a nucleic acid capable of hybridizing specifically to an Lpd-encoding nucleic acid; ii) an anti-Lpd antibody or Lpd-binding polypeptide capable of binding specifically to Lpd protein; correlating the amount of Lpd protein or expression level or both to the metastatic state or capacity of cells in the sample, wherein an enhanced amount of Lpd protein or upregulated expression of Lpd is indicative of a metastatic cancer or a cancer at risk of becoming metastatic; and administering a therapeutic to a subject diagnosed as having metastatic cancer or at risk of developing metastatic cancer.

In any of the aspects or embodiments described herein, the biological sample can be a cellular or tissue sample. In certain embodiments, the cellular or tissue sample is at least one of breast tissue, breast cancer tissue, or metastatic breast cancer tissue.

It is presently observed that Abl-mediated Lamellipodin phosphorylation promotes its association with both Scar/WAVE and Ena/VASP, while Src-dependent phosphorylation enhances binding to SCAR/WAVE but not Ena/VASP. Increased Lamellipodin levels enhance Ena/VASP and Scar/WAVE activities at the plasma membrane to promote 3D invasion and metastasis. With this knowledge and understanding, the therapeutic agent can be a phosphorylation or a kinase inhibitor in various embodiments. In another embodiment, the therapeutic agent can be Abl and/or Src tyrosine kinase inhibitor.

In an embodiment, the therapeutic agent can be an inhibitor of Lpd wherein, the inhibitor of Lpd is an antibody, an antibody fragment, a small organic molecule of less than 2000 daltons, an siRNA or a shRNA.

In embodiments the therapeutic agent can be selected from cisplatin, cyclophosphamind, doxorubicin, prednisone, 5-FU, trastuzumab, docetaxel, 3G4, travacin, gemcitabine, phalloidin, cytochalasin D, latrunculin, jasplakinolide, swinholide, estramustine, carboplatin, prednisone, a HER2 or HER3 or HER2/3 antibody, trastuzumab, pertuzumab, neuvax, PI3K/AKT inhibitor, radioimmunotherapy agents or combinations thereof.

In certain embodiments, the therapeutic agent can be one or more of anti-immunomodulatory agent, anti-inflammatory agents, glucocorticoid, steroid, nonsteroidal anti-inflammatory drug, leukotreine antagonist, 13 2-agonist, anticholinergic agent, sulphasalazine, penicillamine, dapsone, antihistamines, anti-malarial agents, anti-viral agents, antibiotics or combinations thereof.

In another aspect, the description provides methods of treating a subject at risk of or having metastatic cancer comprising correlating the amount of Lpd protein or gene expression level or both in a biological sample from a subject to the metastatic state or capacity of cells in the sample, wherein an enhanced amount of Lpd protein or upregulated expression of Lpd relative to the control is indicative of a metastatic cancer or a cancer at risk of becoming metastatic; and administering a therapeutic course to a subject having metastatic cancer or being at risk of developing metastatic cancer.

In another aspect, the description provides methods of treating a subject at risk of or having metastatic cancer comprising obtaining a biological sample from a subject; determining the amount of Lamellipodin (Lpd) protein or expression level or both in the sample; comparing the amount of Lpd protein or expression level or both in the sample with that of a control; correlating the amount of Lpd protein or expression level or both to the metastatic state or capacity of cells in the sample, wherein an enhanced amount of Lpd protein or upregulated expression of Lpd relative to the control is indicative of a metastatic cancer or a cancer at risk of becoming metastatic; and administering a therapeutic course to a subject having metastatic cancer or being at risk of developing metastatic cancer.

In any of the above mentioned aspects or embodiments, wherein the method further comprises a step of detecting and measuring the amount of Mena protein or its isoforms or gene expression level, wherein enhanced amount of Mena protein or gene expression is indicative of a metastatic cancer or cancer at risk of becoming metastatic.

In certain embodiments the method detects and measures the amount of MenaINV protein or gene expression level, wherein enhanced amount of MenaINV protein or gene expression is indicative of a metastatic cancer or cancer at risk of becoming metastatic.

In some particular embodiments, the method utilizes therapeutic agents to disrupt Lpd and MenaINV interaction to prevent metastasis.

In certain additional embodiments, the therapeutic agent is a peptide.

In an additional aspect, the description provides diagnostic kits for determining metastatic tumors comprising a container and including the components and agents needed to detect and measure the presence and amount of Lpd protein or Lpd expression in a biological sample according to a method as described herein.

In any of the aspects or embodiments described herein, the biological sample is a cell or a tissue. In certain embodiments, the cell or tissue is a cancer cell or cancerous tissue. In still additional embodiments, the cancer cell or cancerous tissue is a breast cancer cell or breast cancer tissue. In certain embodiments, the cells can be obtained from blood, plasma, serum mucus or any body fluids.

In aspects or embodiments, the cancer is one or more of breast, prostate, lung, colorectal, colon, rectal, head and neck, mesothelioma, ovarian, urothelial, hepatocellular, bladder, esophageal, stomach or any cancer that has metastatic capability.

BRIEF DESCRIPTION OF THE DRAWINGS

The above and other features of the present invention will now be described in detail with reference to certain exemplary embodiments thereof illustrated the accompanying drawings which are given herein below by way of illustration only, and thus are not limitative of the present invention, and wherein:

FIG. 1A-1J: Increased Lpd expression correlates with poor prognosis for breast cancer patients. FIG. 1A: Western blot analysis of Lpd expression in human breast cancer cell lines with varying metastatic potential. Loading control: Tubulin. FIG. 1B: Kaplan-Meier analysis of metastasis-free survival in the NK1295 data set. Patients were stratified by expression of Lpd. The p value was calculated by a log rank test. FIG. 1C: Kaplan-Meier analysis of disease-free survival in the NK1295 data set. Patients were stratified by expression of Lpd. The p value was calculated by a log rank test. FIG. 1D: Kaplan Meier plots of breast cancer associated mortality of histoscore 1-3 for Lpd intensity at the plasma membrane. Histoscore 2: Hazard Ratio (HR) (95% CD: 2.23 (1.26-3.95). FIG. 1E: Representative examples of Lpd immunohistochemistry staining for histoscore 1-3 for Lpd staining intensity at the plasma membrane. Scale bar, 5 μm. FIG. 1F:) Lpd expression was examined in various microarray data sets that profiled one or more breast tumor subtypes against normal tissue by using oncomine database. FIG. 1G: Kaplan-Meier analysis of metastasis survival in the Loi. FIG. 1H: Kaplan-Meier analysis of metastasis survival in the Miller datasets. Patients were stratified by expression of Lpd. The P value was calculated by a log rank test. FIG. 1I: Kaplan Meier plots of breast cancer associated mortality of histoscore 1-3 for Lpd intensity in the cytoplasm. Histoscore 2: HR (95% CI): 1.765 (1.026-3.036). FIG. 1J: Table showing the association between HER2 status and the histoscore 1-3 for Lpd intensity at the membrane. Chi-square=6.7236; DF 2; P≤0.0347.

FIG. 2A-2P: Lpd is required for lung metastasis from orthotopic mammary tumors. FIG. 2A-2E: NOD/SCID/IL2Ry-null mice were injected orthotopically with LM2 cells stably expressing Ctrl-shRNA or Lpd-5hRNA1 or Lpd-5hRNA2. Tumors were allowed to grow for 6±0.5 weeks. FIG. 2A: Primary tumor weights at sacrifice of individual mice are shown. Data are represented as mean±s.e.m. FIG. 2B: The number of mice that presented with visible metastases in the lung is indicated (mice with lung metastases/total number of mice analyzed) FIG. 2C: Representative images of whole left pulmonary lobe from LM2 (control or knockdown)-tumor-bearing mice with ZsGreen-positive metastatic foci (top panel). Scale bar, 5 mm. Representative lung sections stained with H&E, arrowhead indicates presence of metastatic foci (bottom panel). Scale bar, 20 μm. FIG. 2D: Numbers of ZsGreen-positive metastatic foci in the left pulmonary lobe were counted. Quantification of data shown in (C, top panel). Data are represented as mean±s.e.m. One-way ANOVA; Dunnett's; * P≤0.05. FIG. 2E: Representative images of paraffin tissue sections stained with Masson's trichrome of primary tumors to show local invasion. Scale Bar, 20 μm. FIG. 2F: Image shows a CtrI-shRNA Zsgreen-tumor. Cyan=Zsgreen-positive cells, red=collagen fibers. One motile Ctrl-shRNA-expressing tumor cell is outlined.

Scale bar 40 μm. FIG. 2G: The average numbers of motile cells per field were determined. Data are represented as mean±s.e.m. Unpaired t-test; *p≤0.05, n=5 mice per group. FIG. 2H: The average numbers of cells extending protrusions per field were determined. Data are represented as mean±s.e.m; unpaired t-test; * P≤0.05; n=5 mice per group. FIG. 2I: Directionality of the motile cells (net path/total path) was determined. Data are represented as mean±s.e.m; unpaired t-test; * P 0.05; n=5 mice per group. FIG. 2J: Image of representative zebrafish trunks, two days after injection. Arrows point to seeded tumor cells. Scale bar, 500 μm. FIG. 2K: Quantified data from (J) represented as mean number of seeded tumor cells per mm of trunk length. mean±s.e.m, data from 53 fish embryos for GFP and 49 fish embryos for GFP-Lpd from 3 independent experiments; t-test; ** P≤0.01. FIG. 2L-2P: Analysis of Lpd expression in tumor microarrays. FIG. 2L: Representative examples of Lpd immunohistochemistry staining for histoscore 1-3 for Lpd intensity in the cytoplasm. Scale bar, 5 μm. FIG. 2M: Clinical and pathological features of the primary breast carcinoma samples. 312 patients analysed. FIG. 2N: shRNA-mediated stable knockdown of Lpd in LM2 cells was measured by Western blotting. FIG. 2O: LM2 cells stably expressing Ctrl-shRNA or Lpd-shRNA2 were injected via the tail vein and the formation of lung metastases was evaluated. Representative images of whole left pulmonary lobe from LM2 from mice injected with LM2 cells (Ctrl-shRNA or Lpd-shRNA2) with ZsGreen-positive metastatic foci (top panel). Scale bar, 5 mm. FIG. 2P: LM2 cells stably expressing Ctrl-shRNA or Lpd-shRNA2 were injected via the tail vein and the formation of lung metastases was evaluated. Representative images of whole left pulmonary lobe from LM2 from mice injected with LM2 cells (Ctrl-shRNA or Lpd-shRNA2) with ZsGreen-positive metastatic foci (top panel). Scale bar, 5 mm. LM2 cells stably expressing Ctrl-shRNA or Lpd-shRNA2 were injected via the tail vein and, after 28 days, the formation of lung metastases was evaluated. Numbers of ZsGreen-positive metastatic foci in the left pulmonary lobe were counted. Data are represented as mean±s.e.m. Number of animals per group: Ctrl-shRNA: 9 mice, Lpd-shRNA2: 9 mice. Unpaired t-test. The difference between ctrl-shRNA and Lpd-shRNA2 was not significant.

FIG. 3A: Representative kymographs of Ctrl-shRNA and Lpd-5hRNA2 MTLn3 cells. A line drawn perpendicular to the cell surface is shown for each frame of a time-lapse movie to depict temporal dynamics of cell edge. X-axis: time (arrow length: 20 seconds); Y-axis: distance (arrow length: 3.1 μm). FIG. 3B: Quantification of protrusion parameters from kymographic analysis of Ctrl-shRNA and Lpd-shRNA2 MTLn3 cells. Data represented as mean±s.e.m. Unpaired t-test; * P≤0.05. FIG. 3C: Micrographs showing immunofluorescence for endogenous Lpd in MTLn3 cells stimulated with 5 nM EGF (post-stimulation time is indicated). Scale bar, 10 μm. FIG. 3D: Quantification of data shown in 3C: mean fluorescence intensity of Lpd within a 0.66 μm zone at the lamellipodial edge is plotted as a function of time; >30 cells analyzed from at least three independent experiments. Error bars indicate s.em. FIG. 3E: Representative micrographs from time-lapse movies of Ctrl-shRNA (control non-targeting shRNA) and Lpd-5hRNA2 expressing MTLn3 cells stimulated with 5 nM EGF. Dashed line shows cell edge. Scale bar, 10 μm. FIG. 3F: Quantification of membrane protrusions on Ctrl-shRNA and Lpd-shRNA treated cells. Cell area was determined after EGF stimulation and normalized to the pre-treatment cell area; >30 cells analyzed from three independent experiments. Error bars indicate s.e.m. FIG. 3G-3K: Lpd is required EGF-induced membrane-protrusion. FIG. 3G: B16-F1, MDA-MB-231 and MTLn3 cell lines stably expressing Ctrl-shRNA or Lpd-shRNA were plated on collagen supplemented with fibronectin and fixed and stained with a p34 (Arp2/3) antibody. Quantification of the ratio of the length of lamellipodia to length of perimeter of cell. (n=3). Data are represented as mean±s.e.m. Unpaired t-test; * P≤0.05, **P≤0.0001, NS—not significant. FIG. 3H: Quantification of protrusion parameter from kymographic analysis of Ctrl-shRNA and Lpd-shRNA2 MDA-MB-231 cells stimulated with EGF. Data are represented as mean±s.e.m. Unpaired t-test; * P≤0.05, NS—not significant. FIG. 3I: shRNA-mediated stable knockdown of Lpd in MTLn3 cells was measured by Western blotting. FIG. 3J: Quantification of mean protrusion speed from kymographic analysis of Ctrl-shRNA and Lpd-shRNA2 MTLn3 cells stimulated with EGF. Data are represented as mean±s.e.m. Unpaired t-test; NS—not significant. FIG. 3K: Quantification of protrusion initiation after EGF stimulation in MDA-MB-231 cells stably expressing Ctrl-shRNA or Lpd-shRNA2. Data represented as mean±s.e.m. Unpaired t-test; * P≤5 0.05.

FIG. 4A: Barbed-end incorporation after 5 nM EGF stimulation in Ctrl-shRNA- and Lpd 5hRNA2-MTLn3 cells. Fixed cells expressing rhodamine-labeled actin were co-stained with phalloidin. Scale bar, 20 μm. FIG. 4B: Relative number of barbed-ends incorporation at the lamellipodium edge at 1 mm after 5 nM EGF stimulation; over 60 cells analyzed. (n=3). Data are represented as mean±s.e.m. Unpaired t-test; * p 0.05. FIG. 4C: Mena immunofluorescence in Ctrl-shRNA and Lpd-shRNA2 MTLn3 cells. Cells were stimulated for 1 mm with 5 nM EGF. Insets show enlarged image of Mena staining. Scale bar, 10 μm. FIG. 4D: Quantification of data shown in 4C; mean fluorescence intensity of Mena at the lamellipodium edge (within 0.66 μm of leading edge); over 45 cells analyzed. (n=3). Data are represented as mean±s.e.m. Unpaired t-test; * P≤0.05. FIG. 4E: p34Arc immunofluorescence in Ctrl-shRNA- and Lpd shRNA2-MTLn3 cells, 1 mm after 5 nM EGF stimulation. Insets show enlarged image of p34Arc staining. Scale bar, 10 μm. FIG. 4F: Quantification of data shown in 4E; mean fluorescence intensity of p34Arc at the lamellipodium edge (within 0.66 μm of the leading edge); over 45 cells analyzed. (n=3). Data are represented as mean±s.e.m. Unpaired t-test; * P 0.05. FIG. 4G: Representative micrographs from time-lapse movies of Ctrl-shRNA- and Lpd-shRNA2-MTLn3 cells stimulated with an EGF-filled micropipette (position indicated by asterisk). White arrows on the 480s frames indicate the directions of protrusion overtime. Scale bar, 10 μm. Colored lines indicate cell contour. FIG. 4H: Quantification of chemotactic index of Ctrl-shRNA- and Lpd shRNA2-MTLn3 cells. Over 25 cells analyzed from at least three independent experiments. Data are represented as mean±s.e.m. Unpaired t-test; * P≤S 0.05. FIG. 4I: Quantification of chemotactic index of Ctrl-shRNA MTLn3 cells transfected with GEP vector (n=13 cells); and Lpd-shRNA2-MTLn3 cells transfected with either GFP vector (n=22 cells), GFP-Lpd (n=17 cells) or GFPLpd$^{EVmut}$(n=17 cells). Data are represented as mean±s.e.m. One-way ANOVA; Bonferroni's test; * p≤0.05 vs Ctrl shRNA+GFP; ** P≤0.05 vs Lpd-shRNA2+GFP; P≤0.05 vs Lpd-shRNA2+GFP-Lpd.

The difference between Lpd-shRNA2+GFP and Lpd-shRNA2+GFPLpd$^{mut}$ was not significant. FIG. 4J-4K: Quantification of membrane protrusion at the front (FIG. 4J) and retraction (FIG. 4K) of Ctrl-shRNA and Lpd-shRNA2 MTLn3 cells versus time after adding EGF. Error bars indicate s.e.m. FIG. 4L: Immunofluorescence with anti-Lpd (green) and phalloidin (red) of MTLn3 cells stimulated for 1 min with an EGF-filled micropipette (indicated by asterisk). Scale bar, 10 μm.

FIG. 5A-5B: Inverted invasion assays were performed using MDA-MB-231 cells stably expressing mCherry-H2B (labeling the nucleus) transfected with Ctrl-shRNA, Lpd shRNA1, or Lpd-shRNA2. Additionally cells were co-transfected with empty Blasticidin vector as well and transfected cells were selected. The nuclei of the cells were visualized using confocal microscopy. FIG. 5A: The image stacks were processed by Volocity software to make a 3D reconstruction. FIG. 5B: Quantification of the number of nuclei of invading cells above 40 μm from the data shown in 5A. n=4 (with approximately 4000 cells per experiment). Data are represented as mean±s.e.m. One-way ANOVA; Dunnett's; * P≤0.05. FIG. 5C: Inverted invasion assays with GFP or GFP-Lpd expressing MDA-MB-231 cells treated with the MMP inhibitor 10 μm GM6001 or just the solvent DMSO as control. Quantification of the number of nuclei of invading cells above 40 μm from the data. n=3. Data are represented as mean±s.e.m. One-way ANOVA; Tukey's; * P≤0.05, P≤0.01 * P≤0.001. FIG. 5D: Inverted invasion assays were performed using MDA-MB-231 breast cancer cells stably expressing mCherry-H2B (labeling the nucleus) transfected with GFP-Lpd, GFP-Lpd$^{EVmut}$, GFPLpd$^{S/Wmut}$, GFPLpd$^{EVmut+S/Wmut}$ or GFP empty vector as control. The nuclei of the cells were visualized using confocal microscopy. The image stacks were processed by Volocity software to make a 3D reconstruction. FIG. 5E: Quantification of the number of nuclei of invading cells above 40 μm from the data shown in 5D. n=3 (with approximately 4000 cells per experiment). Data are represented as mean±s.e.m. One-way ANOVA: Dunnett's; * P≤0.05, P≤0.01 * P≤0.001. FIG. 5F: MDA-MB-231 plated on Alexa 488 gelatin/fibronectin matrix, fixed, and stained for Lpd. and the invadopodia marker cortactin. White boxes: enlarged images shown in insets. Scale bar: 10 μm. FIG. 5G: Steady-state assay for invadopodial matrix degradation. MDA-M8-231 cells were plated for 8 hours on Alexa 488-gelatin/fibronectin matrices, fixed and stained with phalloidin. Scale bar, 10 μm. FIG. 5H: Quantification of data shown in 5G: invadopodial degradation area/cells in the steady-state matrix degradation assay, normalized to number of cells/field. Data are represented as mean±s.e.m. (n=3). Mann-Whitney test; P≤0.05. FIG. 5I: MDA-MB-231 stably expressing Ctrl-shRNA or Lpd-shRNA cells were plated on 405-gelatin and immunostained with cortactin and Tks5 antibodies to identify invadopodia. Scale bar, 10 μm. FIG. 5J: Quantification of data shown in 5I; Number of total invadopodia, invadopodia precursors and mature invadopodia per cell were determined; Ctrl-shRNA cells (n=52) or Lpd-shRNA cells (n=57). Data are represented as mean±s.e.m. Mann-Whitney test; P≤0.05. (K-M): Lpd binding to ENa/VASP is required for chemo-sensing. FIG. 5K: Representative micrographs from time-lapse movies of AP4-mito and FP4-mito stably expressed in MTLn3 cells stimulated with an EGF-filled micropipette (asterisk indicates the position of the micropipette). The white arrows on the 480 sec frames indicate the resulting directions of protrusion overtime. Scale bar, 10 μm. Colored lines indicate the contour of the cell. FIG. 5L: Quantification of the chemotactic index of MTLn3 cells stably expressing AP4-mito or FP4-mito. Over 20 cells analyzed from at least three independent experiments. Data are represented as mean±s.e.m. Unpaired t-test; * P≤0.05. FIG. 5M: Representative micrographs from time-lapse movies of Ctrl-shRNA and Lpd-shRNA2 MTLn3 cells, and transfected with either GFP-vector or GFP-Lpd or GFP-LpdEV$^{mut}$ and stimulated with an EGF-filled micropipette (asterisk indicates the position of the micropipette). The white arrows on the 480 sec frames indicate the resulting directions of protrusion overtime. Scale bar, 10 μm. Colored lines indicate the contour of the cell.

FIG. 6A: HEK293FT cells were transfected with either GFP as control or GFP-Lpd and cotransfected with Src-WT (wild type) or Src-K1 (kinase inactive). Immunoprecipitation was performed from cell lysates using Lpd-specific antibodies or rabbit IgG as control followed by Western blotting with anti-Lpd and antiphosphotyrosine (pTyr) antibodies. n3. FIG. 6O: MDA-MB-231 cells stably expressing Ctrl-shRNA or Lpd-shRNA were plated for 4 hours on 405-gelatin, fixed and immunostained with Mena and Cortactin. White boxes indicate enlarged images shown in insets. Scale bar, 10 µm.

FIG. 7A-7O: Phosphorylation of Lpd by c-Src and c-Abl is required for cancer cell invasion. FIG. 7A: Peptides harbouring all the tyrosine residues in Lpd were directly synthesized onto a membrane. An in vitro kinase assay was performed: the membranes were incubated with purified c-Src kinase and y-32P-ATP. Phosphorylation was detected using a phosphorimager and visualised as high intensity spots. Increasing levels of c-Abl phosphorylation of respective peptides as identified by 9 are indicated by (+), (++), (+++), and (−) for not phosphorylated. Straight rectangles represent the common phosphorylation sites for both c-Src and c-Abl, and dotted rectangles represents c-Abi specific phosphorylation sites. (FIG. 7D) The image stacks were processed by Volocity software to make a 3D reconstruction. (FIG. 7E) Quantification of the number of nuclei of invading cells above 80 µm. n=6 (with approximately 4000 cells per experiment). Data are represented as mean±s.e.m. One-way ANOVA; DunneWs; *P≤0.001, p≤0.0001. Error bars represent s.e.m. FIG. 7I-7O: Lpd phosphorylation by c-Src does not affect LpdNASP interaction. FIG. 7I: HEK293FT cells were transfected with GFP-Lpd, GFP-VASP and either Src-WT (wild-type) or Src-KI (kinase-inactive). Immunoprecipitation was performed from cell lysates using Lpd-specific antibody or rabbit IgG as control followed by Western blotting with anti-GFP and anti-phosphotyrosine (pTyr) antibodies. FIG. 7J: Quantified band intensities of chemiluminescence blots from 7I of GFP-Lpd and GFP-VASP imaged with a CCD camera. VASP was normalised against the immunoprecipitated Lpd. n=3, One-way ANOVA; Dunnett's. Error bars represent s.e.m. FIG. 7K: HEK293FT cells were transfected with GST-Abi2 (which reduces endogenous Abi and thereby replaces it) and either GFP-Src wild type or GFP as control. GST-Abi2 including the other components of the Scar/WAVE complex and associated proteins were pulled down from cell lysates using Glutathion-beads followed by Western blotting with anti-Lpd, anti-Scar/WAVE2 antibodies to detect endogenous proteins. FIG. 7L: Quantified band intensities of chemiluminescence blots (7K) of Lpd and Scar/WAVE2 imaged with a CCD camera. Scar/WAVE2 was normalized against the pulled down Lpd. n=3, data are represented as mean±s.e.m. FIG. 7M: Inverted invasion assays were performed using MDA-MB-231 breast cancer cells stably expressing mCherry-H2B (labelling the nucleus). During the three day incubation period of the assay the upper and lower chamber of the transwell was treated with 10 nM Dasatinib (a dual c-Src and c-Abl inhibitor, which does not inhibit the EGFR at 10 nM (IC50=53 nM) (Rix et al., 2007), 10 µm STI-571 (c-Abl inhibitor), both inhibitors, or DMSO as control. The nuclei of the cells were visualized using confocal microscopy. The image stacks were processed by Volocity software to make a 3D reconstruction. FIG. 7N: Quantification of the number of nuclei of invading cells above 40 µm using Volocity software. n=4, (with approximately 4000 cells per experiment). Data are represented as mean±s.e.m., One-way ANOVA; Dunnett's; * P≤0.0001. FIG. 7O: Quantification of mean protrusion speed from kymographic analysis of MDA-MB-231 transfected with GFP-Lpd, GFP-LpdEVmut, GFP-LpdS/Wmut, GFP-LpdEV+S/Wmut, GFP-LpdY6F GFP-LpdY8F or GFP empty vector as control in a 3D environment. n=35-46 cells for each mutant; from 5 experiments. Data are represented as mean±s.e.m. One-way ANOVA; Dunnett's; * P≤0.05, *** P≤0.001).

FIG. 9A: Comparison of EVH1-binding region on various Mena isoforms. FIG. 9B-9C: Ena/VASP deficient fibroblasts (MVD7 cells) expressing equivalent amounts of either GFP-MenaINV, GFP-Mena11a, GFP-Mena or GFP alone were used for co-Immunoprecipitation experiments in Lpd and associated proteins were pulled down with antibodies to Lpd and then analyzed by western blotting with antibodies to GFP. More MenaINV than Mena or Mena11a were co-immunoprecipitated with Lpd.

DETAILED DESCRIPTION

Figure 1A:
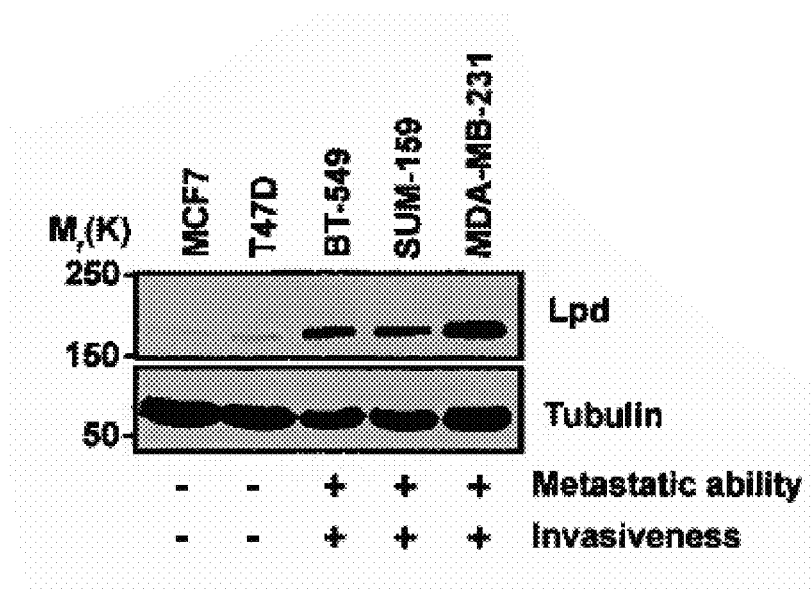
Figure 1B:
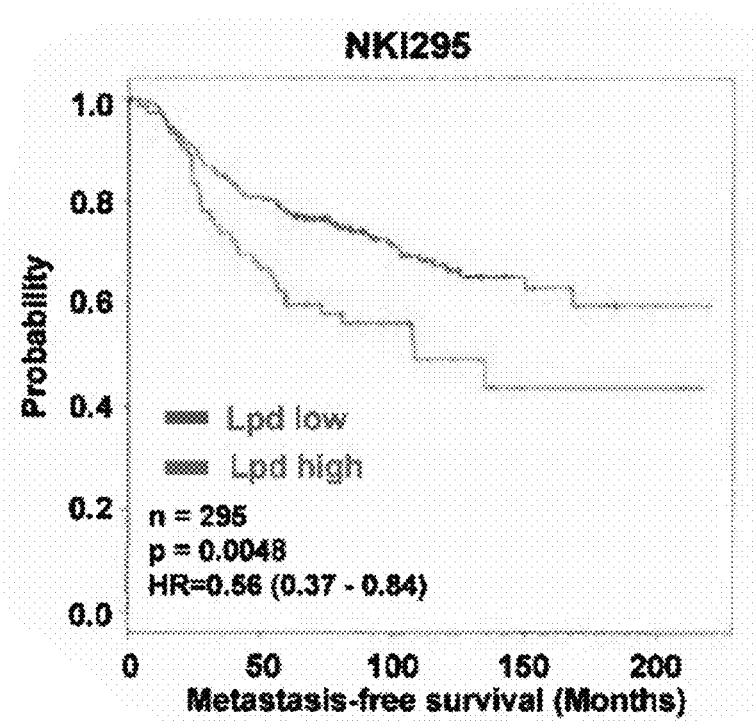
Figure 1C:
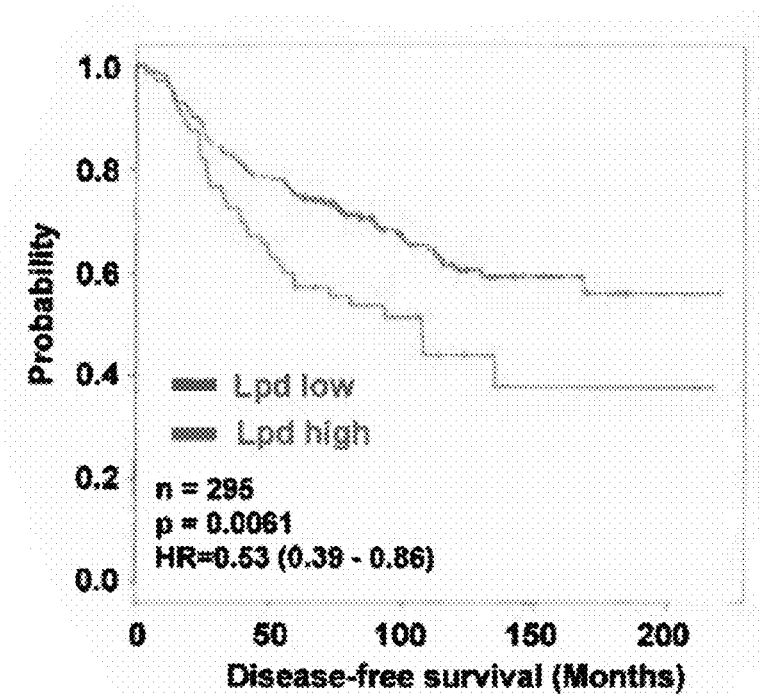

The limitations of sensitivity and reliability of existing biomarkers mean that patients with an increased risk of developing metastatic cancer, or patients in the early stages of the cancer are not necessarily identified of having chances of metastatic cancer in particular, metastatic breast cancer using existing tests. The inability to identify such patients may mean that opportunities for therapeutic intervention prior to the appearance of debilitating symptoms of metastatic cancer are lost. It will be appreciated that a prognostic test, and also diagnostic tests for early metastatic cancer in particular, metastatic breast cancer, are ideally performed before its advancement. In view of the above, the inventors endeavored to develop a prognostic and diagnostic test for metastatic cancer prediction in particular, metastatic breast cancer by testing samples from control subjects and subjects with metastatic cancer or potential metastatic cancer using Lpd nucleic acid and/or protein alone or in combination with other biomarkers.

As described herein, increased Lpd levels (i.e., amount of protein, gene expression or both) correlate with reduced metastasis-free survival and increased breast cancer associated death in breast cancer patients. As indicated above, Lpd is believed to promote metastasis by supporting tumor invasion and intravasation. Mechanistically, it is thought that Lpd functions as an essential component of a pro-metastatic signaling pathway, and can be used alone as a reliable marker for early diagnosis or prognosis of metastatic cancer.

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention.

All publications, patent applications, patents, Figures and other references cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the invention.

Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the meaning commonly understood by a person skilled in the art to which this invention belongs. The following references, the entire disclosures of which are incorporated herein by reference, provide one of skill with a general definition of many of the terms (unless defined otherwise herein) used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, the Harper Collins Dictionary of Biology (1991). Generally, the procedures of molecular biology methods described or inherent herein and the like are common methods used in the art. Such standard techniques can be found in reference manuals such as for example Sambrook et al., (2000, Molecular Cloning—A Laboratory Manual, Third Edition, Cold Spring Harbor Laboratories); and Ausubel et al., (1994, Current Protocols in Molecular Biology, John Wiley & Sons, New-York).

The following terms may have meanings ascribed to them below, unless specified otherwise. However, it should be understood that other meanings that are known or understood by those having ordinary skill in the art are also possible, and within the scope of the present invention. All publications, patent applications, patents, and other references mentioned herein are incorporated by reference in their entirety. In the case of conflict, the present specification, including definitions, will control. In addition, the materials, methods, and examples are illustrative only and not intended to be limiting.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or"

should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The term "effective," "effective amount," "sufficient amount" or the like is used to describe an amount of a compound, composition or component which, when used within the context of its intended use, is sufficient to effectuate an intended result.

A "biomarker" or "marker" as used herein generally refers to a molecule (e.g. protein, polypeptide or polynucleotide) that is differentially present in a sample taken from a subject of one phenotypic status (e.g., having a disease, disorder, or condition) as compared with another phenotypic status (e.g., not having the disease, disorder, or condition). A biomarker is differentially present between different phenotypic statuses if the mean or median level of the biomarker in a first phenotypic status relative to a second phenotypic status is calculated to represent statistically significant differences. Common tests for statistical significance include, among others, t-test, ANOVA, Kruskal-Wallis, Wilcoxon, Mann-Whitney and odds ratio.

Biomarkers, alone or in combination, provide measures of relative likelihood that a subject belongs to a phenotypic status of interest. As such, biomarkers can find use as markers for, for example, disease (diagnostics), progression of disease, therapeutic effectiveness of a drug (theranostics), and of drug toxicity.

"Detect" refers to identifying the presence, absence, level, or concentration of an agent.

By "detectable" is meant a moiety that when linked to a molecule of interest renders the latter detectable. Such detection may be via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

As used herein, the terms "determining", "assessing", "assaying", "measuring" and "detecting" refer to both quantitative and qualitative determinations, and as such, depending on the context, the terms may be used interchangeably herein.

As used herein, the term "invasive cancer" is the cancer that has spread beyond the layer of tissue in which it developed and is growing into surrounding, healthy tissues.

The term "metastatic cancer" as used in the embodiments is the spread of a cancer from one organ or part to another not directly connected with it. Cancer cells can travel from the cancer site to other parts of the body through the blood stream or the lymphatic system. They may travel early in the process when the tumor is small or later when the tumor is large. For example: Metastatic breast cancer (also called stage IV or advanced breast cancer) is breast cancer that has spread beyond the breast to other organs in the body e.g. bones, lungs, liver or brain.

As used herein, the terms "comprises," "comprising," "containing," "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "agent" is meant any small molecule chemical compound, antibody, nucleic acid molecule, or polypeptide, or fragments thereof.

The term "Disease-Free Survival (DFS)" is used herein to refer to time in years to breast cancer recurrence or death from any cause.

By "reference" or "control" can mean a standard of comparison. For example, Lpd or Mena levels present in a patient sample may be compared to the level of the compound(s) in a corresponding healthy cell or tissue or in a diseased cell or tissue (e.g., a cell or tissue derived from a subject having metastatic cancer).

As used herein, the term "sample" includes a biological sample such as any tissue, cell, fluid, or other material derived from an organism. In certain embodiments, the cell or tissue is a cancer cell or cancerous tissue. In still additional embodiments, the cancer cell or cancerous tissue is a breast cancer cell or breast cancer tissue. In certain embodiments, the cells can be obtained from blood, plasma, serum mucus or any body fluids.

The phrase "selectively (or specifically) hybridizes to" refers to the binding, duplexing, or hybridizing of a molecule only to a particular nucleotide sequence under stringent hybridization conditions when that sequence is present in a complex mixture (for example, total cellular or library DNA or RNA).

The term "subject" or "patient" refers to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

As used herein, the terms "treat," treating," "treatment," and the like refer to reducing or ameliorating a disease or condition. It will be appreciated that, although not precluded, treating a disease or condition does not require the condition or symptoms associated with it to be eliminated completely.

The term "siRNA" is used herein to refer to short interfering RNA or silencing RNA, a synthetic RNA duplex of 20-25 base pairs in length, designed to specifically target a particular mRNA for degradation. It interferes with the expression of specific genes with complementary nucleotide sequences. siRNA provides the opportunity to induce gene knockdown in a variety of cell lines. For example: Lpd knockout models to detect its role in invasion or metastasis can be designed by using siRNA complementary to Lpd mRNA. The siRNA can be 5' phosphorylated or not and may be modified with any of the known modifications in the art to improve efficacy and/or resistance to nuclease degradation. In an embodiment the siRNA can be administered such that it is transfected into one or more cells.

In one embodiment, a siRNA of the invention comprises a double-stranded RNA wherein one strand of the double-stranded RNA is 80, 85, 90, 95 or 100% complementary to a portion of an RNA transcript of a gene encoding mammalian Lpd. In another embodiment, a siRNA of the invention comprises a double-stranded RNA wherein one strand of the RNA comprises a portion having a sequence the same as a portion of 18-25 consecutive nucleotides of an RNA transcript of a gene encoding mammalian Lpd.

As used herein, the term "shRNA" refers to a small hairpin RNA or short hairpin RNA (shRNA), an artificial RNA molecule with a tight hairpin turn that can be used to silence target gene expression via RNA interference (RNAi). Expression of shRNA in cells is typically accomplished by delivery of plasmids or through viral or bacterial vectors.

As used herein, the term "upregulated" or "enhanced" refers to an increase as compared to reference. The increase may vary from 0.1% to 99%.

As used herein, the term "polypeptide" encompasses native or artificial proteins, protein fragments and polypeptide analogs of a protein sequence. A polypeptide may be monomeric or polymeric (i.e., formed of multiple units or subunits).

As used herein, unless the context suggests otherwise, the term "antibody" can refer to an intact antibody or antigen-binding protein, i.e. with complete Fc and Fv regions or an antigen-binding "fragment" thereof. "Fragment" refers to any portion of an antibody or antigen-binding protein, or portions of an antibody linked together, such as, in non-limiting examples, a Fab, F(ab)$_2$, a single-chain Fv (scFv), which is less than the whole antibody but which is an antigen-binding portion and which competes with the intact antibody of which it is a fragment for specific binding. As such, a fragment can be prepared, for example, by cleaving an intact antibody or by recombinant means (e.g., an scFv generated by expressing the scFv in a host system and recovering it). See generally, Fundamental Immunology, Ch. 7 (Paul, W., ed., 2nd ed. Raven Press, N.Y. (1989), hereby incorporated by reference in its entirety). Antigen-binding fragments may be produced by recombinant DNA techniques or by enzymatic or chemical cleavage of intact antibodies or by molecular biology techniques. In some embodiments, a fragment is an Fab, Fab', F(ab')$_2$, $F_d$ $F_v$, complementarity determining region (CDR) fragment, single-chain antibody (scFv), (a variable domain light chain ($V_L$) and a variable domain heavy chain ($V_H$) linked via a peptide linker. From N-terminus to C-terminus, both the mature light and heavy chain variable domains comprise the regions FR1, CDR1, FR2, CDR2, FR3, CDR3 and FR4. As used herein, an $F_d$ fragment means an antibody fragment that consists of the $V_H$ and CH1 domains; an $F_v$ fragment consists of the $V_l$ and $V_H$ domains of a single arm of an antibody; and a dAb fragment (Ward et al., Nature 341:544-546 (1989) hereby incorporated by reference in its entirety) consists of a $V_H$ domain. In some embodiments, fragments are at least 5, 6, 8 or 10 amino acids long. In other embodiments, the fragments are at least 14, at least 20, at least 50, or at least 70, 80, 90, 100, 150 or 200 amino acids long.

The assignment of amino acids to each domain is in accordance with the definitions of Kabat, Sequences of Proteins of Immunological Interest (National Institutes of Health, Bethesda, Md. (1987 and 1991)), Chothia & Lesk, J. Mol. Biol. 196:901-917 (1987), or Chothia et al., Nature 342:878-883 (1989), each of which are hereby incorporated by reference in their entirety).

Antibodies of the invention can be monoclonal. The term "monoclonal antibody" is not intended, unless otherwise indicated, to be limited as regards to the source of the antibody or the manner in which it is made (e.g., by hybridoma, phage selection, recombinant expression, transgenic animals, etc.). The term "monoclonal antibody" as used herein refers to an antibody member of a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies.

In certain embodiments, such a monoclonal antibody typically includes an antibody comprising a polypeptide sequence that binds a target Lpd and/or Mena (Patent application PCT/US2013/036336 hereby incorporated by reference in its entirety), wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins. Thus an identified monoclonal antibody can be produced by non-hybridoma techniques, e.g. by appropriate recombinant means once the sequence thereof is identified.

Antibodies of the invention can be isolated antibodies. As used herein, the term "isolated antibody" refers to an antibody that by virtue of its origin or source of derivation has one to four of the following: (1) is not associated with naturally associated components that accompany it in its native state, (2) is free of other proteins from the same species, (3) is expressed by a cell from a different species, or (4) does not occur in nature.

In an embodiment the composition or pharmaceutical composition comprising one or more of the antibodies or fragments described herein is substantially pure with regard to the antibody or fragment. A composition or pharmaceutical composition comprising one or more of the antibodies or fragments described herein is "substantially pure" with regard to the antibody or fragment when at least about 60 to 75% of a sample of the composition or pharmaceutical composition exhibits a single species of the antibody or fragment. A substantially pure composition or pharmaceutical composition comprising one or more of the antibodies or fragments described herein can comprise, in the portion thereof which is the antibody or fragment, 60%, 70%, 80% or 90% of the antibody or fragment of the single species, more usually about 95%, and preferably over 99%. Antibody purity or homogeneity may tested by a number of means well known in the art, such as polyacrylamide gel electrophoresis or HPLC.

Antibodies of the invention can be human antibodies. As used herein, a "human antibody" unless otherwise indicated is one whose sequences correspond to (i.e. are identical in sequence to) an antibody that could be produced by a human and/or has been made using any of the techniques for making human antibodies as disclosed herein, but not one which has been made in a human. This definition of a human antibody specifically excludes a humanized antibody. A "human antibody" as used herein can be produced using various techniques known in the art, including phage-display libraries (e.g. Hoogenboom and Winter, J. Mol. Biol., 227:381 (1991); Marks et al., J. Mol. Biol., 222:581 (1991), hereby incorporated by reference in its entirety), by methods described in Cole et al., Monoclonal Antibodies and Cancer Therapy, Alan R. Liss, p. 77 (1985) (hereby incorporated by reference in its entirety); Boerner et al., J. Immunol., 147 (1):86-95 (1991) (hereby incorporated by reference in its entirety), van Dijk and van de Winkel, Curr. Opin. Pharmacol., 5: 368-74 (2001) (hereby incorporated by reference in its entirety), and by administering the antigen to a transgenic animal that has been modified to produce such antibodies in response to antigenic challenge, but whose endogenous loci have been disabled, e.g., immunized xenomice (see, e.g., U.S. Pat. Nos. 5,939,598; 6,075,181; 6,114,598; 6,150,584 and 6,162,963 to Kucherlapati et al. regarding XENOMOUSE™ technology, each of which patents are hereby incorporated by reference in their entirety), e.g. VelocImmunek (Regeneron, Tarrytown, N.Y.), e.g. UltiMab® platform (Medarex, now Bristol Myers Squibb, Princeton, N.J.). See also, for example, Li et al., Proc. Natl. Acad. Sci. USA, 103:3557-3562 (2006) regarding human antibodies generated via a human B-cell hybridoma technology. See also KM Mouse® system, described in PCT Publication WO 02/43478 by Tshida et al., in which the mouse carries a human heavy chain transchromosome and a human light chain transgene, and the TC mouse system, described in Tomizuka et al. (2000) Proc. Natl. Acad. Sci. USA 97:722-727, in which the mouse carries both a human heavy chain transchromosome and a human light chain transchromosome, both of which are hereby incorporated by reference in their entirety. In each of these systems, the transgenes and/or transchromosomes carried by the mice comprise human immunoglobulin variable and constant region sequences.

The term "human antibody", as used herein, is intended to include antibodies having variable regions in which both the framework and CDR regions are sequences of human origin or identical thereto other than antibodies naturally occurring in a human or made in a human. Furthermore, if the antibody (e.g. an intact antibody rather than, for example, an Fab fragment) contains a constant region, the constant region also is derived from such human sequences, e.g., human germline sequences, or mutated versions of human germline sequences. The human antibodies of the invention may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. In one non-limiting embodiment, where the human antibodies are human monoclonal antibodies, such antibodies can be produced by a hybridoma which includes a B cell obtained from a transgenic nonhuman animal, e.g. a transgenic mouse, having a genome comprising a human heavy chain transgene and a light chain transgene fused to an immortalized cell.

Antibodies of the invention can be recombinant human antibodies. The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Antibodies of the invention can be humanized antibodies. "Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region (HVR) of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin variable domain are replaced by corresponding non-human residues. These modifications may be made to further refine antibody performance. Furthermore, in a specific embodiment, humanized antibodies may comprise residues that are not found in the recipient antibody or in the donor antibody. In an embodiment, the humanized antibodies do not comprise residues that are not found in the recipient antibody or in the donor antibody. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. See, e.g., Jones et al., Nature 321:522-525 (1986); Riechmann et al., Nature 332:323-329 (1988); Presta, Curr. Op. Struct. Biol. 2:593-596 (1992); Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409, the contents of each of which references and patents are hereby incorporated by reference in their entirety. In one embodiment where the humanized antibodies do comprise residues that are not found in the recipient antibody or in the donor antibody, the Fc regions of the antibodies are modified as described in WO 99/58572, the content of which is hereby incorporated by reference in its entirety.

Techniques to humanize a monoclonal antibody are described in U.S. Pat. Nos. 4,816,567; 5,807,715; 5,866,692; 6,331,415; 5,530,101; 5,693,761; 5,693,762; 5,585,089; and 6,180,370, the content of each of which is hereby incorporated by reference in its entirety.

A number of "humanized" antibody molecules comprising an antigen-binding site derived from a non-human immunoglobulin have been described, including antibodies having rodent or modified rodent V regions and their associated complementarity determining regions (CDRs) fused to human constant domains. See, for example, Winter et al. Nature 349: 293-299 (1991), Lobuglio et al. Proc. Nat. Acad. Sci. USA 86: 4220-4224 (1989), Shaw et al. J. Immunol. 138: 4534-4538 (1987), and Brown et al. Cancer Res. 47: 3577-3583 (1987), the content of each of which is hereby incorporated by reference in its entirety. Other references describe rodent hypervariable regions or CDRs grafted into a human supporting framework region (FR) prior to fusion with an appropriate human antibody constant domain. See, for example, Riechmann et al. Nature 332: 323-327 (1988), Verhoeyen et al. Science 239: 1534-1536 (1988), and Jones et al. Nature 321: 522-525 (1986), the content of each of which is hereby incorporated by reference in its entirety. Another reference describes rodent CDRs supported by recombinantly veneered rodent framework regions European Patent Publication No. 0519596 (incorporated by reference in its entirety). These "humanized" molecules are designed to minimize unwanted immunological response toward rodent anti-human antibody molecules which limits the duration and effectiveness of therapeutic applications of those moieties in human recipients. The antibody constant region can be engineered such that it is immunologically inert (e.g., does not trigger complement lysis). See, e.g. PCT Publication No. WO99/58572; UK Patent Application No. 9809951.8. Other methods of humanizing antibodies that may also be utilized are disclosed by Daugherty et al., Nucl. Acids Rcs. 19: 2471-2476 (1991) and in U.S. Pat. Nos. 6,180,377; 6,054,297; 5,997,867; 5,866,692; 6,210,671; and 6,350,861; and in PCT Publication No. WO 01/27160 (each incorporated by reference in their entirety).

Other forms of humanized antibodies have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody.

In embodiments, the antibodies or fragments herein can be produced recombinantly, for example antibodies expressed using a recombinant expression vector transfected into a host cell, antibodies isolated from a recombinant, combinatorial human antibody library, antibodies isolated from an animal (e.g., a mouse) that is transgenic for human immunoglobulin genes.

An antibody "specifically binds" or "preferentially binds" to a target if it binds with greater affinity, avidity, more readily, and/or with greater duration than it binds to other substances. Depending on the amino acid sequences of the constant domains of their heavy chains, antibodies (immunoglobulins) can be assigned to different classes. The antibody or fragment can be, e.g., any of an IgG, IgD, IgE, IgA or IgM antibody or fragment thereof, respectively. In an embodiment the antibody is an immunoglobulin G. In an embodiment the antibody fragment is a fragment of an immunoglobulin G. In an embodiment the antibody is an IgG I, IgG2, IgG2a, IgG2b, IgG3 or IgG4. In an embodiment the antibody comprises sequences from a human IgGi, human IgG2, human IgG2a, human IgG2b, human IgG3 or human IgG4. A combination of any of these antibodies subtypes can also be used. One consideration in selecting the type of antibody to be used is the desired serum half-life of the antibody. For example, an IgG generally has a serum half-life of 23 days, IgA 6 days, IgM 5 days, IgD 3 days, and IgE 2 days. (Abbas A K, Lichtman A H, Pober J S. Cellular and Molecular Immunology, 4th edition, W.B. Saunders Co., Philadelphia, 2000, hereby incorporated by reference in its entirety).

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites. The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (K) and lambda (k), based on the amino acid sequences of their constant domains. "Framework" or "FR" residues are those variable domain residues other than the HVR residues as herein defined.

The term "hypervariable region" or "HVR" when used herein refers to the regions of an antibody variable domain which are hypervariable in sequence and/or form structurally defined loops. Generally, antibodies comprise six HVRs; three in the VH (H1, H2, H3) and three in the $V_L$ (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363: 446448 (1993); Sheriff et al., Nature Struct. Biol. 3:733-736 (1996). A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991) hereby incorporated by reference in its entirety). Chothia refers instead to the location of the structural loops (Chothia and Lesk, J. Mol. Biol. 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. HVRs may comprise "extended HVRs" as follows: 24-36 or 2434 (L), 46-56 or 50-56 (L2) and 89-97 or 89-96 (L3) in the VL and 26-35 (H1), 50-65 or 4965 (H2) and 93-102, 94-102, or 95-102 (H3) in the VH. The variable domain residues are numbered according to Kabat et al., supra, for each of these definitions.

Compositions or pharmaceutical compositions comprising the antibodies, ScFvs or fragments of antibodies disclosed herein are preferably comprise stabilizers to prevent loss of activity or structural integrity of the protein due to the effects of denaturation, oxidation or aggregation over a period of time during storage and transportation prior to use. The compositions or pharmaceutical compositions can comprise one or more of any combination of salts, surfactants, pH and tonicity agents such as sugars can contribute to overcoming aggregation problems. Where a composition or pharmaceutical composition of the present invention is used as an injection, it is desirable to have a pH value in an approximately neutral pH range, it is also advantageous to minimize surfactant levels to avoid bubbles in the formulation which are detrimental for injection into subjects. In an embodiment, the composition or pharmaceutical composition is in liquid form and stably supports high concentrations of bioactive antibody in solution and is suitable for parenteral administration, including intravenous, intramuscular, intraperitoneal, intradermal and/or subcutaneous injection.

In an embodiment, the composition or pharmaceutical composition is in liquid form and has minimized risk of bubble formation and anaphylactoid side effects. In an embodiment, the composition or pharmaceutical composition is isotonic. In an embodiment, the composition or pharmaceutical composition has a pH or 6.8 to 7.4.

Examples of pharmaceutically acceptable carriers include, but are not limited to, phosphate buffered saline solution, sterile water (including water for injection USP), emulsions such as oil/water emulsion, and various types of wetting agents. Preferred diluents for aerosol or parenteral administration are phosphate buffered saline or normal (0.9%) saline, for example 0.9% sodium chloride solution, USP. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000, the content of each of which is hereby incorporated in its entirety).

The antibodies or fragments of antibodies, or compositions, or pharmaceutical compositions described herein can also be lyophilized or provided in any suitable forms including, but not limited to, injectable solutions or inhalable solutions, gel forms and tablet forms.

As used herein a "small organic molecule" is an organic compound which contains carbon-carbon bonds, and has a molecular weight of less than 2000. The small molecule may be a substituted hydrocarbon or an substituted hydrocarbon. In an embodiment, the small molecule has a molecular weight of less than 1500. In an embodiment, the small molecule has a molecular weight of less than 1000.

The present description also encompasses nucleic acids, e.g., oligonucleotide probes, that hybridize under selective hybridization conditions, e.g., low, medium or high stringency, to a Lpd-polynucleotide, for example, a Lpd-encoding nucleic acid. Thus, the diagnostic polynucleotides can be used for isolating, detecting, and/or quantifying nucleic acids comprising such polynucleotides. For example, polynucleotides can be used to identify, isolate, or amplify partial or full-length transcripts of Lpd according to known methods. In some embodiments, the Lpd-specific nucleic acids are capable of binding specifically at under high stringency conditions to Lpd-polynucleotides, e.g., genomic, RNA, or cDNA sequences, whether in situ or isolated.

Methods of Assessing Metastatic Cancer

Cancer cell metastasis requires cellular capacity to 1) detach from a primary tumor, 2) migrate and invade through local tissues, 3) translocate to distant sites in the body (via lymph or blood), 4) colonize a foreign site, and 5) grow and survive in this foreign environment. All of these behaviors are linked to cell adhesions. Cell adhesions control the physical interactions of cells with their microenvironment. Cell adhesions also initiate signals that dictate tumor cell growth, death, and differentiation (U.S. Pat. No. 7,192,698 incorporated herein by reference in its entirety).

Metastatic cancer is the advanced stage of cancer where the cancer has spread to other parts of the body. There is a great need of a reliable biomarker for diagnosing or prognosing metastatic cancer at early stage for improved survivability and better treatment. The present invention discloses that increased Lpd levels correlate with reduced metastasis free survival in breast cancer patients. Lpd promotes metastasis by supporting tumor invasion and intravasation. Lpd functions as an essential component of a pro-metastatic signaling pathway and can be used as a reliable marker for early diagnosis or prognosis of metastatic cancer.

In certain aspects, the description provides methods for assessing, e.g., diagnosing or prognosing, a metastatic cancer. In certain embodiments, the method comprises obtaining a biological sample from a subject. In additional embodiments, the method involves determining the amount of Lamellipodin (Lpd) protein or Lpd gene expression level or both in the sample, e.g., by detecting the presence of Lpd and/or measuring the amount of Lpd protein or nucleic acids. In further embodiments, the method involves correlating the amount of Lpd protein or gene expression level or both to the metastatic state or capacity of cells in the sample, wherein an enhanced amount of Lpd protein or upregulated gene expression of Lpd is indicative of a metastatic cancer or a cancer at risk of becoming metastatic.

In certain aspects, the description provides methods for assessing, e.g., diagnosing or prognosing, a metastatic cancer. In certain embodiments, the method consists essentially of obtaining a biological sample from a subject. In additional embodiments, the method involves determining the amount of Lamellipodin (Lpd) protein or Lpd gene expression level or both in the sample, e.g., by detecting the presence of Lpd and/or measuring the amount of Lpd protein or nucleic acids. In further embodiments, the method involves correlating the amount of Lpd protein or gene expression level or both to the metastatic state or capacity of cells in the sample, wherein an enhanced amount of Lpd protein or upregulated gene expression of Lpd is indicative of a metastatic cancer or a cancer at risk of becoming metastatic.

As described herein, Lpd alone is sufficient to diagnose or prognose metastatic cancer or the risk of a cancer becoming metastatic. Accordingly, in certain embodiments, the methods relate to the measurement of Lpd alone (either protein, gene expression or both). In certain additional embodiments, the methods comprise measuring Lpd in addition to another biomarker of metastatic cancer, e.g., Mena and its isoforms (either protein, gene expression or both).

In any of the aspects or embodiments described herein, the amount of protein or level of gene expression that is indicative of a metastatic cancer or cancer capable of becoming metastatic, respectively, is from 0.5% to 100% or more above baseline or control levels. In certain embodiments, the amount of increase is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% or more above baseline or control levels.

In any of the aspects or embodiments described herein, the amount of protein or level of gene expression that is indicative of a metastatic cancer or cancer capable of becoming metastatic, respectively, is increased by at least about 0.5 fold relative to baseline or control levels. In certain embodiments, the amount of increase is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 fold or more above baseline or control levels.

In an additional aspect, the description provides methods for diagnosing or prognosing metastatic cancer in a subject comprising obtaining a biological sample from a subject; determining the amount of Lamellipodin (Lpd) protein or expression level or both in the sample; comparing the amount of Lpd protein or gene expression level or both in the sample with that of a control; and correlating the amount of Lpd protein or gene expression level or both to the metastatic state or capacity of cells in the sample, wherein an enhanced amount of Lpd protein or upregulated gene expression of Lpd relative to the control is indicative of a metastatic cancer or a cancer at risk of becoming metastatic.

In any of the aspects or embodiments described herein, the method may include a step of diagnosing the subject as having no metastatic cancer or having metastatic cancer or making a prognosis that the subject is at risk of developing metastatic cancer.

The description further provides method for diagnosing or prognosing metastatic cancer in a subject, the method comprising obtaining a biological sample from a subject; detecting and/or measuring the amount of Lamellipodin (Lpd) protein with an Lpd-specific antibody or Lpd-binding polypeptide; determining the amount of Lamellipodin (Lpd) protein in the sample; and correlating the amount of Lpd protein to the metastatic state or capacity of cells in the sample, wherein an enhanced amount of Lpd protein is indicative of a metastatic cancer or a cancer at risk of becoming metastatic.

In certain embodiments, the Lpd-specific antibody or Lpd-binding polypeptide antibody binds to an epitope of an Lpd protein having the amino acid sequence of SEQ ID NO:2.

In certain embodiments, the methods include further detecting the amount of MENA protein by determining the amount of binding by a MENA-specific antibody or MENA-binding polypeptide. In certain embodiments, the MENA-specific antibody or MENA-binding polypeptide binds to an epitope of a MENA protein having the amino acid sequence of SEQ ID NO:4.

In any of the aspects or embodiments described herein, the description provides methods of assessing or treating a subject at risk of or having metastatic breast cancer comprising the steps of obtaining a breast tissue or breast cancer tissue sample from a subject; determining the amount of Lamellipodin (Lpd) protein or expression level or both in the sample; comparing the amount of Lpd protein or expression level or both in the sample with that of a control; correlating the amount of Lpd protein or expression level or both to the metastatic state or capacity of cells in the sample, wherein an enhanced amount of Lpd protein or upregulated expression of Lpd relative to the control is indicative of a metastatic cancer or a cancer at risk of becoming metastatic. In certain embodiments, the above method can be combined with one or more additional steps as described herein, including, e.g., administering a therapeutic course to a subject having metastatic cancer or being at risk of developing metastatic cancer.

It is known in the art to use antibodies to detect the presence or overexpression of a specific protein. In any of the aspects or embodiments described herein, an antibody or antigen-binding protein as described herein can be employed. Because Lpd, as observed here, is overexpressed in metastatic cells, Lpd-specific antibodies in various aspects of this invention may be used to detect this overexpression and, thus, to detect, diagnose or assess the risk of developing metastatic cancer. Such techniques include but are not limited to Western blotting, dot blotting, precipitation, agglutination, ELISA assays, immunohistochemistry, in situ hybridization, Flow cytometry on a variety of tissues or bodily fluids, and a variety of sandwich assays. These techniques are well known in the art. See, for example, U.S. Pat. No. 5,876,949, herein incorporated by reference. As such, in certain embodiments, the step of detecting, determining or measuring the amount of Lpd protein may include Western blotting, dot blotting, precipitation, agglutination, ELISA assay, immunohistochemistry, immunocytochemistry, flow cytometry or FACS sorting, or the like.

In connection with nucleic acid probe hybridization, the term "specifically hybridizes" indicates that the probe hybridizes to a sufficiently greater degree to the target sequence than to a sequence having a mismatched base at least one variance site to allow distinguishing such hybridization. The term "specifically hybridizes," thus refers to the probe hybridizing to the target sequence, and not to non-target sequences, at a level which allows ready identification of probe/target sequence hybridization under selective hybridization conditions. Thus, "selective hybridization conditions" refer to conditions that allow such differential binding. Similarly, the terms "specifically binds" and "selective binding conditions" refer to such differential binding of any type of probe, e.g., antibody probes or nucleic acid probes, and/or to the conditions that allow such differential binding.

In order to detect overexpression or altered distribution of Lpd in various aspects of this invention, the Lpd specific antibodies may be labeled covalently or non-covalently with any of a number of known detectable labels, such fluorescent, radioactive, or enzymatic substances, as is known in the art. Alternatively, a secondary antibody specific for the antibodies of this invention is labeled with a known detectable label and used to detect the Lpd-specific antibodies in the above techniques.

In another aspect, the description provides methods for diagnosing or prognosing metastatic cancer in a subject. In an embodiment, the method includes obtaining a biological sample from a subject; detecting the level of Lamellipodin (Lpd) gene expression with a nucleic acid that hybridizes specifically to or is complementary to an Lpd-encoding nucleic acid, e.g., an mRNA or cDNA, such as SEQ ID NO: 1; determining the level of Lpd gene expression in the sample; and correlating the level of Lpd gene expression to the metastatic state or capacity of cells in the sample, wherein an enhanced level of Lpd gene expression is indicative of a metastatic cancer or a cancer at risk of becoming metastatic.

Preferably, a nucleic acid suitable for detecting the Lpd gene or transcript is complementary to the Lpd gene or transcript. In certain embodiments, the nucleic acid suitable for detecting the Lpd gene or transcript is complementary to the nucleic acid sequence of SEQ ID NO: 1.

As is known, an amino acid is "complementary" to another nucleic acid if the two sequences are capable of hybridizing and forming a stable duplex (or triplex) with one another, with hybridization preferably being carried out under conditions which allow specific hybridization between polynucleotides (stringent conditions). Stringent conditions are described, for example, in Molecular Cloning: A Laboratory Manual, J. Sambrook et al., Editors, 2nd Edition, Cold Spring Harbor Laboratory press, Cold Spring Harbor, N.Y., 1989 or Current Protocols in Molecular Biology, F. M. Ausubel et al., Editors, John Wiley & Sons, Inc., New York and refer, for example, to hybridization at 65° C. in hybridization buffer (3.5×SSC, 0.02% Ficoll, 0.02% polyvinylpyrrolidone, 0.02% bovine serum albumin, 2.5 mM NaH2PO4 (pH 7), 0.5% SDS, 2 mM EDTA). SSC is 0.15 M sodium chloride/0.15 M sodium citrate, pH 7. After hybridization, the membrane to which the DNA has been transferred is washed, for example, in 2×SSC at room temperature and then in 0.1-0.5×SSC/0.1×SDS at temperatures of up to 68° C. In certain embodiments, complementary nucleic acids preferably have at least 50%, at least 60%, at least 70%, at least 80%, at least 90% and preferably at least 95%, at least 98% or at least 99%, identical nucleotides.

In certain embodiments, the methods include further detecting the amount of MENA gene expression by determining the amount of binding of a nucleic acid complementary to a MENA gene or transcript. In certain embodiments, the MENA transcript has the nucleic acid sequence of SEQ ID NO: 3.

The polymerase chain reaction (PCR) is a widely known method for amplifying nucleic acids. Of the PCR techniques, RT-PCR (Reverse Transcription-PCR), competitive RT-PCR and the like are used for detecting and quantifying a trace amount of mRNA, and show their effectiveness. In recent years, a real-time quantitative detection technique using PCR has been established (TaqMan PCR, Genome Res., 6 (10), 986 (1996), ABI PRISM™. Sequence Detection System, Applied Biosystems). This technique measures the amount of nucleic acids using a particular fluorescent-labeled probe (TaqMan probe). More specifically, this technique utilizes the following principles: For example, a fluorescent-labeled probe having a reporter dye at the 5' end and a quencher dye at the 3' end is annealed to the target DNA, and the DNA is subjected to normal PCR. As the extension reaction proceeds, the probe is hydrolyzed from the 5' end by the 5'-3' exonuclease activity possessed by DNA polymerase. As a result, the reporter dye at the 5' end is separated from the quencher dye at the 3' end, thereby eliminating the FRET (Fluorescence Resonance Energy Transfer, the reduction in fluorescence intensity owing to the decrease in the energy level of the reporter dye caused by the resonance of the two fluorescent dyes) effect produced by the spatial proximity between the two dyes, and increasing the fluorescence intensity of the reporter dye that has been controlled by the quencher dye. The target nucleic acid can be selectively quantified and detected in real-time by measuring the increase of the fluorescence intensity. (PCT/US2008/000310 is incorporated herein by reference in its entirety). This technique is advantageous in that it can test various samples simultaneously in a short time, since, unlike the detection and quantification technique using conventional PCR it does not involve complicated steps, such as agarose gel electrophoresis of the amplified product after PCR and analysis of the electrophoresis pattern.

Generally, when conducting clinical tests in a clinical test center or the like, it is necessary to inspect an extremely large number of samples within a limited time. In preferred embodiments, the detection of the presence or absence of the at least one variance involves contacting a nucleic acid sequence corresponding to one of the genes identified herein, e.g., Lpd or Mena, or a product of such a gene with a probe. The probe is able to distinguish a particular form of the gene or gene product or the presence or a particular variance or variances, e.g., by differential binding or hybridization. Thus, exemplary probes include nucleic acid hybridization probes, peptide nucleic acid probes, nucleotide-containing probes which also contain at least one nucleotide analog, and antibodies, e.g., monoclonal antibodies, and other probes as discussed herein. Those skilled in the art are familiar with the preparation of probes with particular specificities. Those skilled in the art will recognize that a variety of variables can be adjusted to optimize the discrimination between two variant forms of a gene, including changes in salt concentration, temperature, pH and addition of various compounds that affect the differential affinity of GC vs. AT base pairs, such as tetramethyl ammonium chloride. (See Current Protocols in Molecular Biology by F. M. Ausubel, R. Brent, R. E. Kingston, D. D. Moore, J. D. Seidman, K. Struhl, and V. B Chanda (editors, John Wiley & Sons).

Thus, provided herein are probes which specifically recognize a nucleic acid sequence corresponding to SEQ ID NO: 1 and/or 3, a variance or variances in a gene or a product expressed from the gene, and are able to distinguish a variant form of the sequence or gene or gene product from one or more other variant forms of that sequence, gene, or gene product under selective conditions. Such genes, include, for example Lpd, Mena, GenBank accession nos.: AY494951 and AY345143, respectively, which are hereby incorporated by reference in their entirety. Those skilled in the art recognize and understand the identification or determination of selective conditions for particular probes or types of probes. An exemplary type of probe is a nucleic acid hybridization probe, which will selectively bind under selective binding conditions to a nucleic acid sequence or a gene product corresponding to one of the genes identified for aspects above. Another type of probe is a peptide or protein, e.g., an antibody or antibody fragment which specifically or preferentially binds to a polypeptide expressed from a particular form of a gene as characterized by the presence or absence of at least one variance. Thus, in another aspect, the invention concerns such probes. In the context of this invention, a "probe" is a molecule, commonly a nucleic acid, though also potentially a protein, carbohydrate, polymer, or small molecule, that is capable of binding to one variance or variant form of the gene to a greater extent than to a form of the gene having a different base at one or more variance sites, such that the presence of the variance or variant form of the gene can be determined. Preferably the probe distinguishes at least one variance identified in Examples.

```
Human Lamellipodin cDNA, 5372 bp (Accession: AY494951)
                                                              (SEQ ID NO: 1)
   1  cccgccccg  ctcccgccgc  cgcccgccag  tcagtcagtc  agtcagtcag  tcagtcagtc 61  agtcagtcag  tcactgagcg  cgcggcgcgg  gagctgctgg  cagtcgctgc  gtctctggcg 121  agggagcgcc  gcgcctgggg  aggaggcgga  ggcagcggct  ggaggagcgc  gagcggcggt 181  ttccttgccc  ggggccgcgg  gaaggccgac  cgactgccgc  gatggagcag  ctatcagatg 241  aagaaattga  tcatggtgct  gaagaagaca  gtgacaagga  agatcaggac  ctggacaaaa 301  tgtttggagc  ctggcttgga  gaactagaca  aactcactca  gagtttggat  tctgacaagc 361  ccatggaacc  agtaaaaaga  tctcctcttc  gccaggaaac  aaacatggcc  aactttctt 421  accgcttctc  catatacaac  ttgaatgaag  ctctgaatca  gggagagact  gtggatctgg 481  atgccttgat  ggctgatctt  tgctctatag  agcaggagct  cagcagcatt  ggttcaggaa 541  acagtaagcg  tcaaatcaca  gaaacgaaag  ctactcagaa  attgcctgtt  agccgacata 601  cattgaaaca  tggcaccttg  aaaggattat  cttcttcatc  taataggata  gctaaacctt 661  cccatgccag  ctactccttg  gacgacgtca  ctgcacagtt  agaacaggcc  tctttgagta 721  tggatgaggc  tgctcagcaa  tctgtactag  aagatactaa  acccttagta  actaatcagc 781  acagaagaac  cgcgtcagca  ggcacagtga  gtgatgctga  agtacactct  attagtaatt 841  cctcccattc  cagcatcact  tccgcagcct  ccagcatgga  ctctttggat  attgataaag 901  taacacgccc  tcaagagctg  gatttgacac  atcaagggca  gccaattact  gaggaagaac 961  aggcagcaaa  attgaaagct  gagaagatca  gagttgccct  agagaaaatt  aaagaggcac 1021  aagtgaaaaa  gctggtgatc  agagtccaca  tgtctgatga  cagttctaaa  acaatgatgg 1081  tggatgagag  gcagacagta  agacaagtac  tggataacct  gatggacaaa  tcccactgcg 1141  gttatagttt  agactggtca  ctggtagaaa  ccgtttctga  attacaaatg  gagagaatct 1201  ttgaagacca  tgaaaacttg  gttgaaaatc  ttcttaattg  gacaagagat  agccaaaaca 1261  agcttatatt  tatggagcgt  atagaaaaat  atgcactttt  caaaaaccca  cagaattatc 1321  ttttggggaa  aaaggaaaca  gctgagatgg  cagatagaaa  caagaagtc  ctcttggagg 1381  aatgttttg  tggaagttct  gtaactgtac  cagaaattga  aggagtcctt  tggttgaagg 1441  atgatggcaa  gaagtcctgg  aaaaagcgtt  attttctctt  gcgagcatct  ggtatctact 1501  atgttcccaa  aggaaaagca  aaggtctctc  gggatctggt  gtgctttctc  cagctggatc 1561  atgtcaacgt  ttattatggc  caggactatc  ggaacaaata  caaagcacct  acagactatt 1621  gtctggtgct  gaagcatcca  caaatccaga  agaaatctca  atatatcaaa  tacctttgtt 1681  gtgatgatgt  gaggacactg  catcagtggg  tcaatgggga  ccgcattgca  aagtatggga
```

-continued

```
1741  agcagctcta tatgaactac caagaagcct tgaagaggac agagtcagcc tatgattgga
1801  cttccttatc cagctccagc attaaatcgg gatccagttc ttccagcatc ccagagtctc
1861  agtcaaacca ctccaatcag tctgatagcg gagtttctga cacccagcca gcaggacacg
1921  tccgttccca gagcattgtg agctccgtat tctctgaagc tggaaacga ggcactcagt
1981  tggaagagtc cagcaaggcc agaatggagt ctatgaatcg ccctacact tcacttgtgc
2041  cccctttatc cccgcaacct aagatagtca ccccctacac tgcttcacag ccttcaccac
2101  ctctacctcc tccgccaccc ccacctcctc ctccaccacc cctccacca ccccctcctc
2161  ccccactccc cagccagtct gcaccttctg caggctcagc agccccaatg ttcgtcaagt
2221  acagcacaat aacacggcta cagaatgcgt ctcagcattc aggggccctg tttaagccgc
2281  caacaccccc agtgatgcag tcacagtcag tgaagcctca gatcctggta cccccaatg
2341  gagttgttcc accacccct cccctcctc caccccaac cccaggctct gccatggccc
2401  agctaaagcc tgcaccgtgt gccccatccc ttccacagtt cagtgccccg cctcctccac
2461  tgaagatcca tcaagttcag catattactc aggtggctcc cccaacaccc ccccacctc
2521  ctcctatccc tgcacccctc cctccccaag ctcccccaaa accccttgtg accatccccg
2581  caccaaccag caccaagact gtggcacctg ttgtgactca agctgcacca cccacaccta
2641  ctcctccagt gcccccagca aaaaagcagc cagctttccc tgcttcttac attccaccct
2701  ctccccctac ccctcctgtt ccagtacccc cgccaacatt acccaagcaa cagagcttct
2761  gtgcaaaacc ccctccctct ccactgtcac cggtgccctc ggtcgtgaag cagatagcca
2821  gccagttttcc accccctcca actcccctg ccatggaatc tcagcccta aagcctgtcc
2881  cagcaaatgt agctccacag tcccctcctg cagtaaaagc aaagcccaag tggcagccca
2941  gctccatccc agtcccttct ccggacttcc ctcctccccc tcctgaaagc agcctggtgt
3001  ttcctcctcc accccatca cctgtcccag ccccaccacc gccacctcca cccacagctt
3061  ctcctacccc tgacaaaagt ggatctccag gcaaaaagac cagtaagacg tccagccctg
3121  ggggaaagaa accaccccca accccacagc gcaactccag cattaaatcc agcagtggtg
3181  cagagcaccc cgagcccaag agaccctcgg tggacagtct agtcagcaag tttacaccgc
3241  cagcagaatc agggtctccc agcaaggaga ccctaccacc tcctgcagca ccccccaagc
3301  ctggaaaact caatctttct ggagtcaacc ttcctggagt tctccaacaa gggtgtgtgt
3361  cagcaaaagc ccctgttctg agtgggcgtg gaaaggactc cgtggtggaa tttccttctc
3421  ctccatccga ttctgatttt tcaccccctc cacctgaaac agaccttcct ctgccccca
3481  ttgagattcc agcagttttc tcgggaaaca cctctccaaa agtggcagtc gttaatcctc
3541  aaccacaaca atggtctaaa atgtcagtga agaaggcccc tccacccaca cgacccaaac
3601  ggaatgatag caccccgcctc actcaagctg agatttctga gcagccaaca atggccacag
3661  ttgtgccaca agtgccacc tctcccaaat ccagccttag tgtccagcct ggattcctgg
3721  ctgacctcaa caggacactg caacgaaagt ccatcactcg gcacggctca ctctcctccc
3781  gcatgtccag agcagaacca acagccacca tggatgatat ggcattgcct ccaccacccc
3841  ctgaactgct gtctgatcaa cagaaggctg gttacggagg cagtcatata tcaggctatg
3901  caacgttgcg gagaggaccc cctcctgctc cccccaaaag agaccgaaac accaagctct
3961  ccagagactg gtagccacca taggacttta ttttcatgat atctgtaatc actgctacaa
4021  tcagctcacc tgatcatctg tgaattcagg tgttcagagc ctcctggtat gatgttattc
4081  aggtagtgtc cagctatatg tgtatgtgtg tgtgtacacg tgcatgtaca cacagctgta
```

-continued

```
4141  cagtgtgtgt atatatgtat acatatatgt atgtgtatgt gtatatagag agagagctga
4201  gagttattct atttattcct tttctctcct aatctgaaaa tgggtgttct gtattttggg
4261  tggaagaggc atagaagggg atgtgtgttg tctcttaaga tttctatatc atgtggattg
4321  gaccaaaaac ttctaatcac ttatttagaa ggtatttata agtgtctgtc catgtgtagc
4381  ctattcgtgc atgttgtgta ttatataact aaggaataga gtagaatgt gctatttctg
4441  gttgagaaaa atcaccagaa tgtttggtgt atctataagg cttttgtgtt tgttttccc
4501  cagttggctg aagttagaat tgcttgactg acacttcatt gctatacatg aagggcact
4561  ttaaatcagg aaaatctctc agcttcatag aacgggtaac tagtgcagga tggggaaatg
4621  ttcacagaca tcatctgtat gtggttgtgc atagaaagta aatacatggc gtaattaact
4681  cagctgttct agctgcagta ctgctgcagt gatccaccca catttaggat gtgctgacag
4741  ataagctctt tgcctacaat acatggataa ttagtgctat aattctggat agttccttt
4801  tagtactgtt ttatgaagct ttatcaactt ggcttcatga tcctcacttt gattgatttt
4861  aagaggatgg ataacacagt tatctctgta atgttctgtc ccagtatgtc tttgggtcac
4921  cagttacctt cttaaaatat gtgctttagg taggtgttat tacatatctg tagacaattg
4981  gtatatgaaa tatacacatc ctgtgcccca atatggtgca ttatgaaaaa caaatcatt
5041  ttctaaaatg cattttttga gcattgctct atagaaggga agggtgatga gagaacagaa
5101  ctggcccctg tacaggtgtc attaatctgg ttgtatatg gttataatat gtaatacaaa
5161  aagctcatta agtatgggac tacatggaga gggaagacag tttcatttat agctactggg
5221  gctaccagga cccttgctga ctgcagcctg gttgtgatta gttcaggtta ctaggtgttc
5281  tgatggagtg ggacagtcca agtccagtaa ctgacattac gttttatgcg tgtgcagttt
5341  ggtataacgt ggagtcagtg ctctaacgac ac
```

(SEQ ID NO: 2) Human Lamellipodin amino acid sequence (1250 aa):
MEQLSDEEIDHGAEEDSDKEDQDLDKMFGAWLGELDKLTQSLDSDKPMEPVKRSPLRQETNMANFSYRFSIYNLNEA
LNQGETVDLDALMADLCSIEQELSSIGSGNSKRQITETKATQKLPVSRHTLKHGTLKGLSSSSNRIAKPSHASYSLD
DVTAQLEQASLSMDEAAQQSVLEDTKPLVTNQHRRTASAGTVSDAEVHSISNSSHSSITSAASSMDSLDIDKVTRPQ
ELDLTHQGQPITEEEQAAKLKAEKIRVALEKIKEAQVKKLVIRVHMSDDSSKTMMVDERQTVRQVLDNLMDKSHCGY
SLDWSLVETVSELQMERIFEDHENLVENLLNWTRDSQNKLIFMERIEKYALFKNPQNYLLGKKETAEMADRNKEVLL
EECFCGSSVTVPEIEGVLWLKDDGKKSWKKRYFLLRASGIYYVPKGKAKVSRDLVCFLQLDHVNVYYGQDYRNKYKA
PTDYCLVLKHPQIQKKSQYIKYLCCDDVRTLHQWVNGIRIAKYGKQLYMNYQEALKRTESAYDWTSLSSSSIKSGSS
SSSIPESQSNHSNQSDSGVSDTQPAGHVRSQSIVSSVESEAWKRGTQLEESSKARMESMNRPYTSLVPPLSPQPKIV
TPYTASQPSPPLPPPPPPPPPPPPPPPPPPPLPSQSAPSAGSAAPMFVKYSTITRLQNASQHSGALFKPPTPPVMQ
SQSVKPQILVPPNGVVPPPPPPPPPPTPGSAMAQLKPAPCAPSLPQFSAPPPPLKIHQVQHITQVAPPTPPPPPPIP
APLPPQAPPKPLVTIPAPTSTKTVAPVVTQAAPPTPTPPVPPAKKQPAFPASYIPPSPPTPPVPVPPPTLPKQQSFC
AKPPPSPLSPVPSVVKQIASQFPPPPTPPAMESQPLKPVPANVAPQSPPAVKAKPKWQPSSIPVPSPDFPPPPPESS
LVFPPPPPPSPVPAPPPPPPPTASPTPDKSGSPGKKTSKTSSPGGKKPPPTPQRNSSIKSSSGAEHPEPKRPSVDSLV
SKFTPPAESGSPSKETLPPPAAPPKPGKLNLSGVNLPGVLQQGCVSAKAPVLSGRGKDSVVEEPSPPSDSDEPPPPP
ETDLPLPPIEIPAVESGNTSPKVAVVNPQPQQWSKMSVKKAPPPTRPKRNDSTRLTQAEISEQPTMATVVPQVPTSP
KSSLSVQPGFLADLNRTLQRKSITRHGSLSSRMSRAEPTATMDDMALPPPPPELLSDQQKAGYGGSHISGYATLRRG
PPPAPPKRDQNTKLSRDW Human MENA cDNA, 2302 bp (Accession: AY345143)

(SEQ ID NO: 3)
```
   1  cggcggccgg gcgcgcggcc ccggcgggca cccctcaaag ggcggccgag gaagctccgg
```

-continued

```
  61  gaggaggagc agggaccacg agggaggtgg gaggcggcgg ccgcctgggg accagctccg
 121  cgcctcggcc tctccgcccc ctccccagcc tttctctcgc cctcttctcc cacactcccg
 181  gccggcgcct cggctttgtg cgaggagatg gtgtagcccc ctggccgccg aaggaggagc
 241  cggacacttg tctcccgtct ccgagctgct ccccacccct ggaggagaga cccccccctc
 301  ggctcggcgc cttctgcgtc tcccggctgg tggggaagcc tctgcgccgc cggcaccatg
 361  agtgaacaga gtatctgtca ggcaagagct gctgtgatgg tttatgatga tgccaataag
 421  aagtgggtgc cagctggtgg ctcaactgga ttcagcagag ttcatatcta tcaccataca
 481  ggcaacaaca cattcagagt ggtgggcagg aagattcagg accatcaggt cgtgataaac
 541  tgtgccattc ctaaagggtt gaagtacaat caagctacac agaccttcca ccagtggcga
 601  gatgctagac aggtgtatgg tctcaacttt ggcagcaaag aggatgccaa tgtcttcgca
 661  agtgccatga tgcatgcctt agaagtgtta aattcacagg aaacagggcc aacattgcct
 721  agacaaaact cacaactacc tgctcaagtt caaaatggcc catcccaaga agaattggaa
 781  attcaaagaa gacaactaca agaacagcaa cggcaaaagg agctggagcg ggaaaggctg
 841  gagcgagaaa gaatggaaag agaaaggttg gagagagaga ggttagaaag ggaaaggctg
 901  gagagggagc gactggaaca agaacagctg gagagagaga gacaagaacg ggaacggcag
 961  gaacgcctgg agcggcagga acgcctggag cggcaggaac gcctggagcg gcaggaacgc
1021  ctggatcggg agaggcaaga aagacaagaa cgagagaggc tggagagact ggaacgggag
1081  aggcaagaaa gggagcgaca agagcagtta gaaagggaac agctggaatg ggagagagag
1141  cgcagaatat caagtgctgc tgcccctgcc tctgttgaga ctcctctaaa ctctgtgctg
1201  ggagactctt ctgcttctga gccaggcttg caggcagcct tcagccggc cgagactcca
1261  tcccaacagg gcattgtctt gggaccactt gcacctccac ctcctccacc actcccacca
1321  gggcctgcac aggcttcagt agccctccct cctcccccag ggcccccctcc acctcctcca
1381  ctcccatcca ccgggcctcc accgccccct cctcccctc tctccctaa tcaagtaccc
1441  cctcctcctc caccacctcc tgccccaccc ctccctgcat ctggattctt tttggcatcc
1501  atgtcagaag acaatcgccc tttaactgga cttgcagctg caattgccgg agcaaaactt
1561  aggaaagtgt cacggatgga ggatacctct ttcccaagtg gagggaatgc tattggtgtg
1621  aactccgcct catctaaaac agatacaggc cgtgaaatg gacccctccc tttaggggt
1681  agtggtttaa tggaagaaat gagtgccctg ctggccagga ggagaagaat tgctgaaaag
1741  ggatcaacaa tagaaacaga acaaaaagag gacaaggtg aagattcaga gcctgtaact
1801  tctaaggcct cttcaacaag tacacctgaa ccaacaagaa aaccttggga aagaacaaat
1861  acaatgaatg gcagcaagtc acctgttatc tccagaccaa aatccacacc cttatcacag
1921  cccagtgcca atggagtcca gacggaagga cttgactatg acaggctgaa gcaggacatt
1981  ttagatgaaa tgagaaaaga attaacaaag ctaaagaag agctcattga tgcaatcagg
2041  caggaactga gcaagtcaaa tactgcatag aggaacagac taaggagaga taggacttta
2101  atctggagga aaaatatcct acaaacaaca actgttcaca acagcaaacc cctacattta
2161  tgagctgtaa gaagaaaatg gagacaaaca gaaggaggga aaaaccaacc tactctgaaa
2221  gccttcagac attatgactc tggtgataag ctctttccct ctccgtttgc tgcttttttc
2281  tggcctttac aacagaatgg aa
```

(SEQ ID NO: 4) Human MENA amino acid sequence (570 aa):
MSEQSICQARAAVMVYDDANKKWVPAGGSTGFSRVHIYHHTGNNTFRVVGRKIQDHQVVINCAIPKGLKYNQATQTF

HQWRDARQVYGLNFGSKEDANVFASAMMHALEVLNSQETGPTLPRQNSQLPAQVQNGPSQEELEIQRRQLQEQQRQK

-continued

```
ELERERLERERMERERLERERLERERLERERLERERLEQEQLERERQERERQERLERQERLERQERLDRERQERQE

RERLERLERERQERERQEQLEREQLEWERERRISSAAAPASVETPLNSVLGDSSASEPGLQAASQPAETPSQQGIVL

GPLAPPPPPPLPPGPAQASVALPPPPGPPPPPPLPSTGPPPPPPPPPLPNQVPPPPPPPPAPPLPASGFFLASMSED

NRPLTGLAAAIAGAKLRKVSRMEDTSFPSGGNAIGVNSASSKTDTGRGNGPLPLGGSGLMEEMSALLARRRRIAEKG

STIETEQKEDKGEDSEPVTSKASSTSTPEPTRKPWERTNTMNGSKSPVISRPKSTPLSQPSANGVQTEGLDYDRLKQ

DILDEMRKELTKLKEELIDAIRQELSKSNTA
```

Provided herein are isolated, purified or enriched nucleic acid sequences, e.g., oligonucleotide probes. In certain embodiments, the probe is a nucleic acid probe is from 4 to 500 nucleotides in length. In certain embodiments, the probe is from 10 to 100 nucleotides. In still additional embodiments, the probe is from 15 to 20 nucleotides. In certain embodiments, the probe is at least 20 or 22 or 25, preferably less than 500 nucleotides in length, more preferably 200 or 100 or fewer, still more preferably 50 or fewer, and most preferably 30 or fewer. In preferred embodiments, the probe has a length in a range from any one of the above lengths to any other of the above lengths (including endpoints). The probe specifically hybridizes under selective hybridization conditions to a nucleic acid sequence corresponding to a portion of one of the genes identified in connection with above aspects. The nucleic acid sequence includes at least one and or more variant sites. In any of the aspects or embodiments, the nucleic acid sequence can be a probe, a primer or amplification oligonucleotide that is able to bind to the target gene, for example: Lpd and/or MENA.

Also in preferred embodiments, the probe has a detectable label, preferably a fluorescent label. A variety of other detectable labels are known to those skilled in the art. Such a nucleic acid probe can also include one or more nucleic acid analogs.

In certain embodiments, an oligonucleotide may be an oligoribonucleotide, oligodeoxyribonucleotide, modified oligoribonucleotide or modified oligo-deoxyribonucleotide. In certain embodiments, the oligonucleotide consists of ribonucleotides, deoxyribonucleotides or a combination thereof, with the 5'-end of one nucleotide and the 3'-end of another nucleotide being linked to one another by a phosphodiester bond. These oligonucleotides may be synthesized in the conventional manner or produced recombinantly.

In certain embodiments, the oligonucleotide is a "modified" oligonucleotide. Here, the oligonucleotide may be modified in very different ways, without impairing its ability to bind its target, in order to increase, for example, its stability. According to the invention, the term "modified oligonucleotide" means an oligonucleotide in which (i) at least two of its nucleotides are linked to one another by a synthetic internucleoside bond (i.e. an internucleoside bond which is not a phosphodiester bond) and/or (ii) a chemical group which is usually not found in nucleic acids is covalently linked to the oligonucleotide. Preferred synthetic internucleoside bonds are phosphorothioates, alkyl phosphonates, phosphorodithioates, phosphate esters, alkyl phosphonothioates, phosphoramidates, carbamates, carbonates, phosphate triesters, acetamidates, carboxymethyl esters and peptides.

The term "modified oligonucleotide" also comprises oligonucleotides having one or more covalently modified bases and/or one or more covalently modified sugars. "Modified oligonucleotides" comprise, for example, oligonucleotides with sugar residues which are covalently bound to low molecular weight organic groups other than a hydroxyl group at the 3'-position and a phosphate group at the 5'-position. Modified oligonucleotides may comprise, for example, a 2'-O-alkylated ribose residue or another sugar instead of ribose, such as arabinose.

The nucleic acids suitable for use in the methods as described herein are preferably isolated. For example, in certain embodiments the nucleic acid may be (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. In certain aspects the nucleic acid for detecting the Lpd gene or transcript is labeled with a detectable marker. Suitable labels are known in the art.

In an additional aspect, the description provides methods for diagnosing or prognosing metastatic cancer in a subject. In certain embodiments, the method comprises obtaining a biological sample from a subject; extracting total RNA or protein or both from the sample; determining the amount of Lamellipodin (Lpd) protein or gene expression level or both in the sample by contacting the sample with at least one of i) a nucleic acid capable of hybridizing specifically to an Lpd-encoding nucleic acid; ii) an anti-Lpd antibody or Lpd-binding polypeptide capable of binding specifically to Lpd protein; and correlating the amount of Lpd protein or gene expression level or both to the metastatic state or capacity of cells in the sample, wherein an enhanced amount of Lpd protein or upregulated gene expression of Lpd is indicative of a metastatic cancer or a cancer at risk of becoming metastatic.

In certain embodiments, the detection and/or measuring of Lpd protein is performed by detecting the amount of binding of an anti-Lpd antibody to Lpd protein as mentioned above. In certain other embodiments, the detection and/or measuring of Lpd gene expression is performed by hybridizing a nucleic acid probe, e.g., labeled probe, to a nucleic acid that encodes a Lpd protein or portion thereof. In certain aspects, the nucleic acid is an Lpd-encoding mRNA or portion thereof. In certain aspects, the nucleic acid is an Lpd-encoding cDNA or portion thereof.

In another aspect, the description provides methods for diagnosing or prognosing metastatic cancer in a subject. In embodiments, the method comprises obtaining a biological sample from a subject; extracting total RNA or protein or both from the sample; determining the amount of Lamellipodin (Lpd) protein or expression level or both in the sample by contacting the sample with at least one of i) a nucleic acid capable of hybridizing specifically to an Lpd-encoding nucleic acid; ii) an anti-Lpd antibody or Lpd-binding polypeptide capable of binding specifically to Lpd protein; correlating the amount of Lpd protein or expression level or both to the metastatic state or capacity of cells in the sample, wherein an enhanced amount of Lpd protein or upregulated expression of Lpd is indicative of a metastatic cancer or a cancer at risk of becoming metastatic; and administering a therapeutic to a subject diagnosed as having metastatic cancer or at risk of developing metastatic cancer.

In any of the aspects or embodiments described herein, the method may further comprise the step of administering a therapeutic or therapeutic intervention (e.g., surgery) to the subject.

In any of the aspects or embodiments described herein, the method may include a step of fixing and labeling a biological sample, e.g., cell or tissue, with an agent as described herein. It is generally known in the art to fix, for example, by formalin, paraffin-embedded tissue for staining by nucleic acid hybridization or immunofluorescence labeling. As such, and as would be appreciated by the skilled artisan, the description encompasses any suitable method that is known or becomes known.

For example, preparation of the sample is critical to maintain cell morphology, tissue architecture and the antigenicity of target epitopes. This requires proper tissue collection, fixation and sectioning. A solution of paraformaldehyde is often used to fix tissue, but other methods may be used. The tissue may then be sliced or used whole, dependent upon the purpose of the experiment or the tissue itself. Before sectioning, the tissue sample may be embedded in a medium, like paraffin wax or cryomedia. Sections can be sliced on a variety of instruments, most commonly a microtome or cryostat, and are sliced at a range of 4-40 µm. The slices are then mounted on slides, dehydrated using alcohol washes of increasing concentrations (e.g., 50%, 75%, 90%, 95%, 100%), and cleared using a detergent like xylene before being imaged under a microscope.

Depending on the method of fixation and tissue preservation, the sample may require additional steps to make the epitopes available for antibody binding, including deparaffinization and antigen retrieval. For formalin-fixed paraffin-embedded tissues, antigen-retrieval is often necessary, and involves pre-treating the sections with heat or protease. These steps may make the difference between the target antigens staining or not staining.

Dependent on the tissue type and the method of antigen detection, endogenous biotin or enzymes may need to be blocked or quenched, respectively, prior to antibody staining. Although antibodies show preferential avidity for specific epitopes, they may partially or weakly bind to sites on nonspecific proteins (also called reactive sites) that are similar to the cognate binding sites on the target antigen. A great amount of non-specific binding causes high background staining which will mask the detection of the target antigen. To reduce background staining samples are incubated with a buffer that blocks the reactive sites to which the primary or secondary antibodies may otherwise bind. Common blocking buffers include normal serum, non-fat dry milk, BSA, or gelatin. Commercial blocking buffers with proprietary formulations are available for greater efficiency. Methods to eliminate background staining include dilution of the primary or secondary antibodies, changing the time or temperature of incubation, and using a different detection system or different primary antibody. Quality control should as a minimum include a tissue known to express the antigen as a positive control, and negative controls of tissue known not to express the antigen, as well as the test tissue probed in the same way with omission of the primary antibody (or better, absorption of the primary antibody).

In another aspect, the description provides methods of treating a subject at risk of or having metastatic cancer comprising correlating the amount of Lpd protein or gene expression level or both in a biological sample from a subject to the metastatic state or capacity of cells in the sample, wherein an enhanced amount of Lpd protein or upregulated expression of Lpd relative to the control is indicative of a metastatic cancer or a cancer at risk of becoming metastatic; and administering a therapeutic course to a subject having metastatic cancer or being at risk of developing metastatic cancer.

In another aspect, the description provides methods of treating a subject at risk of or having metastatic cancer comprising obtaining a biological sample from a subject; determining the amount of Lamellipodin (Lpd) protein or expression level or both in the sample; comparing the amount of Lpd protein or expression level or both in the sample with that of a control; correlating the amount of Lpd protein or expression level or both to the metastatic state or capacity of cells in the sample, wherein an enhanced amount of Lpd protein or upregulated expression of Lpd relative to the control is indicative of a metastatic cancer or a cancer at risk of becoming metastatic; and administering a therapeutic course to a subject having metastatic cancer or being at risk of developing metastatic cancer.

In any of the above mentioned aspects or embodiments, the method may further comprise a step of detecting and measuring the amount of Mena protein and its isoforms or expression level, wherein enhanced amount of Mena protein or gene expression is further indicative of a metastatic cancer or cancer at risk of becoming metastatic.

Additionally, other antibodies may be used in combination with the antibodies of the present invention to provide further information concerning metastatic disease state. For example, tyrosine phosphorylation specific antibodies because Lpd gets phosphorylated to make active complexes for cell invasion and hence metastasis.

Therapeutic Agents

The description provides therapeutic compositions for ameliorating or reducing symptoms and/or progression of metastatic cancer. It is observed that Abl-mediated Lamellipodin phosphorylation promotes its association with both Scar/WAVE and Ena/VASP, while Src-dependent phosphorylation enhances binding to SCAR/WAVE but not Ena/VASP. Increased Lamellipodin levels enhance Ena/VASP and Scar/WAVE activities at the plasma membrane to promote 3D invasion and metastasis. With this knowledge and understanding, in certain embodiments, the description provides methods of administering an effective amount of a therapeutic agent to treat or ameliorate the effects of cancer, e.g., metastatic breast cancer. In certain aspects, the therapeutic agent can be a phosphorylation or a kinase inhibitor in various embodiments. In another embodiment, the therapeutic agent can be Abl and/or Src tyrosine kinase inhibitor. In an embodiment, the therapeutic agent can be an inhibitor of Lpd wherein, the inhibitor of Lpd is an antibody, an antibody fragment, a small organic molecule of less than 2000 daltons. Alternatively the agent may decrease Lpd protein activity by acting as an antagonist. In other embodiments, the agent may inhibit the enzymes or other molecules in the Lpd protein synthetic pathway.

The present description includes compositions prepared for storage or administration which include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985) hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

An effective amount, pharmaceutically effective dose, therapeutically effective amount, or pharmaceutically effective amount is that dose required to prevent, inhibit the occurrence, or treat (alleviate a symptom to some extent, preferably all of the symptoms) of a disease state or pathological condition. The effective amount depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 1000 mg/kg body weight/day of active ingredients is administered dependent upon potency of the negatively charged polymer. In addition, effective amounts of the compositions of the invention encompass those amounts utilized in the examples to facilitate the intended or desired biological effect.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In certain embodiments, the therapeutic agent includes a nucleic acid, an antibody or a protein. In other embodiments therapeutic agent is a nucleic acid, e.g., RNA, cDNA, PNA, complementary to a Lpd-encoding nucleic acid. For example, in an embodiment, the therapeutic agent is an RNA. Alternatively the agent may bind to mRNA encoding Lpd protein in such a manner as to inhibit mRNA expression and hence decrease in the amount of Lpd protein, such agent may include siRNA, miRNA, shRNA, CRISPR gRNA or combination thereof. In some aspects, siRNA, shRNA, miRNA or nucleic acid fragments that can inhibit the expression of Lpd by inhibiting the activity of Lpd encoding gene or nucleic can be use as medicament for the prevention or treatment of metastatic cancer in particular, breast cancer.

As used herein, the term "RNA" means a molecule comprising at least one ribonucleotide residue. By "ribonucleotide" is meant a nucleotide with a hydroxyl group at the 2'-position of a beta-D-ribo-furanose moiety. The term includes double stranded RNA, single stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

As used herein, the terms "complementarity" or "complementary" means that a nucleic acid can form hydrogen bond(s) with another nucleic acid sequence by either traditional Watson-Crick or other non-traditional types of interaction. In reference to the nucleic molecules of the present invention, the binding free energy for a nucleic acid molecule with its complementary sequence is sufficient to allow the relevant function of the nucleic acid to proceed, e.g., RNAi activity. For example, the degree of complementarity between the sense and antisense strand of the siRNA construct can be the same or different from the degree of complementarity between the antisense strand of the siRNA and the target RNA sequence. A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence.

By "small interfering RNA" or "siRNA" as used herein is meant an isolated RNA molecule, preferably greater than 10 nucleotides in length, more preferably greater than 15 nucleotides in length, and most preferably 18, 19, 20, 21, 22, 23, 24, 25, 26, 27, 28, 29, or 30 nucleotides in length that is used to identify a target gene or mRNA to be degraded. A range of 19-25 nucleotides is the most preferred size for siRNAs.

The siRNA of the invention can comprise partially purified RNA, substantially pure RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA; modifications that make the siRNA resistant to nuclease digestion (e.g., the use of 2'-substituted ribonucleotides or modifications to the sugar-phosphate backbone); or the substitution of one or more nucleotides in the siRNA with deoxyribonucleotides. Furthermore, siRNA may be modified to increase the stability thereof as described above for modified oligonucleotides, in particular by introducing one or more phosphorothioate linkages (US 2012/0165390 A1 herein incorporated by reference in its entirety).

One or both strands of the siRNA of the invention can also comprise a 3'-overhang. As used herein, a "3'-overhang" refers to at least one unpaired nucleotide extending from the 3'-end of an RNA strand.

Thus in one embodiment, the siRNA of the invention comprises at least one 3'-overhang of from 1 to about 6 nucleotides (which includes ribonucleotides or deoxynucleotides) in length, preferably from 1 to about nucleotides in length, more preferably from 1 to about 4 nucleotides in length, and particularly preferably from about 2 to about 4 nucleotides in length.

In the embodiment in which both strands of the siRNA molecule comprise a 3'-overhang, the length of the overhangs can be the same or different for each strand. In a most preferred embodiment, the 3'-overhang is present on both strands of the siRNA, and is 2 nucleotides in length. For example, each strand of the siRNA of the invention can comprise 3'-overhangs of dideoxythymidylic acid ("TT") or diuridylic acid ("uu").

In order to enhance the stability of the present siRNA, the 3'-overhangs can be also stabilized against degradation. In one embodiment, the overhangs are stabilized by including purine nucleotides, such as adenosine or guanosine nucleotides. Alternatively, substitution of pyrimidine nucleotides by modified analogues, e.g., substitution of uridine nucleotides in the 3'-overhangs with 2'-deoxythymidine, is tolerated and does not affect the efficiency of RNAi degradation. In particular, the absence of a 2'-hydroxyl in the 2'-deoxythymidine significantly enhances the nuclease resistance of the 3'-overhang in tissue culture medium.

The sense and antisense strands of the present siRNA can comprise two complementary, single-stranded RNA molecules or can comprise a single molecule in which two complementary portions are base-paired and are covalently linked by a single-stranded "hairpin" area. That is, the sense region and antisense region can be covalently connected via a linker molecule. The linker molecule can be a polynucleotide or non-nucleotide linker. Without wishing to be bound by any theory, it is believed that the hairpin area of the latter type of siRNA molecule is cleaved intracellularly by the "Dicer" protein (or its equivalent) to form a siRNA of two individual base-paired RNA molecules.

As used herein, "target mRNA" refers to an RNA molecule that is a target for downregulation, in particular human Lpd mRNA, or mRNA from cognate Lpd or RAPH1 genes. The Lpd mRNA described herein as the cDNA equivalent. One skilled in the art would understand that the cDNA sequence is equivalent to the mRNA sequence, and can be used for the same purpose herein. siRNA or shRNA can be used as a therapeutic agent by inhibiting the expression of Lpd which will result in inhibition of metastasis.

The Peptide Nucleic Acid (PNA) described herein, is a powerful biomolecular tool that mimics the behavior of DNA with a pseudopeptide backbone and binds with complementary nucleic acid strands. PNA is an extremely good structural mimic of DNA (or RNA), and PNA oligomers are able to form very stable duplex structures with Watson-Crick complementary DNA, RNA (or PNA) oligomers, and they can also bind to targets in duplex DNA by helix invasion. Alternatively the agent may bind to a nucleic sequence encoding Lpd protein in such a manner that it leads to a decrease in the amount of transcribed mRNA encoding the polypeptide. For instance the agent may bind to coding or non-coding regions of the gene, or mRNA or to DNA 5' or 3' of the gene and thereby decreases expression of the protein. For example, in the description Lpd-targeting shRNAs generated Lpd knockdown tumor models. Lpd-deficient tumors were unable to develop metastases.

As used herein, a gene or mRNA which is "cognate" to human Lpd is a gene or mRNA from another mammalian species which is homologous to human Lpd in particular, rat Lpd.

It is understood that Lpd mRNA contains target sequences for Lpd protein and siRNA can induce RNAi-mediated degradation of mRNA to inhibit the gene expression.

"Reduce" or "inhibit" as used herein means the ability to cause an overall decrease, preferably of 20% or greater, more preferably of 50% or greater, and most preferably of 75% or greater, in the level, e.g. in the level of protein or mRNA as compared to a reference sample (e.g., a sample not treated with siRNA). This reduction or inhibition of RNA or protein expression can occur through targeted mRNA cleavage or degradation. Assays for protein expression or nucleic acid expression are known in the art and include, for example, ELISA, western blot analysis for protein expression, and northern blotting or RNase protection assays for RNA.

siRNA can be expressed from pol III expression vectors without a change in targeting site, as expression of RNAs from pol III promoters is only believed to be efficient when the first transcribed nucleotide is a purine.

The siRNA of the invention can be targeted to any stretch of approximately 19-25 contiguous nucleotides in any of the target mRNA sequences (the "target sequence"). Techniques for selecting target sequences for siRNA are given, for example, in Tuschl T. et al., "The siRNA User Guide", revised Oct. 11, 2002, the entire disclosure of which is herein incorporated by reference. "The siRNA User Guide" is available on the world wide web at a website maintained by Dr. Thomas Tuschl, Laboratory of RNA Molecular Biology, Rockefeller University, New York, USA, and can be found by accessing the website of the Rockefeller University and searching with the keyword "siRNA". Thus, the sense strand of the present siRNA comprises a nucleotide sequence substantially identical to any contiguous stretch of about 19 to about 25 nucleotides in the target mRNA.

Generally, a target sequence on the target mRNA can be selected from a given cDNA sequence corresponding to the target mRNA, preferably beginning 50 to 100 nt downstream (i.e., in the 3'-direction) from the start codon. The target sequence can, however, be located in the 5'- or 3'-untranslated regions, or in the region nearby the start codon.

RNA interference (RNAi) has rapidly become a powerful tool for gene silencing, drug discovery and target validation (Nishikura, K. 2001. Cell 107:415-418), and vectors that synthesize small hairpin (sh) RNA permit sustained gene silencing (Grimm, D. et al. 2007. Am. Soc. Hematol. Educ. Program 473-481). These vectors allow for the synthesis of 50 base pair (bp)-long single stranded RNAs that fold in 21-23 bp dsRNA with a small hairpin in the middle, and that are subsequently processed to siRNAs by the cellular machinery. These shRNA expression vectors can be engineered to contain selectable markers to generate stable transfectants, to co-express reporter genes, and to be incorporated into viral vectors such a lentiviral vector (Hannon, G. J. et al. 2004. Methods Mol. Biol. 257:255-266). This virus is modified to be non-replicative, and is efficiently transduced into human cells, including non-dividing cells (Hannon, G. J. et al. 2004. Methods Mol. Biol. 257:255-266; Amado, R. G. and I. S. Chen. 1999. Science 285:674-676). It then integrates into the host genome, resulting in long-term and stable expression of the shRNA (Sikorski, R. et al. 1998. Science 282:1438). Human shRNA as described herein (FIGS. 2-6), can completely knockdown the expression of Lpd and inhibit cancer metastasis, hence showing its potential as therapeutic agent.

Antisense oligonucleotides are single-stranded nucleic acids, which can specifically bind to a complementary nucleic acid sequence. By binding to the appropriate target sequence, an RNA-RNA, a DNA-DNA, or RNA-DNA duplex is formed. These nucleic acids are often termed "antisense" because they are complementary to the sense or coding strand of the gene. Recently, formation of a triple helix has proven possible where the oligonucleotide is bound to a DNA duplex. It was found that oligonucleotides could recognize sequences in the major groove of the DNA double helix. A triple helix was formed thereby. This suggests that it is possible to synthesize sequence-specific molecules which specifically bind double-stranded DNA via appropriate formation of major groove hydrogen bonds.

By binding to the target nucleic acid, the above oligonucleotides can inhibit the function of the target nucleic acid. This could, for example, be a result of blocking the transcription, processing, poly(A) addition, replication, translation, or promoting inhibitory mechanisms of the cells, such as promoting RNA degradations.

In certain embodiments the therapeutic agent can be at least one of cisplatin, cyclophosphamind, doxorubicin, prednisone, 5-FU, trastuzumab, docetaxel, 3G4, travacin, gemcitabine, phalloidin, cytochalasin D, latrunculin, jasplakinolide, swinholide, estramustine, carboplatin, prednisone, a HER2 or HER3 or HER2/3 antibody, trastuzumab, pertuzumab, neuvax, PI2K/AKT inhibitor, radioimmunotherapy agents, Aldesleukin, Alemtuzumab, Alitretinoin, Altretamine, Amifostine, Aminoglutethimide Anagrelide, Anastrozole, Arsenic Trioxide, Asparaginase, Azacitidine, 25 Azathioprine, Bendamustine, Bevacizumab, Bexarotine, Bicalutamide, Bleomycin, Bortezomib, Busulfan, Capecitabine, Carboplatin, Carmustine, Cetuximab, Chlorambucil, Cisplatin, Cladribine, Cyclophosphamide, Cytarabine, Dacarbazine, Dactinomycin, Dasatinib, Daunorubicin, Denileukin diftitox, Decitabine, Docetaxel, Dexamethasone, Doxifluridine, Doxorubicin, Epirubicin, Epoetin Alpha, Epothilone, Erlotinib, Estramustine, Etoposide, Everolimus, Exemestane, Filgrastim, Floxuridine, Fludarabine, Fluorouracil, Fluoxymesterone, Flutamide, Gefitinib, Gemcitabine, Gemtuzumab ozogamicin, Goserelin, Hexamethylmelamine, Hydroxyureas, Ibritumomab, Idarubicin, Ifosfamide, Imatinib, Interferon alpha, Interferon beta, Irinotecan, Ixabepilone, Lapatinib, Leucovorin, Leuprolide, Lenalidomide, Letrozole, Lomustine, Mechlorethamine, Megestrol, Melphalan, Mercaptopurine, Methotrexate, Mitomycin, Mitoxantrone, Nelarabine, Nilotinib, Nilutamide, Octreotide, Ofatumumab, Oprelvekin, Oxaliplatin, Paclitaxel, Panitumumab, Pemetrexed, Pentostatin, Procarbazine, Raloxifene, Retinoic acids, Rituximab, Romiplostim, Sargramostim, Sorafenib, Streptozocin, Sunitinib, Tamoxifen, Temsirolimus, Temozolamide, Teniposide, Thalidomide, Thioguanine, Thiotepa, Tioguanine, Topotecan, Toremifene, Tositumomab, Trastuzumab, Tretinoin, Valrubicin, VEGF inhibitors and traps, Vinblastine, Vincristine, Vindesine, Vinorelbine, Vorinostat, anti-immunomodulatory agent, anti-inflammatory agents, glucocorticoid, steroid, nonsteroidal anti-inflammatory drug, leukotreine antagonist, 13 2-agonist, anticholinergic agent, sulphasalazine, penicillamine, dapsone, antihistamines, anti-malarial agents, antiviral agents, antibiotic, or combinations thereof.

The therapeutic agents can be delivered by any route known to those of skill in the art. The formulations can be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a nucleic acid molecule of the invention and a pharmaceutically acceptable carrier. One or more nucleic acid molecules of the invention can be present in association with one or more non-toxic pharmaceutically acceptable carriers and/or diluents and/or adjuvants, and if desired other active ingredients. The pharmaceutical compositions of the invention can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present. Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Nucleic acid molecules as described herein can also be administered in the form of suppositories, e.g., for rectal administration of the drug or via a catheter directly to the bladder itself. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules as described herein can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle. The amount of active ingredient that can be combined with the carrier materials to produce a single dosage form varies depending upon the host treated and the particular mode of administration. Dosage unit forms generally contain between from about 1 mg to about 5000 mg of an active ingredient. It is understood that the specific dose level for any particular patient or subject depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water. The composition can also be administered to a subject in combination with other therapeutic compounds to increase the overall therapeutic effect. The use of multiple compounds to treat an indication can increase the beneficial effects while reducing the presence of side effects.

Alternatively, certain of the nucleic acid molecules as described herein can be expressed within cells from eukaryotic promoters (e.g., Izant and Weintraub, 1985, Science, 229, 345; McGarry and Lindquist, 1986, Proc. Natl. Acad. Sci., USA 83, 399; Scanlon et al., 1991, Proc. Natl. Acad. Sci. USA, 88, 10591 5; Kashani-Sabet et al., 1992, Antisense Res. Dev., 2, 3 15; Dropulic et al., 1992, J. Virol., 66, 1432 41; Weerasinghe et al., 1991, J. Virol., 65, 5531 4; Ojwang et al., 1992, Proc. Natl. Acad. Sci. USA, 89, 10802 6; Chen et al., 1992, Nucleic Acids Res., 20, 4581 9; Sarver et al., 1990 Science, 247, 1222 1225; Thompson et al, 1995, Nucleic Acids Res., 23, 2259; Good et al., 1997, Gene Therapy, 4, 45; all of these references are hereby incorporated in their totalities by reference herein). Those skilled in the art realize that any nucleic acid can be expressed in eukaryotic cells from the appropriate DNA/RNA vector.

In another aspect, the description provides an expression vector comprising a nucleic acid sequence encoding at least one of the nucleic acid molecules as described herein. The nucleic acid sequence encoding the nucleic acid molecule is operably linked in a manner which allows expression of that nucleic acid molecule.

Transcription of the nucleic acid molecule sequences are driven from a promoter for eukaryotic RNA polymerase I (pol I), RNA polymerase II (pol II), or RNA polymerase III (pol III). Transcripts from pol II or pol III promoters are expressed at high levels in all cells; the levels of a given pol II promoter in a given cell type depends on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990, Proc. Natl. Acad. Sci. USA, 87, 6743 7; Gao and Huang 1993, Nucleic Acids Res., 21, 2867 72; Lieber et al., 1993, Methods Enzymol., 217, 47 66; Zhou et al., 1990, Mol. Cell. Biol., 10, 4529 37). All of these references are incorporated by reference herein. Several investigators have demonstrated that nucleic acid molecules, such as ribozymes expressed from such promoters can function in mammalian cells (e.g. Kashani-Sabet et al., 1992, Antisense Res. Dev., 2, 3 15; Ojwang et al., 1992, Proc. Natl. Acad. Sci. USA, 89, 10802 6; Chen et al, 1992, Nucleic Acids Res., 20, 4581 9; Yu et al., 1993, Proc. Natl. Acad. Sci. USA, 90, 6340 4; L'Huillier et al., 1992, EMBO J., 11, 4411 8; Lisziewicz et al., 1993, Proc. Natl. Acad. Sci. U.S.A, 90, 8000 4; Thompson et al., 1995, Nucleic Acids Res., 23, 2259; Sullenger & Cech, 1993, Science, 262, 1566).

In another aspect the description features an expression vector comprising nucleic acid sequence encoding at least one of the nucleic acid molecules of the invention, in a manner which allows expression of that nucleic acid molecule. The expression vector comprises in one embodiment; a) a transcription initiation region; b) a transcription termination region; c) a nucleic acid sequence encoding at least one said nucleic acid molecule; and wherein said sequence is operably linked to said initiation region and said termination region, in a manner which allows expression and/or delivery of said nucleic acid molecule.

In an additional aspect, the description provides diagnostic kits for determining metastatic tumors comprising a container and including the components and agents needed to detect and measure the presence and amount of Lpd protein or Lpd expression in a biological sample according to a method as described herein.

In any of the aspects or embodiments described herein, the biological sample is a cell or a tissue. In certain embodiments, the cell or tissue is a cancer cell or cancerous tissue. In still additional embodiments, the cancer cell or cancerous tissue is a breast cancer cell or breast cancer tissue. In certain embodiments, the cells can be obtained from blood, plasma, serum mucus or any body fluids.

In aspects or embodiments, the cancer is one or more of breast, prostate, lung, colorectal, colon, rectal, head and neck, mesothelioma, ovarian, urothelial, hepatocellular, bladder, esophageal, stomach or any cancer that has metastatic capability.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXAMPLES

Example 1

Breast cancer metastasis is one of the leading causes of cancer-associated mortality in women worldwide (1). Metastasis is a multistep process (2). After breaching the basement membrane metastasizing cancer cells migrate through the dense extracellular matrix (ECM) of the tumor stroma in order to intravasate (2,3). Carcinoma cells that migrate in a mesenchymal mode form elongated membrane protrusions driven by the assembly of branched F-actin networks. Actin polymerization-driven migration and invasion is coordinated by the proto-oncogenes c-Src and c-Abl kinases and cytoskeletal regulatory proteins including Rac GTPase, the Scar/WAVE-complex, and Ena/VASP proteins (4-7). Ena/VASP proteins (Mena, EVL and VASP) enhance processive filament Elongation (8-14). Mena is up-regulated in breast cancer and promotes invasion (15,16). Lamellipodin (Lpd) has been identified as a binding partner of Ena/VASP proteins. Lpd localizes to lamellipodia, thin membrane protrusions at the leading edge of migrating cells (17). The Lpd-Ena/VASP interaction is positively regulated by Abl kinase-mediated Lpd phosphorylation, which drives Ena/VASP recruitment to lamellipodia by Lpd(19).

Lpd is required for lamellipodium formation and binds directly to the Scar/WAVE-complex (20). Scar/WAVE activates the Arp2/3 complex to nucleate branched actin networks during lamellipodia formation 4'. Surprisingly, Lpd-driven random cell migration in 2D requires Lpd binding to Scar/WAVE, but not to Ena/VASP.

The mechanisms by which actin regulators coordinate the interplay between actin-elongation and actin-branching factors to promote cancer cell invasion remain incompletely understood. In this invention, it has been found that Lamellipodin mediates invasive 3D migration of cancer cells via selective, regulated interactions with Ena/VASP and Scar/WAVE. These findings point to key roles for increased Lpd levels in breast cancer invasion and metastasis.

Figure 1D:
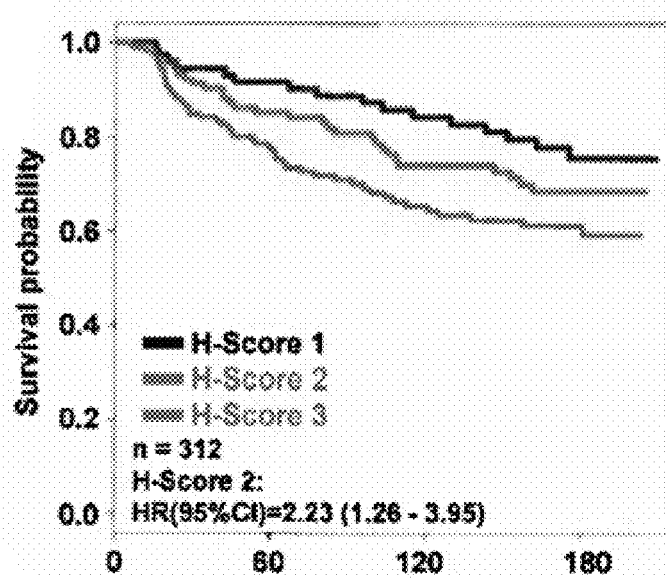
Figure 1G:
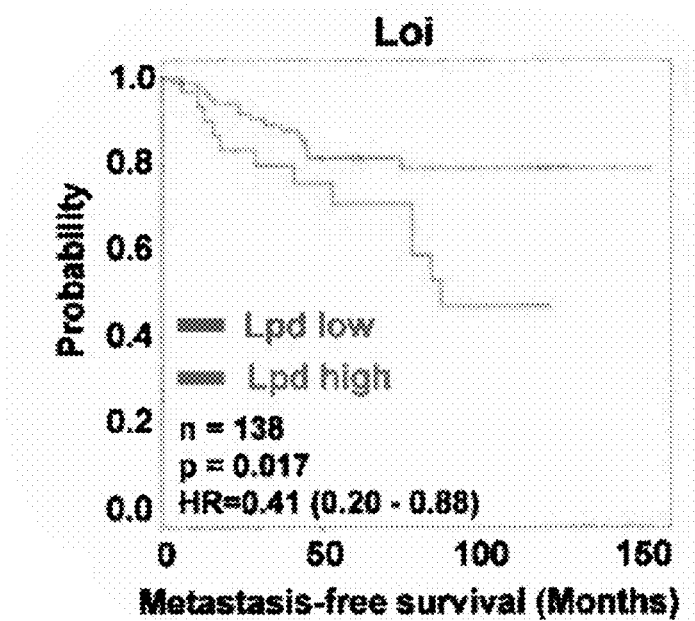
Figure 1H:
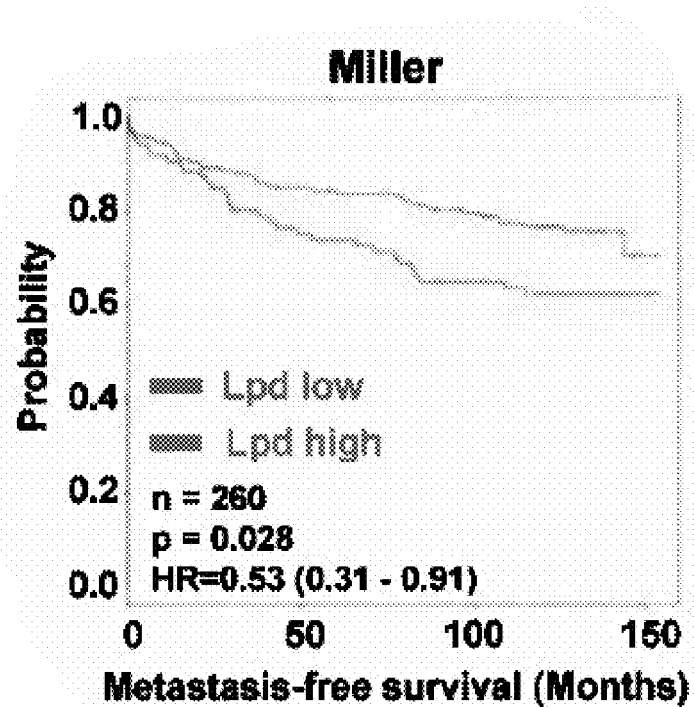
Figure 1I:
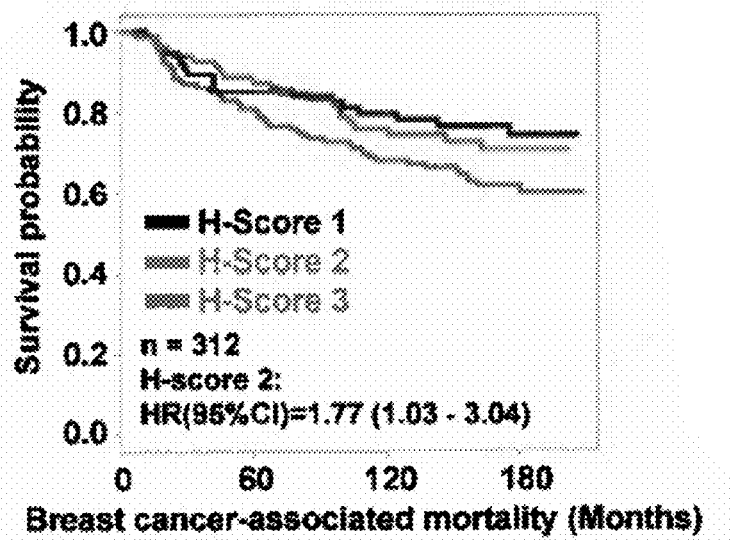
Figure 1J:
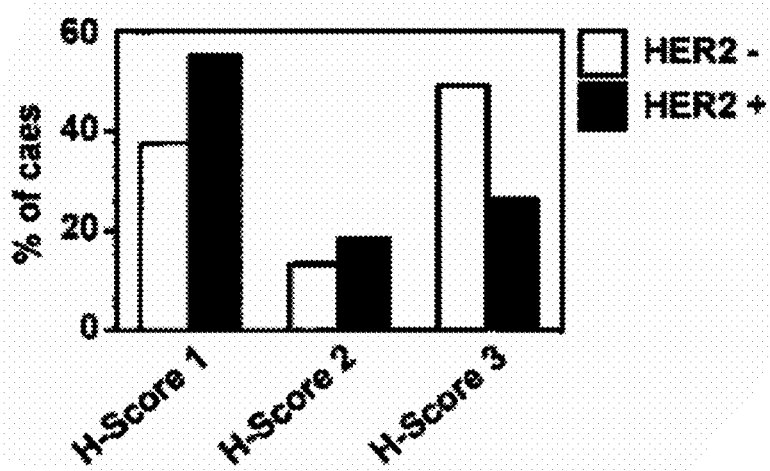
Figures 2A, 2B:
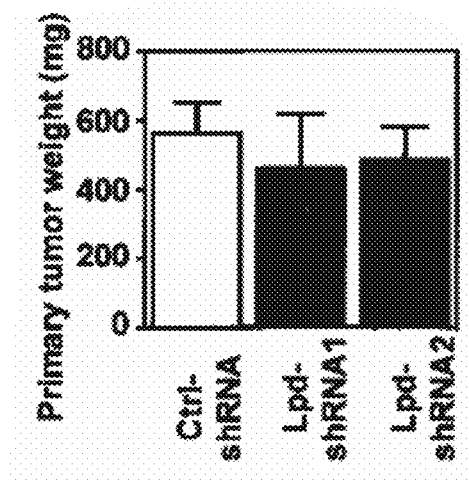
Figure 2:
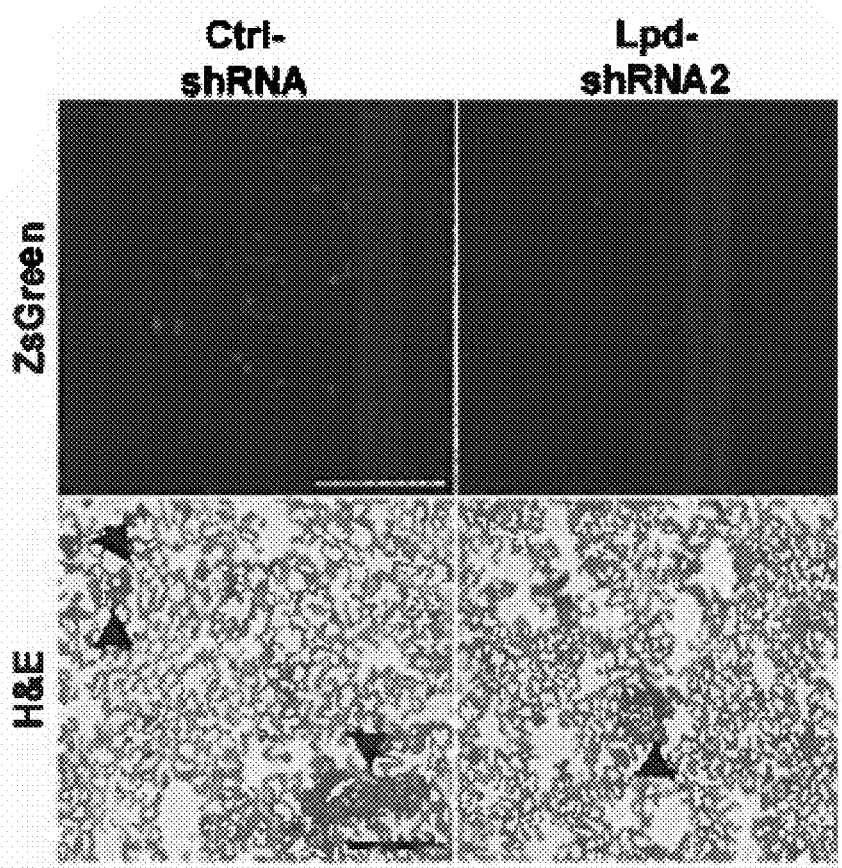

The higher Lpd levels were observed in invasive and metastatic basal cell lines compared to non-invasive, luminal tumor cell lines (FIG. 1A). Therefore, publicly available datasets were analyzed to examine whether Lpd mRNA levels correlated with occurrence of distant metastases in breast cancer patients. Lpd was over-expressed in several types of breast tumors compared to matched healthy tissue (FIG. 1F). High levels of Lpd mRNA correlated with reduced metastasis-free and disease-free survival of breast cancer patients in three separate cohorts (FIG. 1B, 1C, 1G, 1H). In addition, correlation of Lpd protein expression levels with clinical outcome for breast cancer patients was confirmed by staining a tumor microarray (TMA) generated from 312 patients with invasive breast cancer with anti-Lpd antibodies. Moderately, but not highly, increased abundance of Lpd in the cytoplasm (Histoscore 2; Hazard ratio (HR) (95% CI): 1.765 (1.026-3.036); FIGS. 1I and 2A, 2B) and at the plasma membrane (Histoscore 2: HR, (95% CD: 2.231 (1 0.26-3.949); FIG. 1D, 1E; compared to respective histoscores 1) were significantly associated with increased risk of breast cancer-associated mortality. Furthermore, an inverse correlation between Lpd intensity at the plasma membrane and Her2 expression was observed (FIG. 1J). Consistent with Lpd's predominant role at the plasma membrane in promoting cell motility and migration, a significant association between highly, but not moderately, increased Lpd staining intensity at the plasma membrane and reduced disease-free (Histoscore 3: HR (95% CD: 1.652 (1.24-2.428)) and metastasis-free survival of breast cancer patients (Histoscore 3: HR (95% CI): 1.515 (1.054-2.178); FIG. 1E compared to respective histoscores 1) was observed.

Figure 2D:
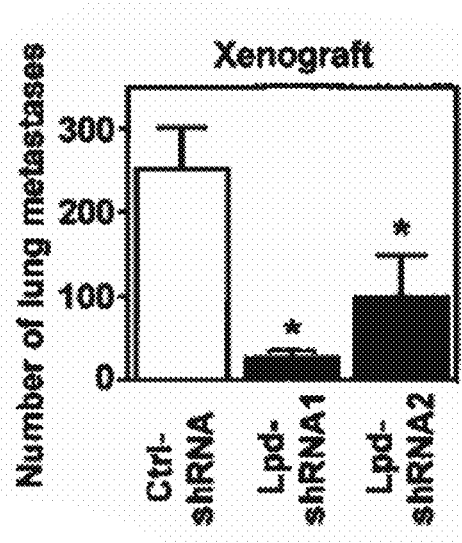
Figure 2E:
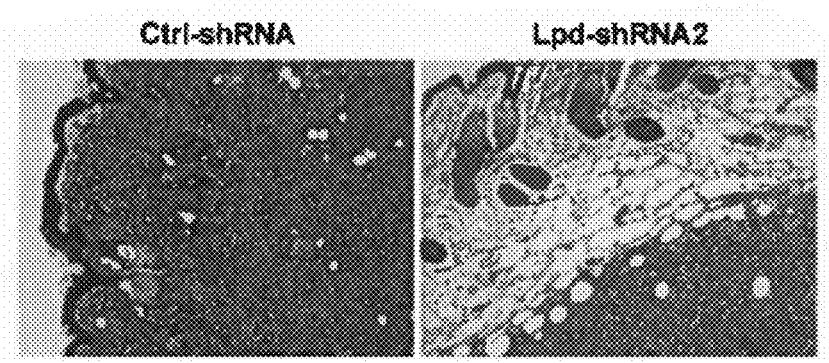
Figure 2F:
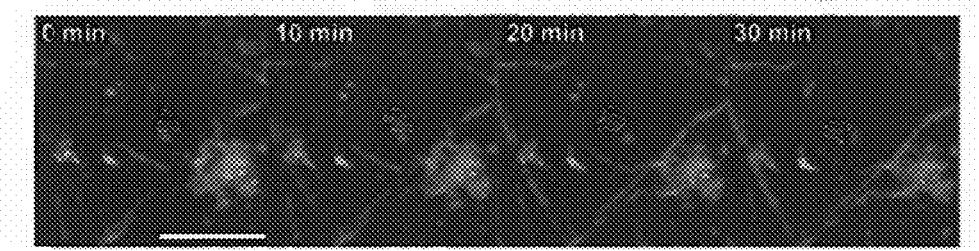
FIG. 2F-2I: Tumor cell motility in vivo monitored by multi-photon confocal imaging.
Figure 2G:
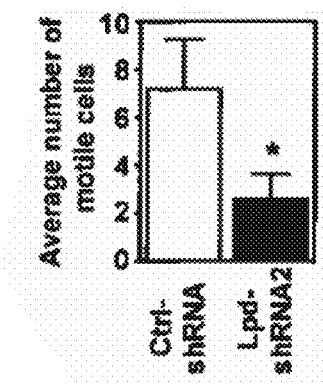
Figure 2H:
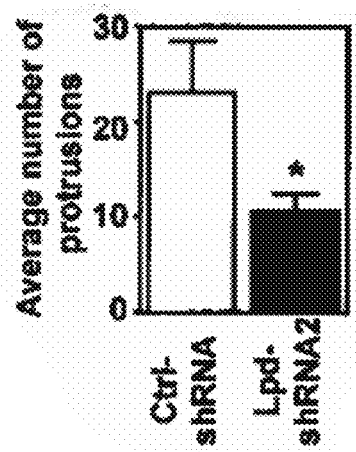
Figure 2I:
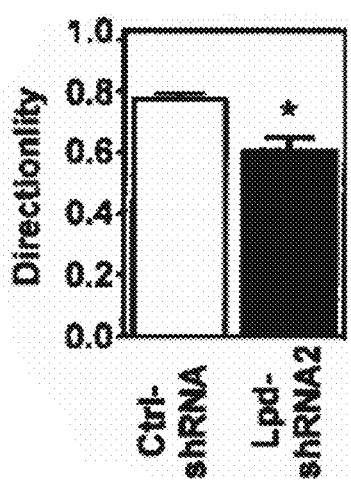
Figure 2J:
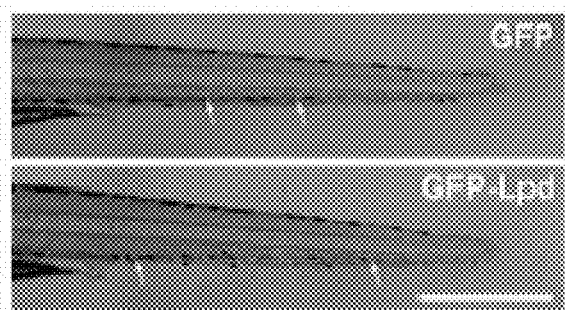
FIG. 2J-2K: Red fluorescently labeled MDA-MB-231 cells overexpressing GFP-Lpd or GFP as control were implanted into the perivitelline cavity of zebrafish embryos and dissemination to the trunk region quantified two days after injection.
Figure 2K:
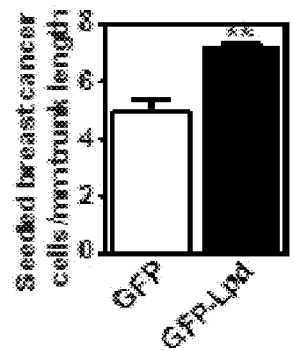
Figure 2L:
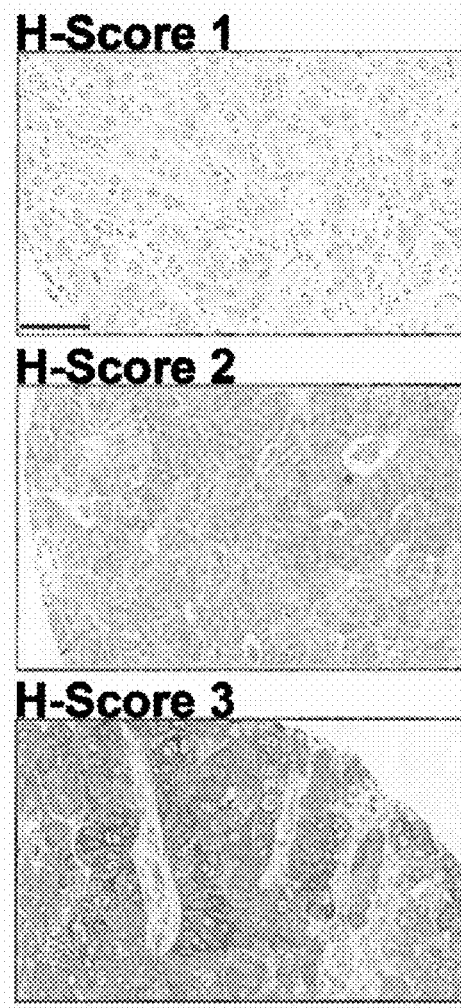
Figure 2N:
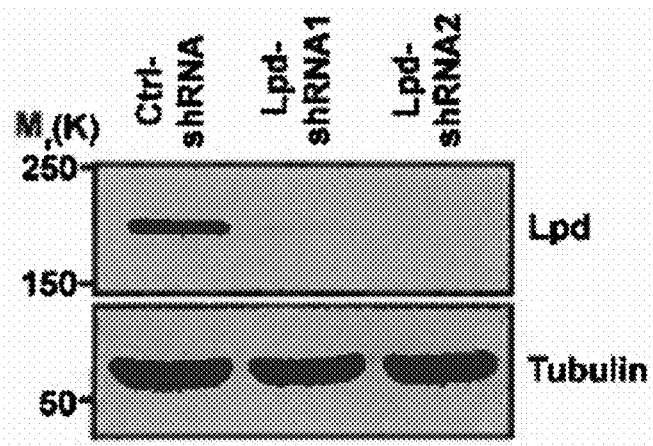

To investigate the requirement for Lpd in metastasis, the effect of reducing Lpd expression in MDA-MB-231-LM2 cells (further referred to as LM2), a highly metastatic derivative of MDA-MB-231 breast cancer cells 26, was tested on their ability to metastasize from an orthotopic mammary tumor to the lungs. Stable LM2 cell lines were generated with two independent Lpd-targeting shRNAs or a non-targeting control shRNA, all three retroviruses also conferring the cis-linked marker ZsGreen (FIG. 2N). Lpd knockdown and control cells were injected orthotopically into the mammary fat pad of immunodeficient mice. Primary tumors formed six weeks after injection from Lpd-deficient cells were similar in size to those arising from control LM2 cells, suggesting that loss of Lpd did not affect primary tumor growth (FIG. 2A). Importantly, only 3 out of 20 mice bearing Lpd-depleted tumors developed macroscopic lung metastases, compared to 9 out of 10 control tumor-bearing mice (FIG. 2B). In addition, animals with tumors generated from Lpd-depleted cells that metastasized displayed significantly reduced numbers of pulmonary ZsGreen-positive metastases compared to the metastatic burden of animals with control tumors (FIG. 2C, 2D). Role of Lpd in promoting cancer cell invasion during metastasis was explored. In fixed samples, tumors generated from control-shRNA LM2 cells, prominently invaded the surrounding stroma. However, tumors from Lpd knockdown cells were markedly less invasive (FIG. 2E). Function of Lpd in cancer invasion was investigated in more detail by intravital imaging. Compared to control-shRNA LM2 tumors, Lpd knockdown tumors had fewer motile cells, which migrated less directionally and extended protrusions less frequently (FIG. 2F, 2G, 2H, 2I), indicating that Lpd is required for invasive cancer cell phenotypes in vivo.

Figure 2O:
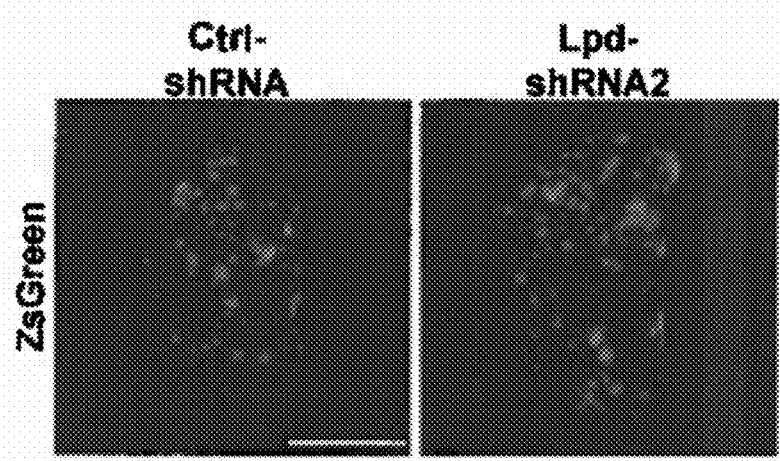
Figure 2P:
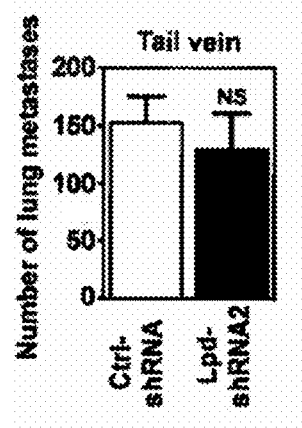

To examine Lpd-driven breast cancer intravasation and dissemination, fluorescently labeled MDA-MB-231 breast cancer cells were implanted into the perivitelline cavities of zebrafish embryos. In this assay, the injected cancers cells intravasate, and then infiltrate the trunk of the fish. Overexpression of GFP-Lpd in MDA-MB-231 cells enhanced the frequency of seeding of these breast cancer cells compared to GFP expressing control cells (FIG. 2J, 2K). Tail vein injections of the Lpd knockdown and control LM2 cell lines were injected into immunocompromised mice and quantification of lung metastasis was done after 28 days to test whether Lpd influenced the later stages of the metastatic cascade. Lpd depletion did not reduce the number of metastatic foci in the lungs of the mice compared to controls (FIG. 2O, 2P). Taken together, the results reveal that Lpd promotes local tumor invasion, intravasation, and metastasis in vivo, but is not required for extravasation.

Figure 3A:
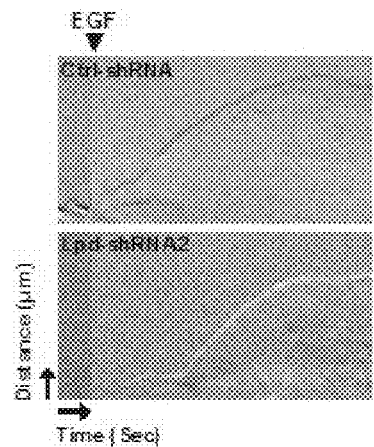
FIG. 3A-3K: Lpd is required for EGF-induced membrane-protrusion.
Figure 3B:
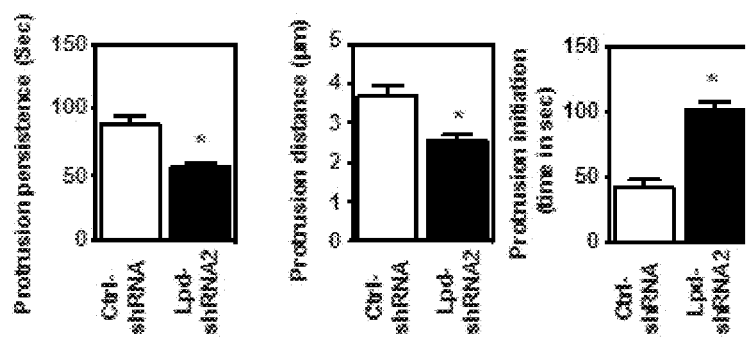
Figure 3C:
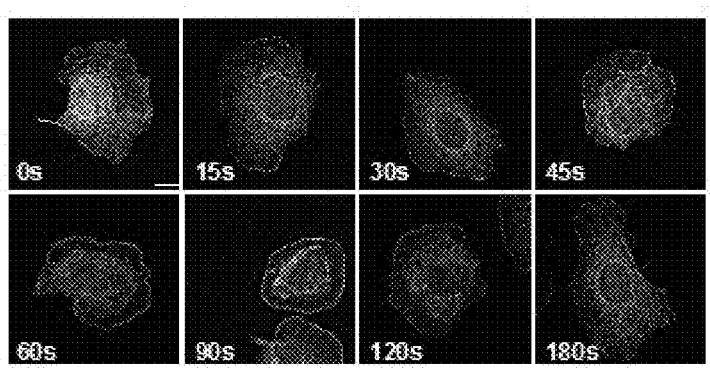
Figure 3D:
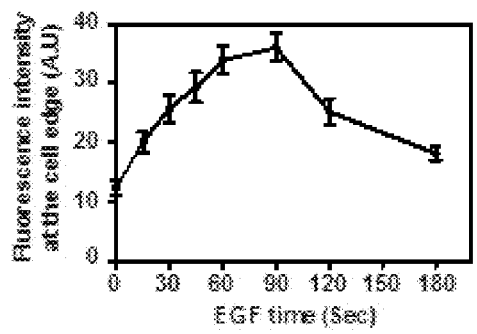
Figure 3E:
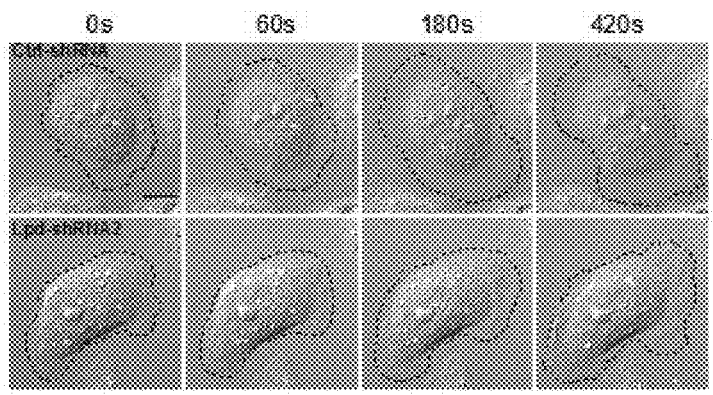
Figure 3F:
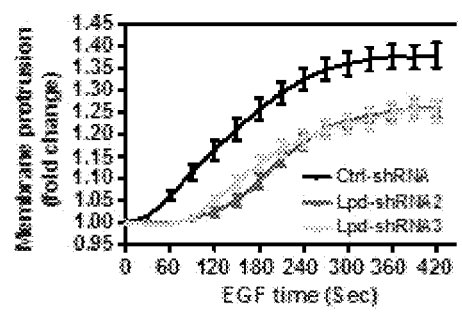
Figure 3G:
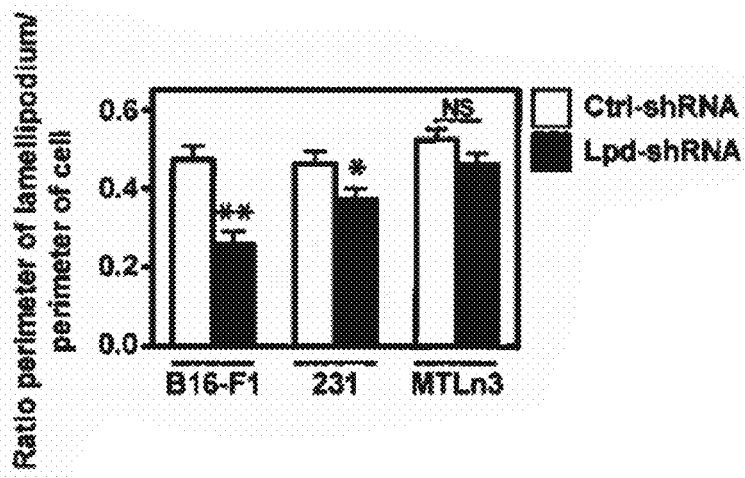
Figure 3H:
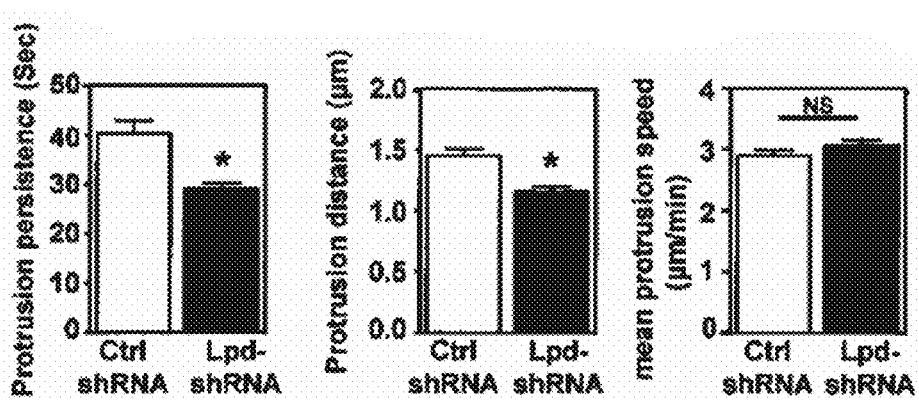
Figure 3I:
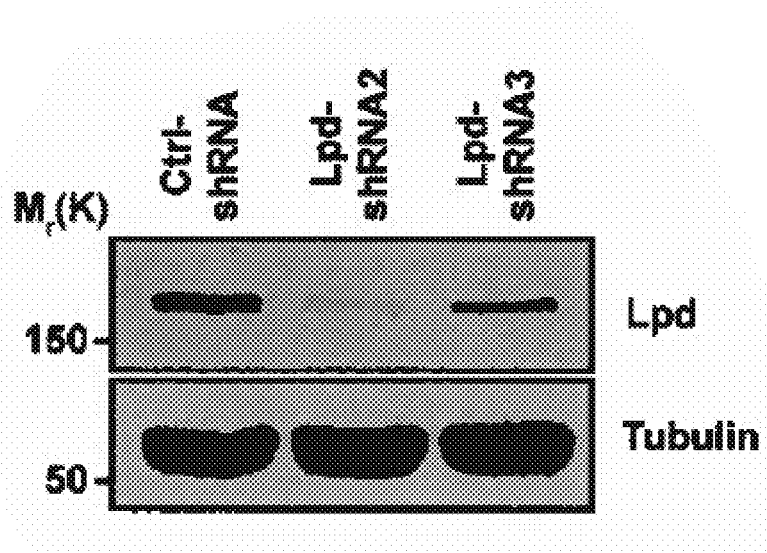
Figure 3J:
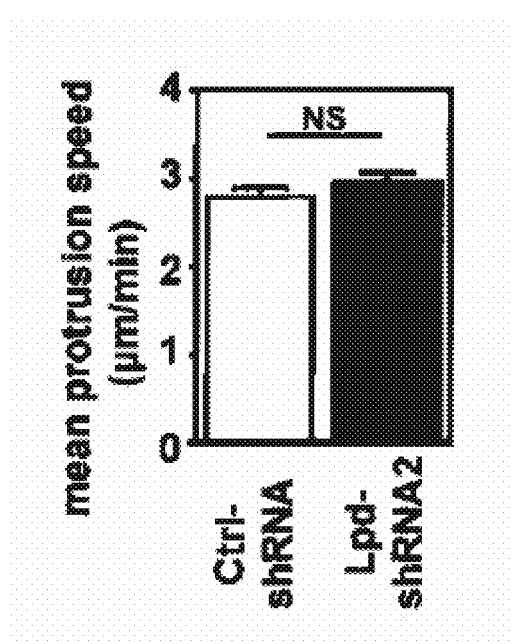
Figure 3K:
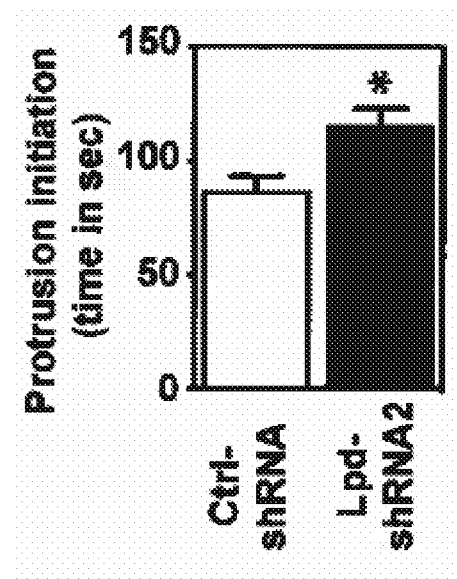
Figure 4A:
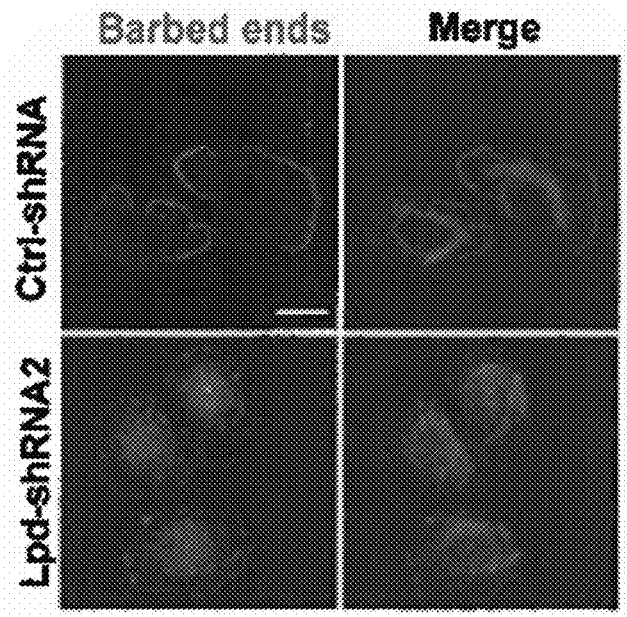
FIG. 4A-4L: Lpd is required for chemosensing.
Figure 4B:
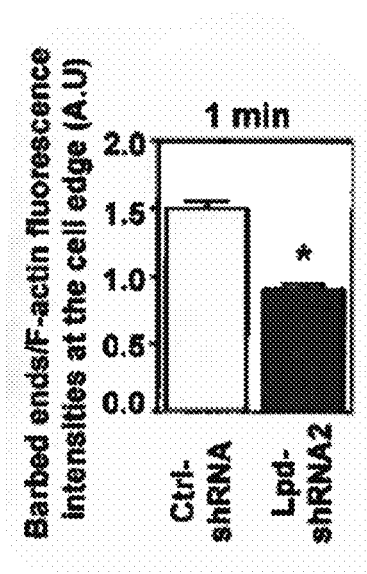
Figure 4C:
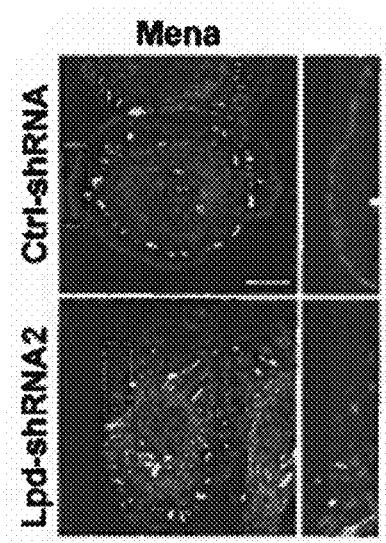
Figure 4D:
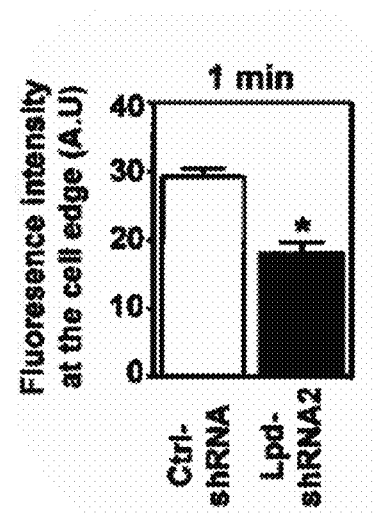
Figure 4E:
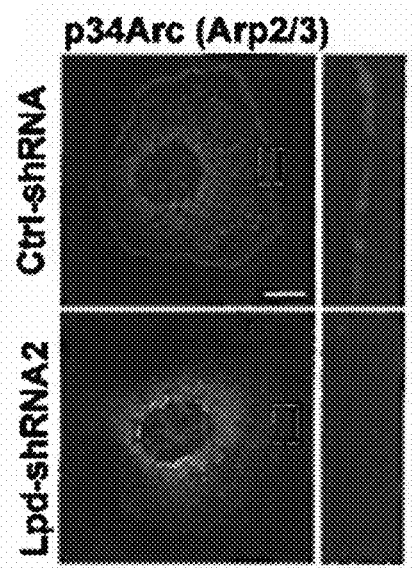
Figure 4F:
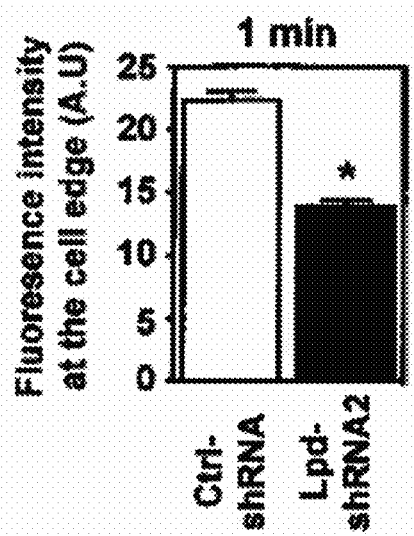
Figure 4G:
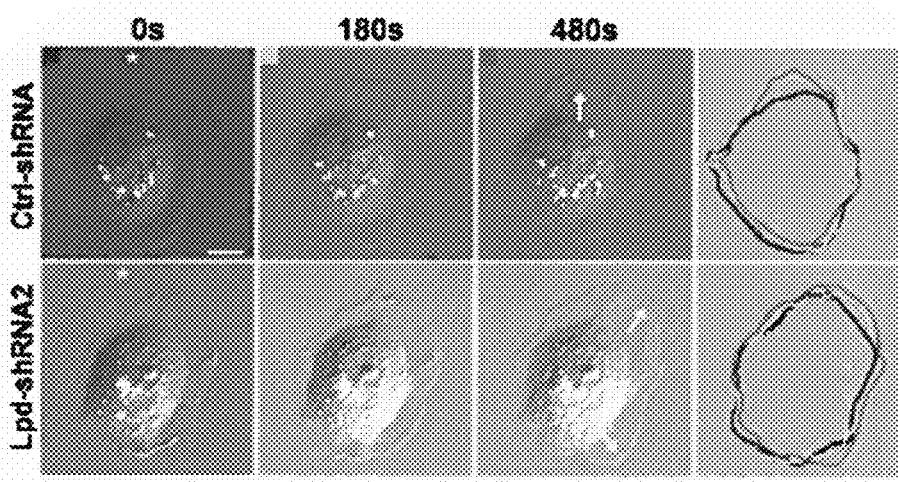
Figure 4H:
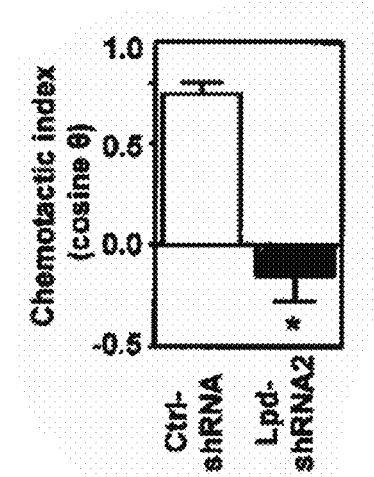

Breast cancer cell migration towards blood vessels is guided by cues from the tumor microenvironment, such as EGF. The effect of Lpd depletion on EGF-induced 3D invasion might arise from defects in lamellipodial dynamics. Depletion of Lpd in MDA-MB-231 breast cancer cells decreased lamellipodia size (FIG. 3G), similar to B16-F1 mouse melanoma cells, in which Lpd-depletion also reduces protrusion speed under steady state Conditions. EGF-stimulated MDA-MB-231Lpd knockdown cells displayed reduced protrusion persistence and distance, without affecting protrusion speed (FIG. 3H). MTLn3 cells, a mammary adenocarcinoma cancer cell line, was chosen in which protrusion responses to EGF have been extensively characterized, to examine EGF-elicited protrusion in more detail since lamellipodial size is least affected by Lpd knockdown in this cell line (FIG. 3G). In agreement with the findings in MDA-MB-231 cells, in EGF-stimulated MTLn3 cells reduced Lpd levels significantly decreased protrusion persistence and distance (FIG. 3A, 3B), but did not affect protrusion speed (FIG. 3J) compared to controls. Lpd was diffusely distributed throughout the cytoplasm of serum-starved cells, but was rapidly recruited to the cell edge following bath application of EGF (FIG. 3C, 3D). Lamellipodial initiation was detected 30 seconds after EGF stimulation in Ctrl-shRNA expressing cells, but was delayed significantly when Lpd levels were reduced (FIG. 3B, 3E, 3F; FIG. 3K). Taken together, the data suggests that in breast cancer cells, Lpd depletion reduces EGF-elicited lamellipodial protrusion formation and persistence, but not speed. Membrane extension during lamellipodial protrusion is driven by actin polymerization. To determine how Lpd depletion influences actin polymerization, a G-actin incorporation assay was performed to measure the abundance and distribution of polymerization-competent, free (uncapped) F-actin barbed-ends in lamellipodia of living cells. Silencing Lpd significantly reduced free barbed-end formation 1 minute after EGF stimulation, relative to Ctrl-shRNA-expressing cells (FIG. 4A, 4B).

Collectively, these data indicate that Lpd promotes lamellipodial protrusion by increasing actin polymerization downstream of EGFR activation. EGF-dependent membrane protrusion in MTLn3 cells requires Ena/VASP proteins and Arp2/3-mediated dendritic nucleation and Lpd binds both Ena/VASP proteins and the Arp2/3 activating Scar/WAVE-complex. Consistent with this, membrane recruitment of Mena (FIG. 4C, 4D) and Arp2/3 complex to the protruding edge (FIG. 4E, 4F) were significantly reduced in Lpd-depleted cells after EGF stimulation.

The requirement for Lpd in EGF-induced protrusion may reflect Lpd-mediated initiation of chemotactic responses. The initial step of chemotaxis is directional sensing. A micropipette was used to generate a spatially restricted EGF gradient. Ctrl-shRNA MTLn3 cells formed new protrusions towards the pipette, demonstrating their ability to sense the EGF gradient. However, those of Lpd-reduced cells were random relative to the micropipette (FIG. 4G, 4H, 4J, 4K). Chemotactic indices confirmed the lack of directional bias in Lpd-deficient MTLn3 protrusions (FIG. 4H), highlighting an essential role for Lpd in the initial steps of chemotaxis towards EGF. Lpd is concentrated at the edges of lamellipodia that protrude in response to uniform EGF stimulation. Correlative differential interference contrast microscopy and immunofluorescence imaging in live cells revealed enrichment of Lpd at the edges of cells oriented towards the micropipettes containing EGF (FIG. 4L), confirming that Lpd was enriched in membranes exposed to the highest concentration of the EGF gradient and supporting a function for Lpd in linking gradient-sensing to directed membrane protrusion.

Figure 4I:
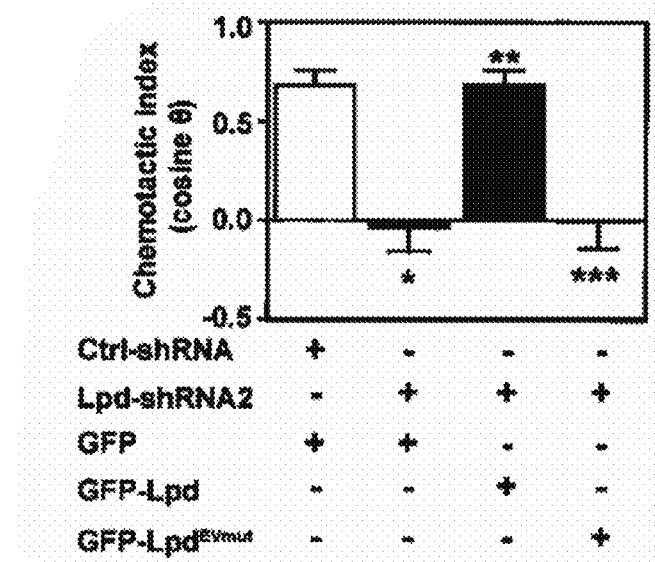
Figure 4J:
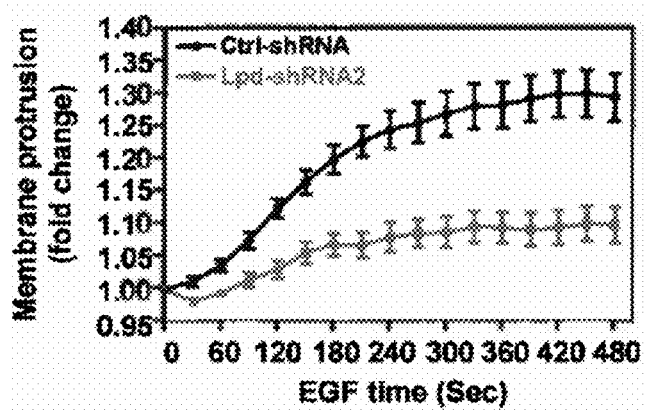
Figure 4K:
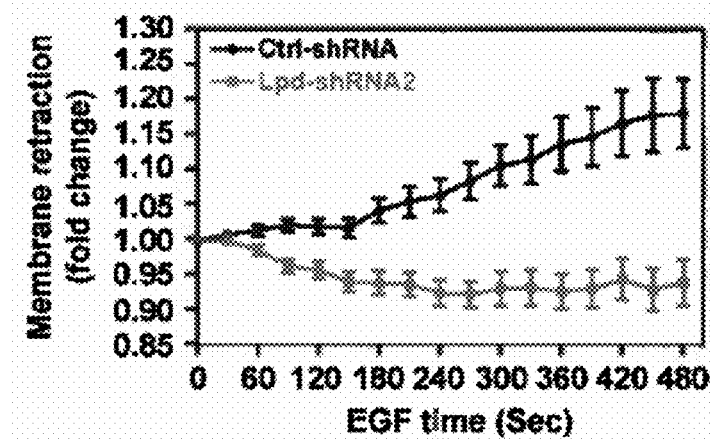
Figure 4L:
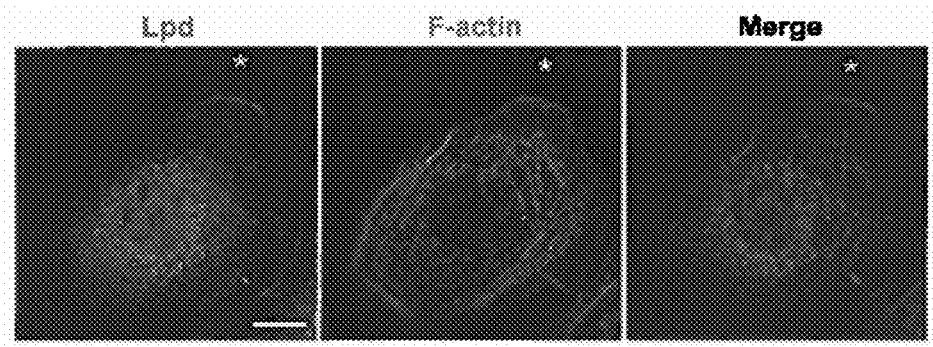
Figure 5A:
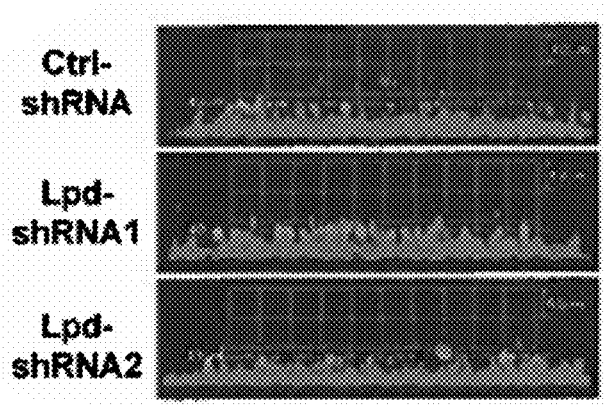
FIG. 5A-5M: Lpd is required for 3D-invasion of cancer cells.
Figure 5B:
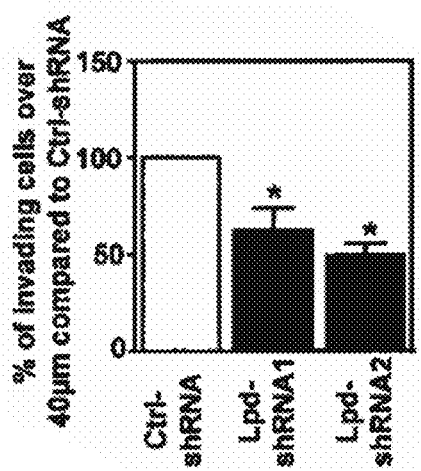
Figure 5C:
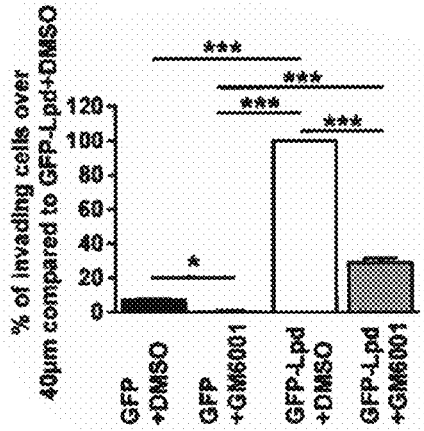
Figure 5D:
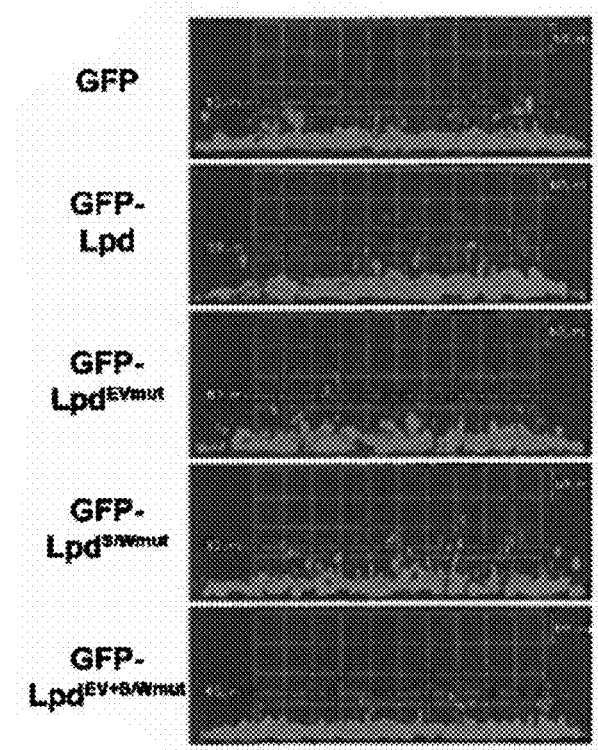
Figure 5E:
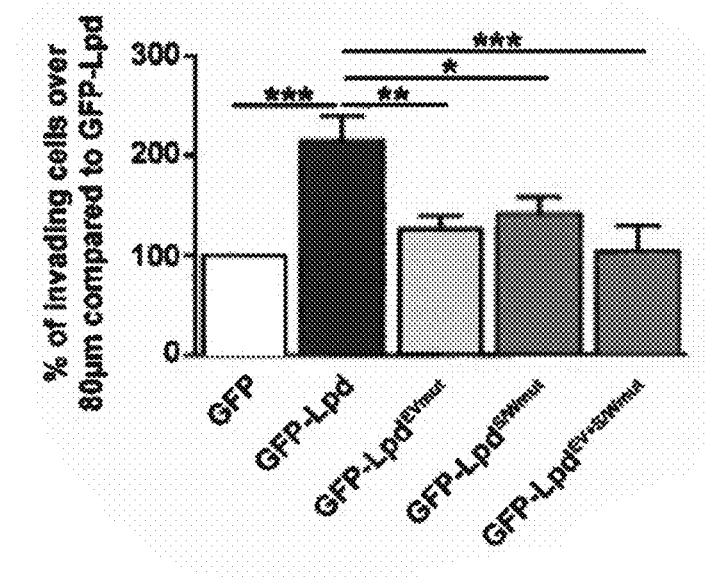
Figure 5F:
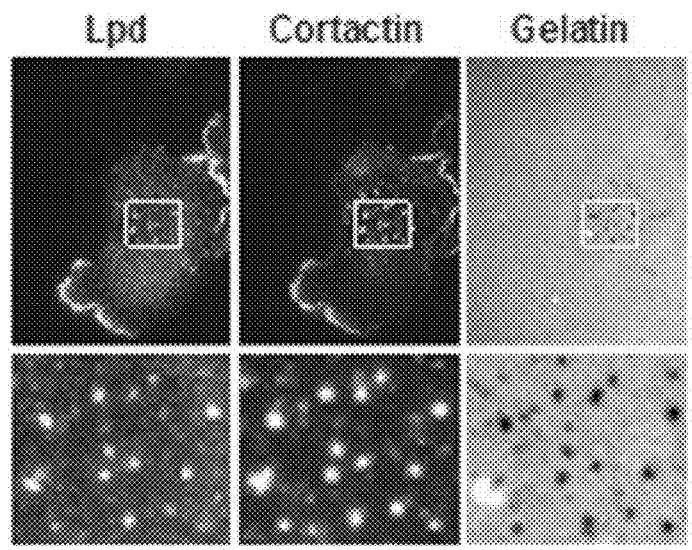

EGF chemosensing might involve Lpd-mediated recruitment of Ena/VASP proteins. It was tested whether Lpd-depleted cells, expressing either GFP-Lpd or an Lpd mutant in which all Ena/VASP binding sites had been rendered non-functional by mutation (GFP-Lpd$^{EVmut}$), could respond to EGF gradients in the micropipette assay and discovered that, while GFP-Lpd effectively rescued the chemosensing defects in Lpd-depleted cells, GFP-Lpd$^{EVmut}$ conferred no significant phenotypic rescue (FIGS. 4I and 5M). In line with this finding, a function-perturbing approach revealed that Ena/VASP proteins were required for chemosensing (FIGS. 5K and 5L). Thus, extension of lamellipodia towards EGF during chemosensing by breast carcinoma cells requires the Lpd-dependent recruitment of Ena/VASP proteins, despite the dispensability of Ena/VASP for Lpd driven random 2D cell migration.

The requirements for Lpd during EGF-dependent 3D invasion were analyzed. In 3D inverted chemotaxis assays towards EGF with MDA-MB-231 or SUM-159 invasive breast cancer lines knockdown of Lpd significantly decreased invasion through matrigel (FIG. 5A, 5B; FIG. 6H) and collagen (FIG. 6I, 6J, 6K) compared to control-shRNA expressing cells. Conversely, Lpd overexpression significantly increased invasion towards EGF (FIG. 5D, 5E).

Since invasion is known to be partially dependent on matrix metalloproteinase (MMP) digestion of ECM, it was tested whether Lpd increases invasion via MMP dependent or migration-dependent mechanisms. MMP inhibitor treatment of GEP expressing control cells reduced invasion, as expected. Similarly, MMP inhibitor treatment reduced invasion of Lpd overexpressing MDA-MB-231 cells. However, Lpd overexpressing cells treated with MMP inhibitors invaded significantly further compared to GFP control cells treated with the inhibitor suggesting that Lpd functions to increase invasion by increasing migration and potentially MMP-dependent ECM degradation (FIG. 5C and FIG. 6L). The aforementioned findings prompted the investigation of Lpd's role in MMP dependent degradation. Carcinoma cells can utilize protrusive invadopodia, sites of MMP exocytosis, to invade through the basement membrane and ECM-rich interstitial stroma. It was observed that Lpd co-localized with the invadopodial marker cortactin at invadopodia, at sites of matrix degradation (FIG. 5F).

Figure 5I:
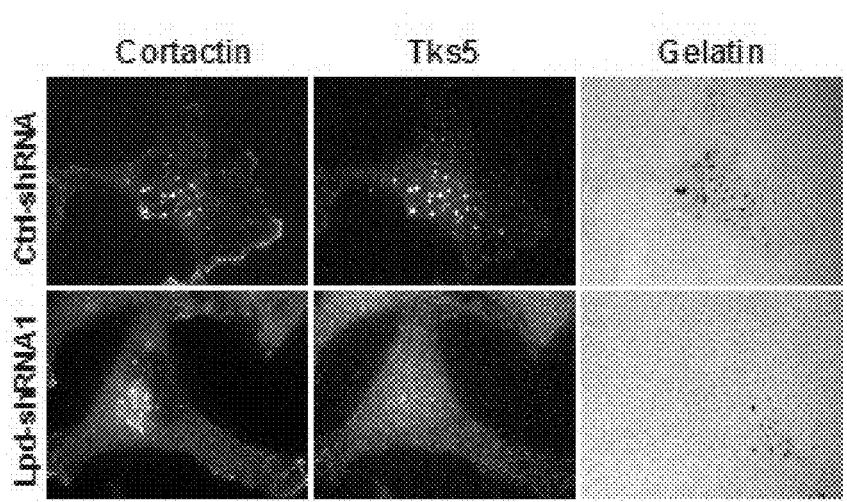
Figure 5J:
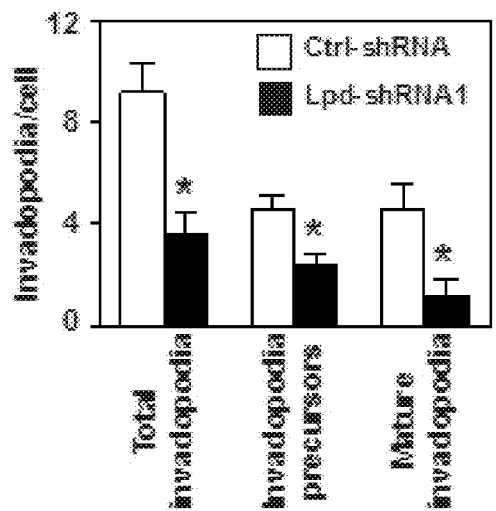
Figure 6A:
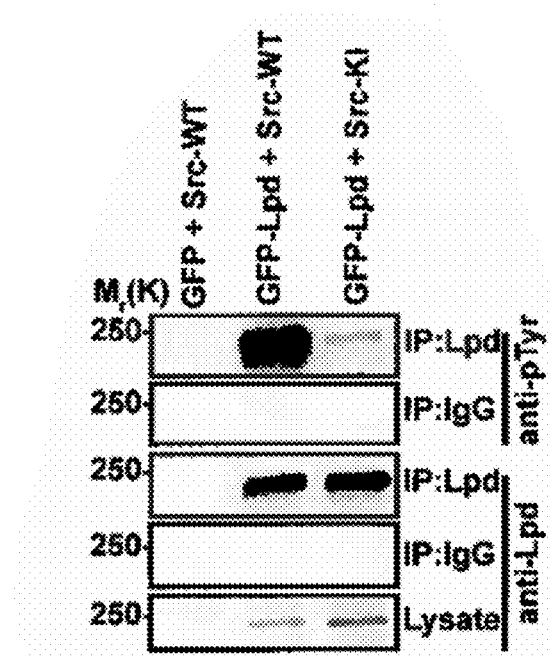
FIG. 6A-6O: c-Src phosphorylates Lpd and the Lpd-Scar/WAVE interaction is positively regulated by c-Abl and c-Src.
Figure 6B:
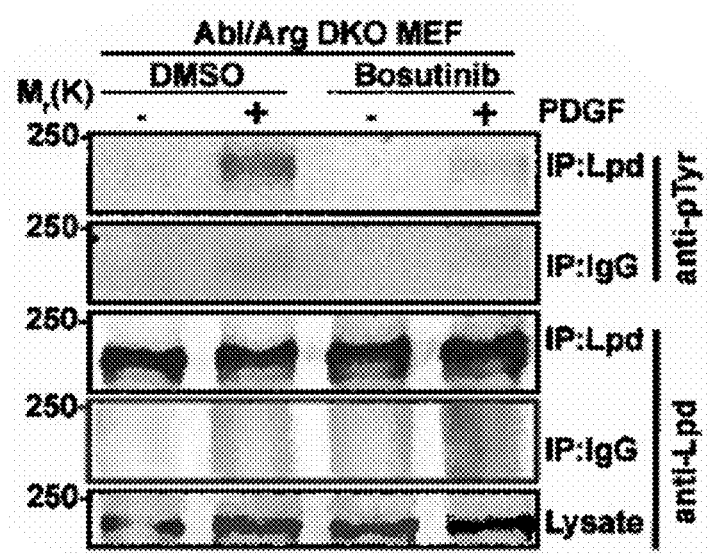
FIG. 6B: Abl and Arg double knockout MEFs (Abl/Arg DKO) were serum starved overnight and treated with 10i.tM Bosutinib (c-Src kinase inhibitor) for 2 hours before stimulating with 2Ong/ml PDGF-BB for 2 minutes. Immunoprecipitation was performed from cell lysates using Lpd-specific antibodies or rabbit IgG as control followed by Western blotting with anti-Lpd and anti-phosphotyrosine (pTyr) antibodies.
Figure 6C:
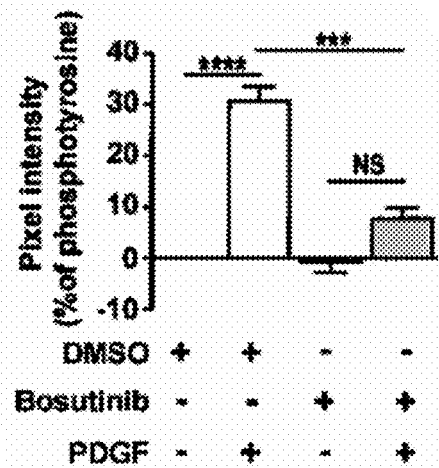
FIG. 6C: Quantified band intensities of chemiluminescence blots from 6B of Lpd and pTyr imaged with a CCD camera. pTyr was normalized against the immunoprecipitated Lpd. The pTyr signal from Rabbit IgG control lanes was subtracted from the pTyr signal from the immunoprecipitated Lpd lanes. n=3, data are represented as mean±s.e.m. One-way ANOVA; Dunnett's; *P≤0.001, ** P≤0.0001, NS—not significant.
Figure 6D:
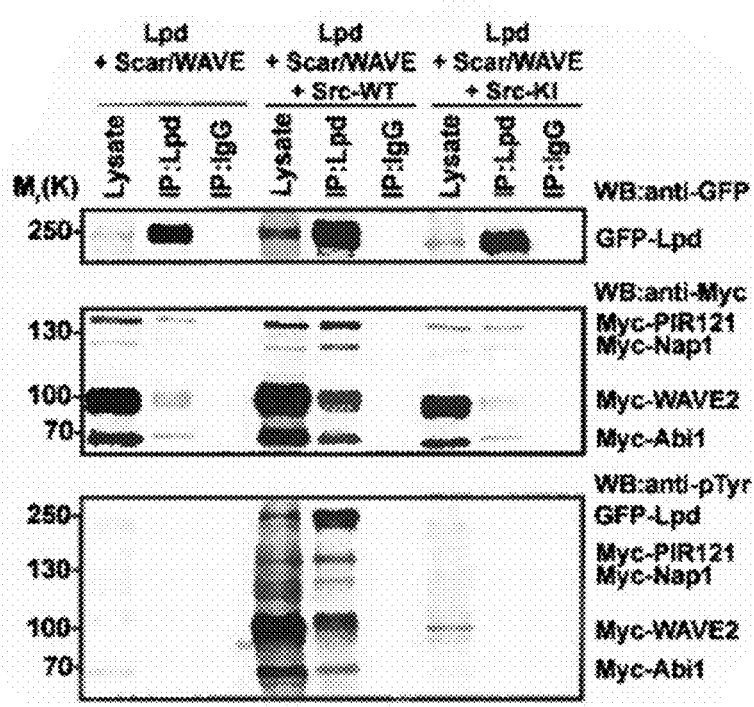
FIG. 6D: HEK293FT cells were transfected with GFP-Lpd, Myc tagged components of the Scar/WAVE complex and either Src-WT (wild type) or Src-K1 (kinase inactive). Immunoprecipitation was performed from cell lysates using Lpd-specific antibody or rabbit IgG as control followed by Western blotting with anti-GFP, anti-Myc and anti-phosphotyrosine (pTyr) antibodies.
Figure 6E:
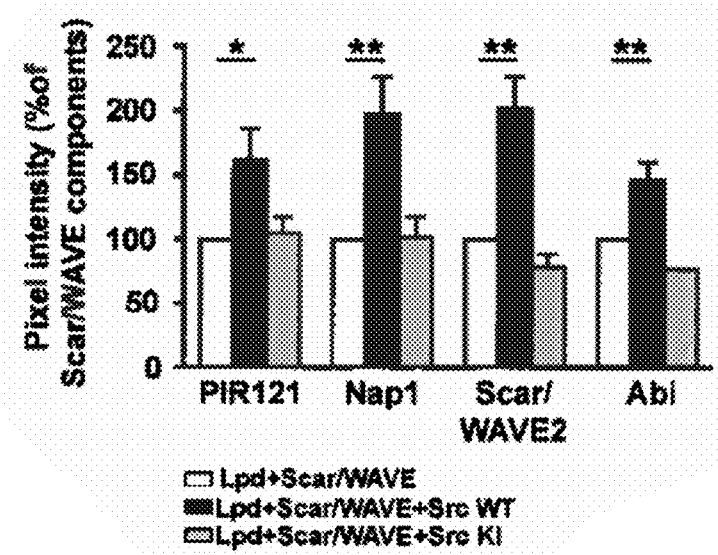
FIG. 6E: Quantified band intensities of chemiluminescence blots 6D of GFP Lpd and Myc tagged components of the Scar/WAVE complex imaged with a CCD camera. Individual Scar/WAVE components were normalized against the immunoprecipitated Lpd. n=4, data are represented as mean±s.e.m. One-way ANOVA; Dunnett's; * P≤0.05, P≤0.01.
Figure 6F:
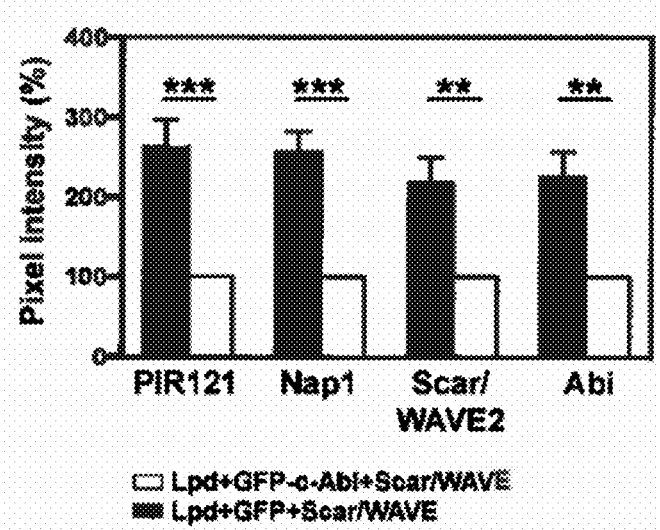
FIG. 6F: HEK293FT cells were transfected with GFP-Lpd, Myc tagged components of the Scar/WAVE complex and either GFP-c-Abl or GFP. Immunoprecipitation was performed from cell lysates using Lpd-specific antibody or rabbit IgG as control followed by Western blotting with anti-GFP, anti-Myc and anti-phosphotyrosine (pTyr) antibodies.
Figure 6G:
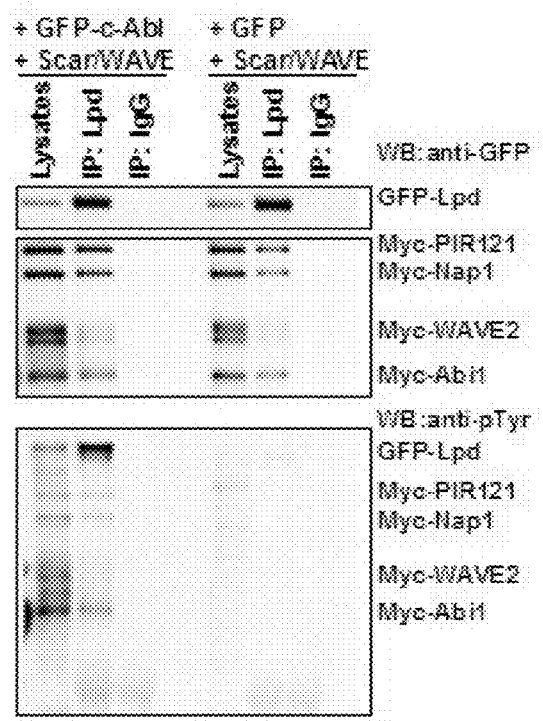
FIG. 6G: Quantified band intensities of chemiluminescence blots 6F of GFP-Lpd and Myc tagged components of the Scar/WAVE complex imaged with a COD camera. Individual Scar/WAVE components were normalized against the immunoprecipitated Lpd. n=4, data are represented as mean±s.e.m. One-way ANOVA; Dunnett's;  P≤0.01, P≤0.001. (H-O): Lpd is required for invasion of breast cancer cells.
Figure 6H:
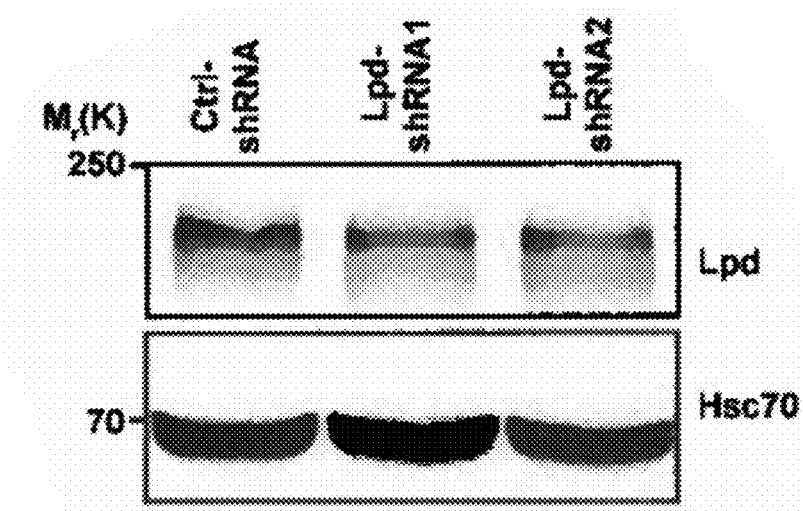
FIG. 6H: Western blot analysis of Lpd expression in MDA-MB-231 cells expressing Ctrl-shRNA, Lpd-shRNA1 or Lpd-shRNA2 used in FIG. 5a. Hsc70, loading control.
Figure 6I:
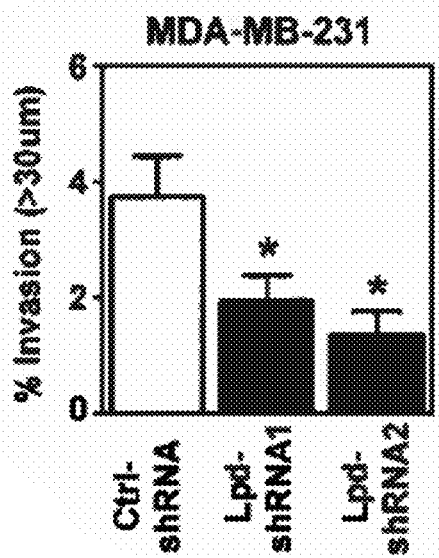
FIG. 6I: Quantification of 3D-inverted invasion assays using MDA-MB-231 cells expressing Ctrl-shRNA, Lpd-shRNA1 or Lpd-shRNA2 into plugs of collagen I (supplemented with 25 μg/ml fibronectin). Invasion is expressed as the proportion of cells that migrate further than 30 µm. Data are represented as mean±s.e.m; three independent experiments, each performed in duplicate. One-way ANOVA; Dunnett's; * P≤0.05.
Figure 6J:
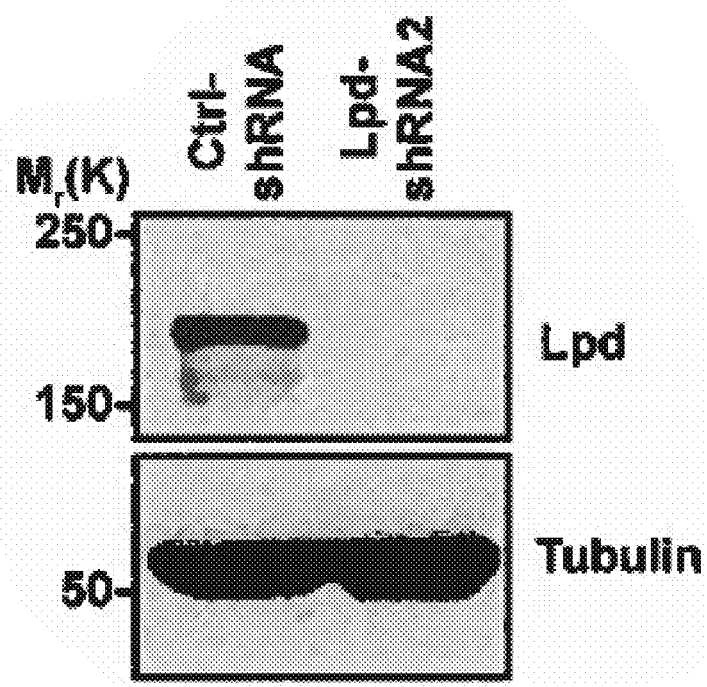
FIG. 6J: Western blot analysis of Lpd expression in Sum-159 cells stably expressing Ctrl-shRNA or Lpd-shRNA2. Tubulin, loading control.
Figure 6K:
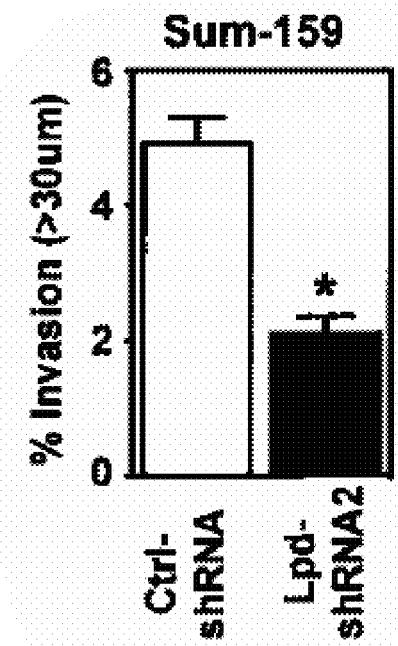
FIG. 6K: 3D inverted invasion assay with Sum-159 cells stably expressing Ctrl-shRNA or Lpd-shRNA2 into plugs of collagen I supplemented with 25 µg/ml fibronectin. Data are represented as mean±s.e.m; three independent experiments, each performed in duplicate. Unpaired t-test; * P≤0.05.
Figure 6L:
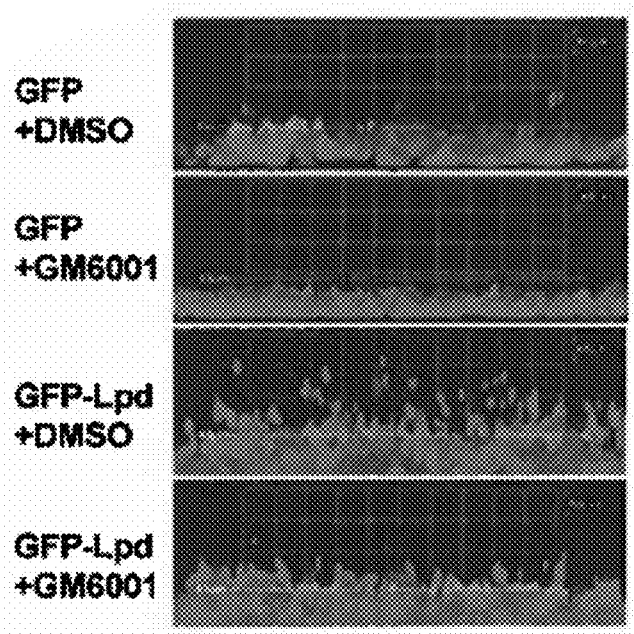
FIG. 6L: Inverted invasion assays were performed using MDA-MB-231 breast cancer cells stably expressing mCherry-1-126 (labeling the nucleus) transfected with GFP-Lpd or OFF' empty vector as control and incubated with 10 µM MMP inhibitor GM6001 or DMSO. The nuclei of the cells were visualized using confocal microscopy.
Figure 6M:
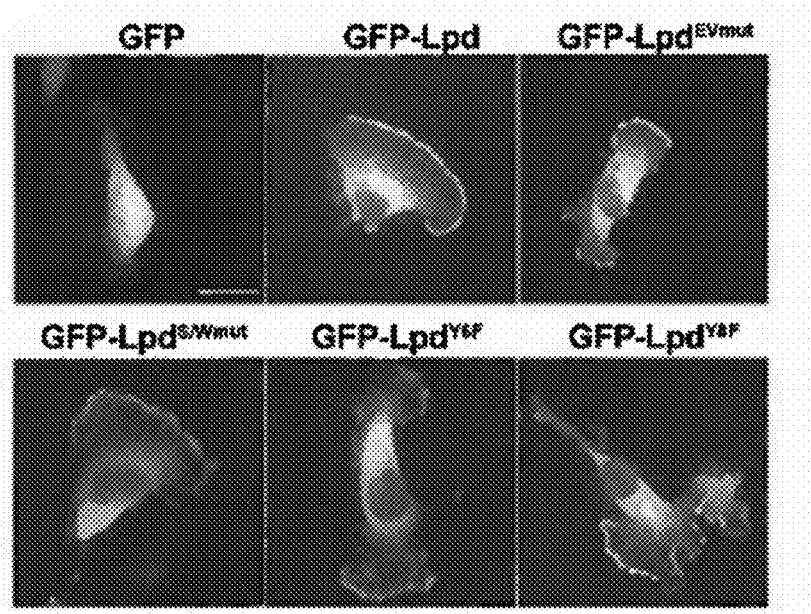
FIG. 6M: Representative images of MDA-MB-231 transfected with GFP-Lpd, GFP-LpdEVmut, GFP-LpdS/Wmut, GFP-LpdY6F, GFP-LpdY8F or GFP empty vector as control. Scale bar, 20 µm.
Figure 6N:
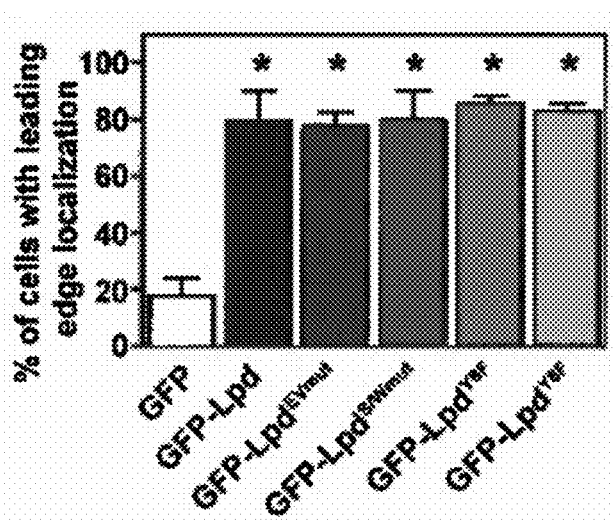
FIG. 6N: Quantification of percentage of cell displaying Lpd localization to the leading edge. Data are represented as mean±s.e.m. One-way ANOVA; Dunnett's; * P≤0.05.
Figure 6O:
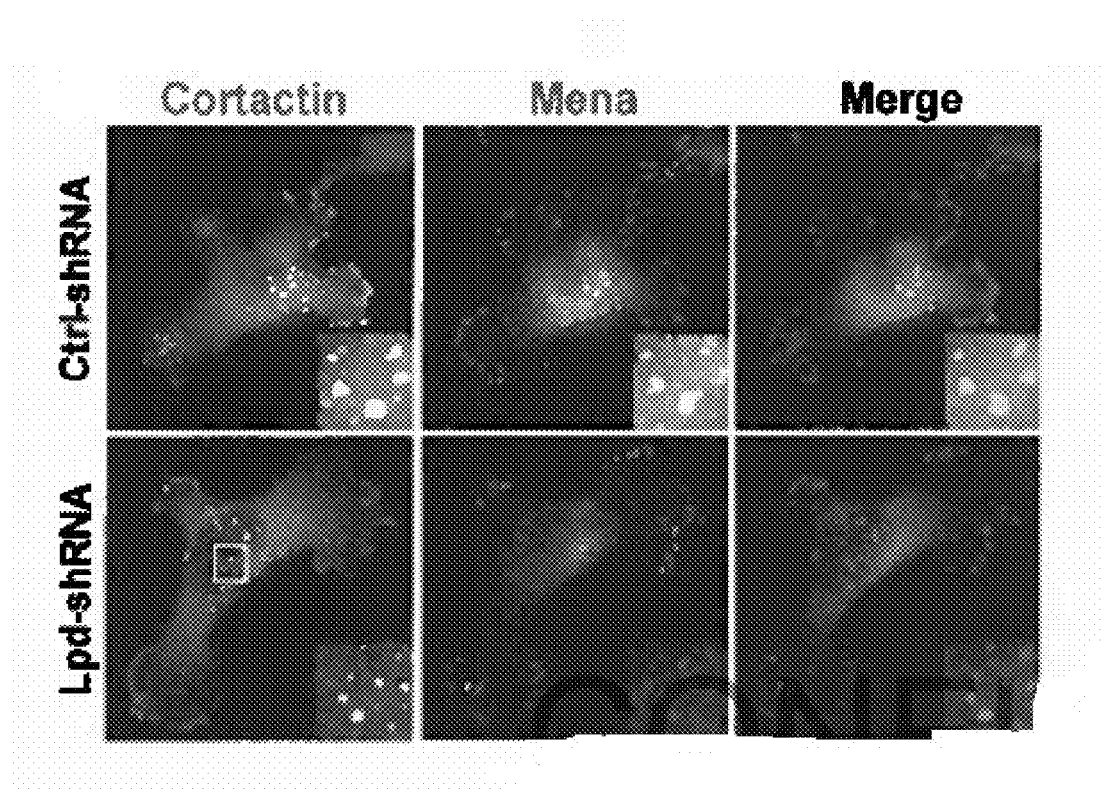

It has been reported in the literature that Mena promotes invadopodium stabilization and matrix degradation, and here it was observed that Lpd depletion appeared to reduce the amount of Mena within invadopodia considerably, potentially reflecting a role for Lpd in Mena recruitment to invadopodia (FIG. 6O). Silencing of Lpd in MDA-MB-231 cells decreased the number of precursors, mature invadopodia, and the total number of invadopodia in comparison to control cells (FIG. 5I, 5J).

Figure 5G:
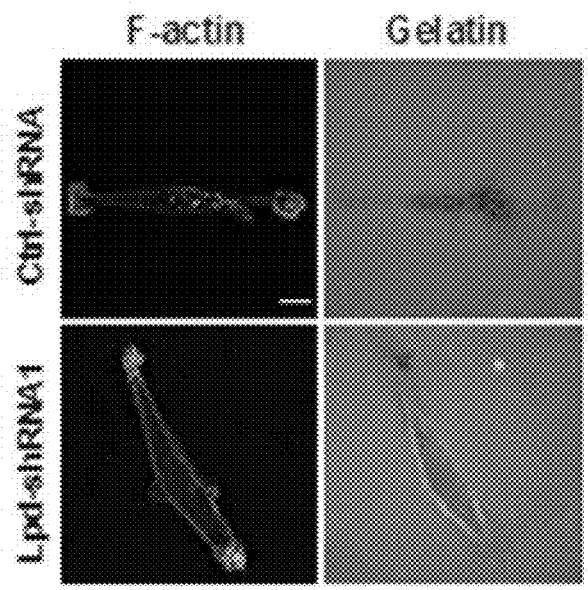
Figure 5H:
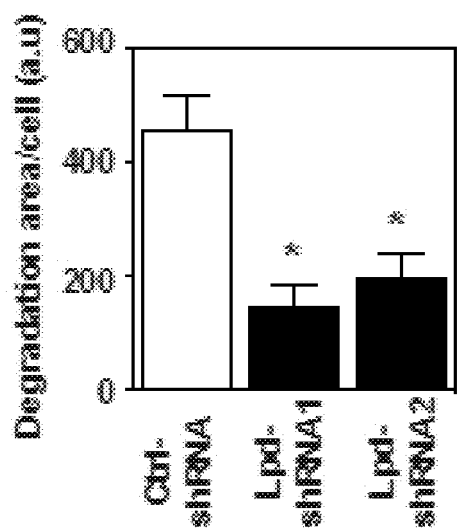
Figure 5K:
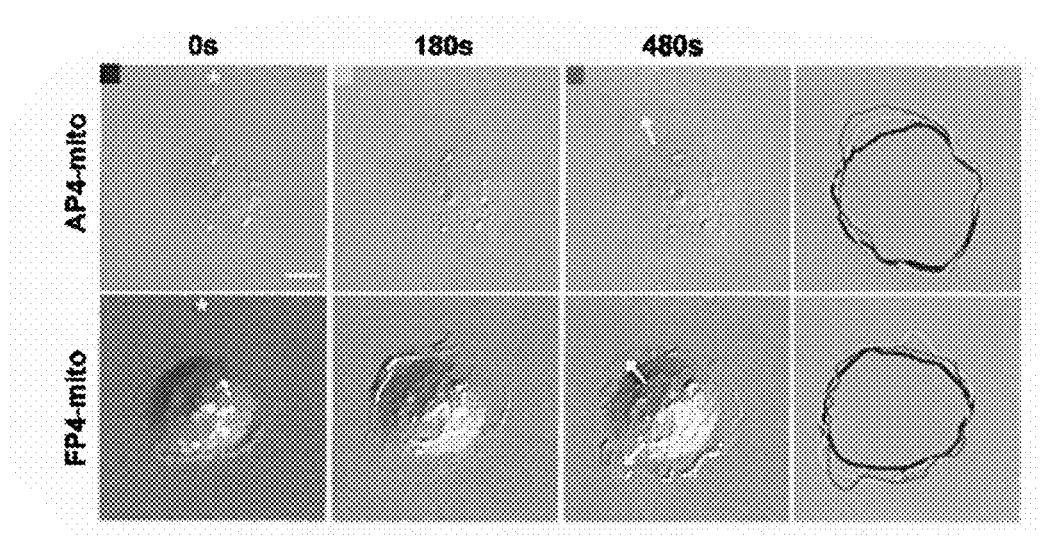
Figure 5L:
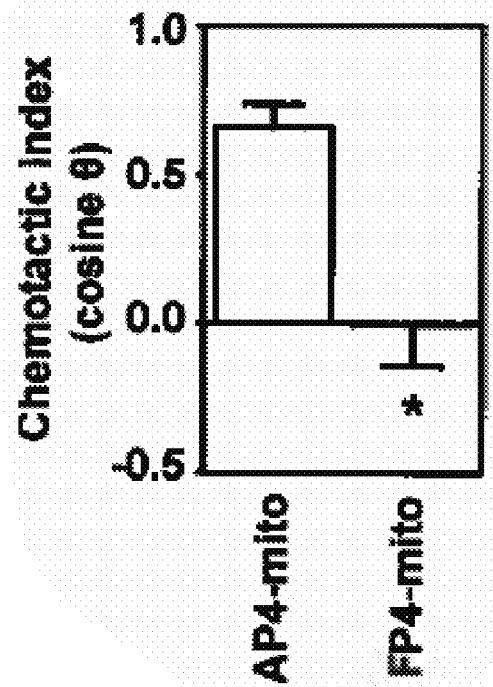
Figure 5M:
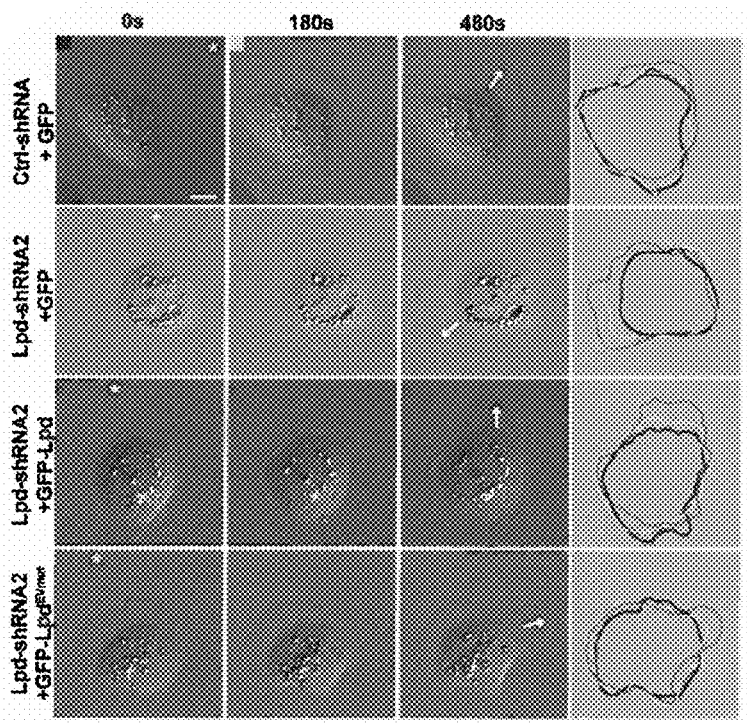

Furthermore, Lpd-depleted MDA-MB-231 cells exhibited a significant decrease in their ability to degrade matrix relative to control cells (FIG. 5G, 5H). Taken together, these results suggest that Lpd is required for invadopodial precursor formation or for both precursor formation and subsequent stabilization/maturation, and for invadopodia-mediated matrix degradation.

To test the relative contribution of Lpd interactions with Ena/VASP proteins or with the Scar/WAVE-complex during MDA-MB-231 3D invasion, a panel of Lpd mutants were overexpressed in which all Ena/VASP (GFP-Lpd$^{EVmut}$), all Scar/WAVE-binding sites (GFP-Lpds$^{S/Wmut}$), or all Ena/VASP and all Scar/WAVE-binding sites (GFP-Lpd$^{EV+S/Wmut}$) had been mutated. All of these mutants localized to the leading edge of MDA-MB-231 cells (FIG. 6M, 6N). At steady state when embedded in 3D matrigel, MDA-MB-231 cells overexpressing GFP-Lpd displayed significantly more protrusions, which protruded faster compared to GFP control cells. However, expression of Lpd-Ena/VASP-, Lpd-Scar/WAVE- and double-binding mutants all failed to increase protrusion numbers and speed (FIG. 7H) Similarly, these mutants did not support invasion through matrigel towards EGF, suggesting that Lpd promotes 3D chemotactic invasion via both Ena/VASP and Scar/WAVE (FIG. 5D, 5E). These findings, combined with previous observation that Lpd interaction with ScadWAVE but not Ena/VASP is required for random 2D migration, prompted to think further that interactions between Lpd and these actin regulators may be differentially regulated.

Previously it was found that Lpd is phosphorylated by Abl kinases upon growth factor stimulation, and this positively regulates its interaction with Ena/VASP proteins and their recruitment to the leading edge of cells. Since Src kinases are also activated upon growth factor stimulation and increased Src activity promotes cancer cell invasion, it was further explored whether Lpd interactions with downstream partners are regulated by Src phosphorylation.

GFP-Lpd was expressed with wild-type c-Src or a kinase-inactive mutant of c-Src and, after immunoprecipitation of Lpd, it was observed that it was tyrosine phosphorylated in cells expressing wild-type but not kinase-inactive c-Src (FIG. 6A). Both Src and Abl kinases are activated downstream of growth factor receptors, and Src phosphorylation of Abl kinases contributes to their activation. To distinguish between Src and Abl phosphorylation of Lpd and to investigate whether endogenous Lpd is phosphorylated by Src tyrosine kinases, Abl/Arg double knockout mouse embryonic fibroblasts were used. After PDGF-BB stimulation, Lpd was robustly tyrosine phosphorylated in the absence of both Abl kinases, Abl and Arg. This was blocked by the Src inhibitor Bosutinib (FIG. 6B, 6C), indicating Src kinase activity leads to Lpd phosphorylation upon growth factor receptor activation.

Figure 7B:
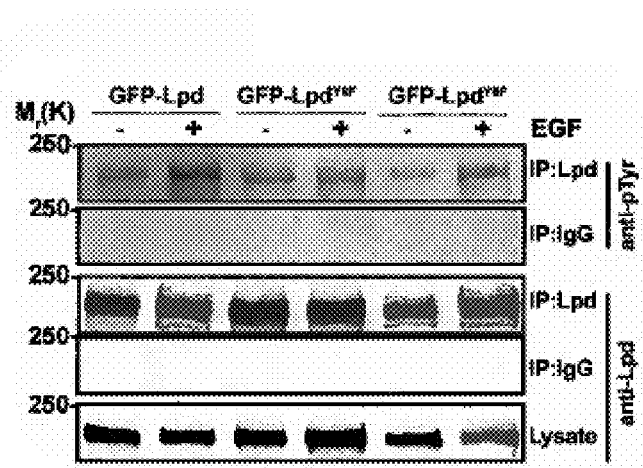
FIG. 7B: HeLa cells were transfected with GFP-Lpd$^{Y6F}$, GFP-Lpd$^{Y8F}$, or GFP-Lpd as control. HeLa cells were serum starved overnight and stimulated with bOng/ml EGE for 5 minutes. Immunoprecipitation was performed from cell lysates using Lpd-specific antibodies or rabbit IgG as control followed by Western blotting with anti-Lpd and anti-phosphotyrosine (pTyr) antibodies.
Figure 7C:
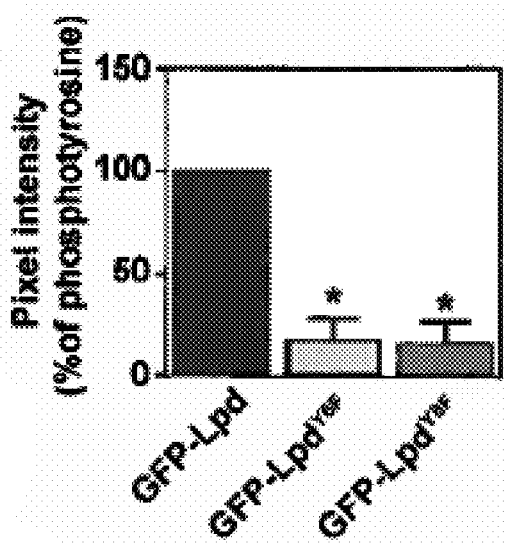
FIG. 7C: Quantified band intensities of chemiluminescence blots 7B of GFP Lpd, GFP-Lpd phospho-mutants, and pTyr imaged with a CCD camera. pTyr normalised against the immunoprecipitated Lpd. Baseline phosphorylation in the absence of EGF was subtracted from the corresponding EGF+ samples. n=6. Data are represented as mean±s.e.m. One-way ANOVA; Dunnett's; * p≤0.0001.
Figure 7D:
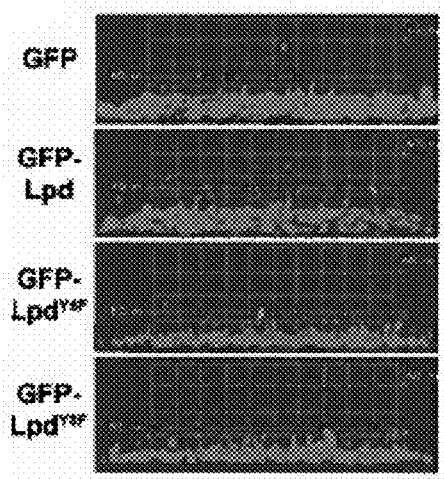
FIG. 7D-7E: Inverted invasion assays were performed using MDA-MB-231 breast cancer cells stably expressing mCherry-H2B (labeling the nucleus) transfected with GFP-Lpd, GFP-Lpd$^{Y6F}$, GFP-Lpd$^{Y8F}$ or GFP empty vector as control. The nuclei of the cells were visualized using confocal microscopy.
Figure 7E:
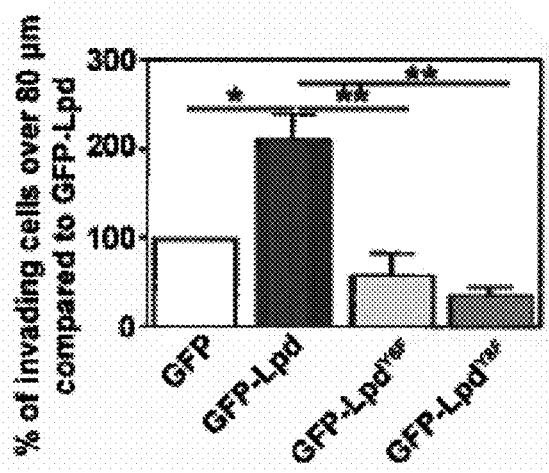
Figure 7F:
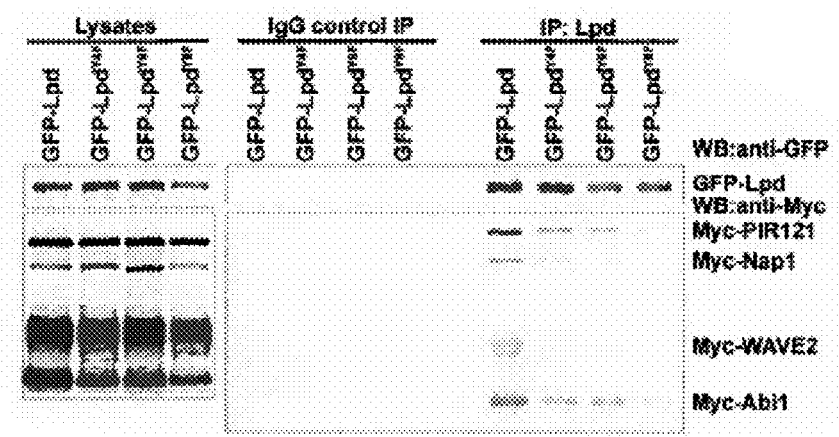
(FIG. 7F) HEK293FT cells were transfected with GFP-Lpd, GFP-Lpd$^{Y4F}$, GFP-Lpd$^{Y6F}$, GFP-Lpd$^{Y8F}$ and Myc tagged components of the Scar/WAVE complex. Immunoprecipitation was performed from cell lysates using GFP-specific antibody or rabbit gO as control followed by Western blotting with anti-GFP, anti-Myc and anti-phosphotyrosine (pTyr) antibodies.
Figure 7G:
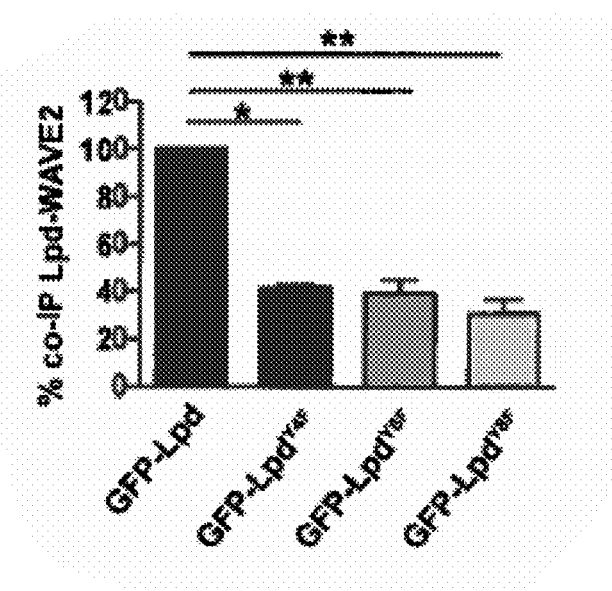
(FIG. 7G) Quantified band intensities of chemiluminescence blots 7F of GFP-Lpd and Myc tagged components of the Scar/WAVE complex imaged with a COD camera. Scar/WAVE2 was normalized against the immunoprecipitated Lpd. n=4, data are represented as mean±s.e.m. One-way ANOVA; Dunnett's; P≤0.01, ***P≤0.001.
Figure 7H:
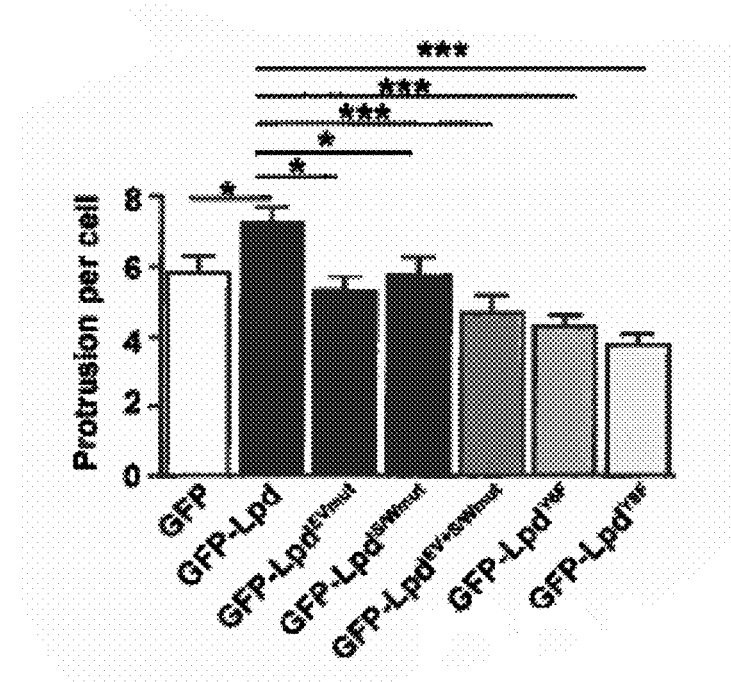
(FIG. 7H) Quantification of the number of protrusion of MDA-MB-231 transfected with GFP-Lpd, GFP-Lpd$^{EVmut}$, GFP-Lpd$^{S/Wmut}$, GFP-Lpd$^{EVmut+S/Wmut}$, GFP-Lpd$^{Y6F}$, GFP-Lpd$^{Y8F}$ or GFP empty vector as control plated in 3D matrigel n=35-46 cells for each mutant; from 5 experiments. Data are represented as mean±s.e.m. One-way ANOVA; Dunnett's; * p≤0.05, P≤0.001).
Figure 7I:
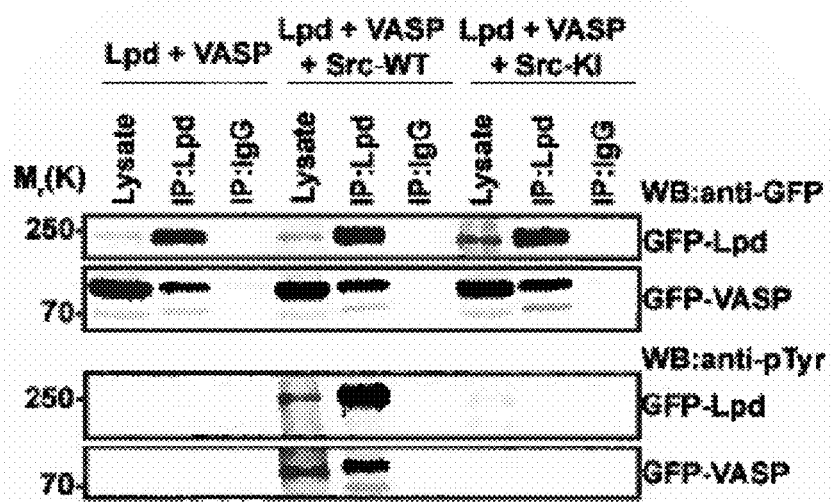
Figure 7J:
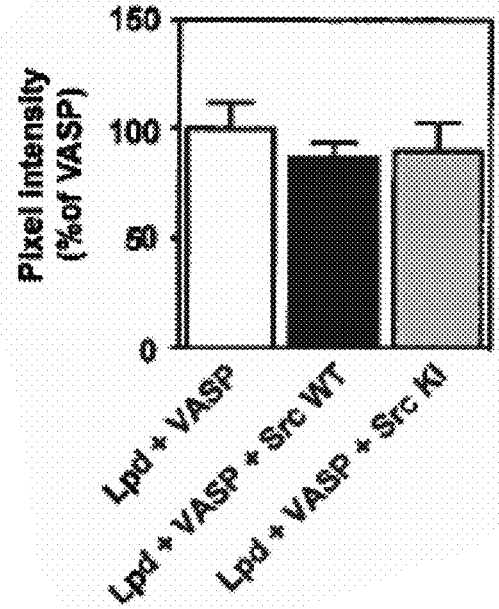
Figure 7K:
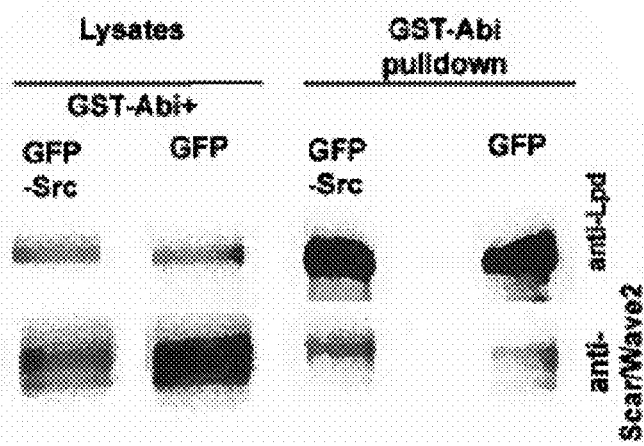
Figure 7L:
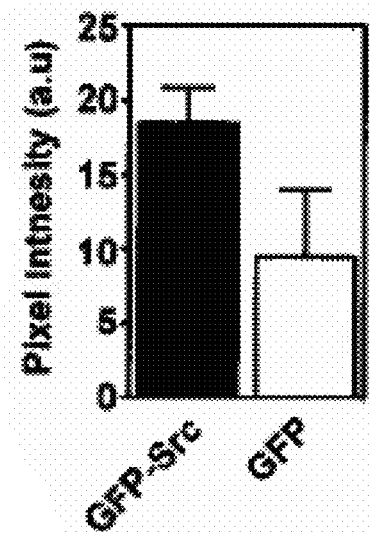

It was first investigated whether Src phosphorylation controls Lpd-Ena/VASP interaction, since this is positively regulated by Abl phosphorylation. Surprisingly, c-Src-induced Lpd phosphorylation did not affect Lpd-Ena/VASP binding (FIG. 7I, 7J). In contrast, co-immunoprecipitation between GFP-Lpd and Myc-tagged Scar/WAVE-complex revealed that significantly more Scar/WAVE-complex co-precipitated with Lpd when either c-Src or c-Abl was co-expressed (FIG. 6D-6G). It was also tested whether the interaction between endogenous Lpd and Scar/WAVE is positively regulated by c-Src by using ectopically expressed GST tagged Abl (which reduces endogenous Abl and thereby replaces it) to efficiently pull down the Scar/WAVE complex and associated proteins. GST-Abl pulldowns from cells co-expressing GFP-Src contained higher levels of endogenous Scar/WAVE2 co-precipitating with endogenous Lpd compared to GFP controls (FIG. 7K, 7L). Together, these findings indicate that the Lpd Ena/VASP interaction is regulated by c-Abl phosphorylation, whereas the Lpd Scar/WAVE interaction is positively regulated by both c-Abl and c-Src-dependent phosphorylation.

Figure 8:
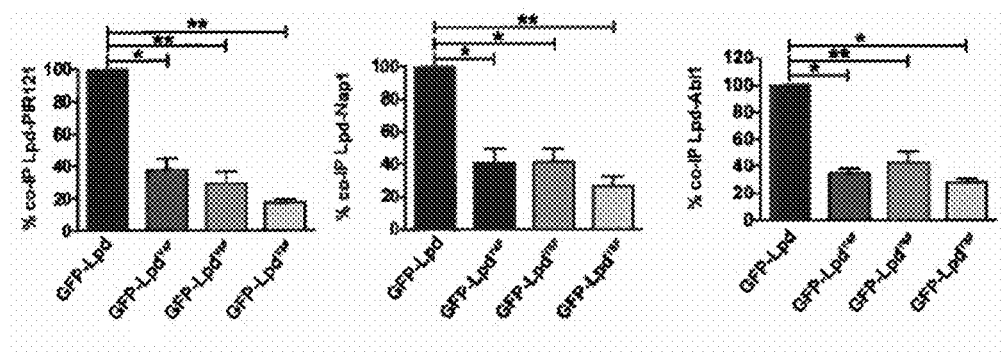
FIG. 8: Lpd phosphorylation by c-Src is required for its interaction with Scar/WAVE. (A) HEK293FT cells were transfected with GFP-Lpd, GFP-Lpd$^{Y4F}$, GFP-Lpd$^{Y6F}$, GFP-Lpd$^{Y8F}$ or GFP empty vector as control. Immunoprecipitation was performed from cell lysates using GFP-specific antibody or rabbit IgG as control followed by Western blotting with anti-GFP, anti-Myc. Quantified band intensities of chemiluminescence blots of GFP-Lpd and Myc tagged components of the Scar/WAVE complex imaged with a CCD camera. Individual Scar/WAVE components were normalized against the immunoprecipitated Lpd. n=4, data are represented as mean±s.e.m. One-way ANOVA; Dunnett's; * P≤0.05, ** P≤0.01. Data are represented as mean±s.e.m. One-way ANOVA; Dunnett's; * P≤0.05, **P≤0.01).

To better understand this differential regulation, potential direct c-Src phosphorylation sites in Lpd were identified, using purified c-Src kinase to phosphorylate an immobilized peptide array covering all putative tyrosine phosphorylation sites in Lpd. This analysis revealed that Lpd harbors two robustly and four weakly phosphorylated c-Src tyrosine phosphorylation sites (FIG. 7A). Previously eight c-Abl tyrosine phosphorylation sites were mapped in Lpd, which partly overlap with these newly identified c-Src sites (FIG. 7A). To verify that the Lpd phosphorylation sites identified in vitro were phosphorylated in cells, the tyrosines in the six c-Src (GFP-Lpd$^{Y6F}$) and the eight c-Abl (GFP-Lpd$^{Y8F}$) phosphorylation sites were mutated to phenylalanine, rendering them non-phosphorylatable. Overexpression of GFP-Lpd induced low levels of Lpd tyrosine phosphorylation, which was markedly enhanced by stimulation with 100 ng/ml EGF for 5 minutes. In contrast, neither GFP-Lpd$^{Y6F}$ nor GFP-Lpd$^{Y8F}$ tyrosine phosphorylation was enhanced when cells expressing these constructs were stimulated with EGF (FIG. 7B, 7C). It was observed that the GFP-Lpd$^{Y6F}$ and GFP-Lpd$^{Y8F}$ mutants interacted significantly less with the Scar/WAVE complex (FIG. 7F, 7G; FIG. 8). Nevertheless, GFP-Lpd$^{Y6F}$ and GFP-Lpd$^{Y8F}$ mutants localized to the leading edge of MDA-MB-231 cells similar to wild-type Lpd (FIG. 6 M, 6N). Taken together, the data indicates that full-length Lpd can be phosphorylated at these sites in cells upon EGFR activation likely as a consequence of activated Abl- and Src-kinases.

Figure 7M:
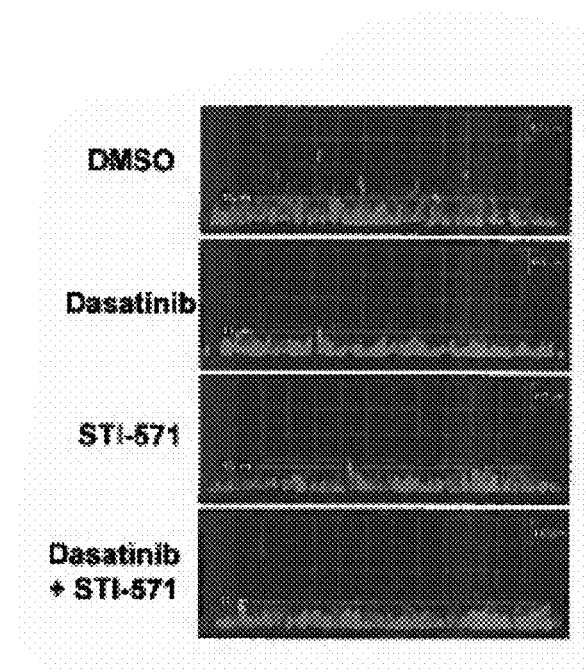
Figure 7N:
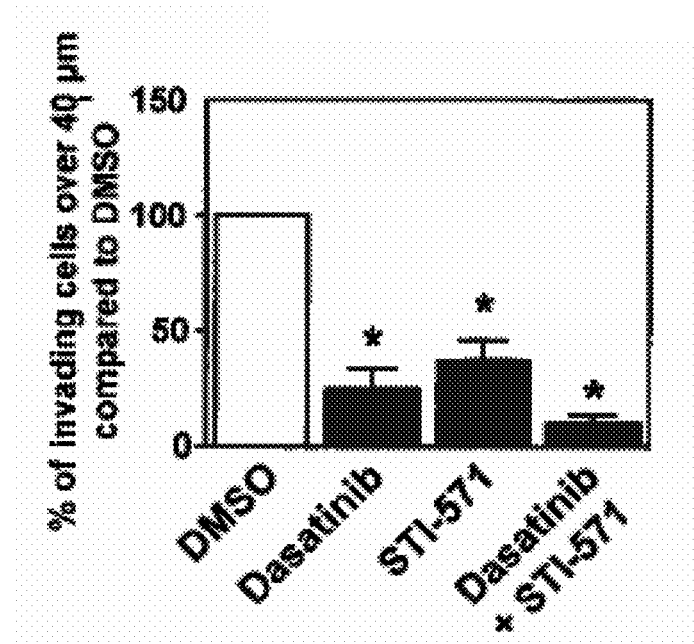
Figure 7O:
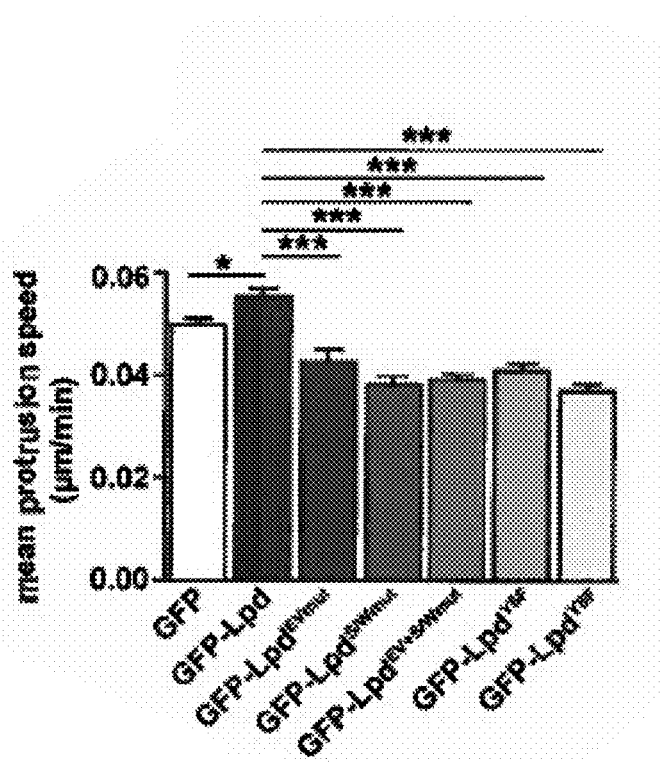

To verify that both Src and Abl kinases are required for breast cancer invasion towards EGF, the invasiveness of MDA-MB-231 cells with and without incubation with the Src and Abl inhibitors Dasatinib or ST1571 was further tested. As expected, it was found that breast cancer cell invasiveness is impaired when Src or Abl kinases were inhibited (FIG. 7M, 7N).

To investigate the functional significance of Lpd tyrosine phosphorylation for breast cancer invasion, the effects of overexpressing non phosphorylatable mutants, GFP-Lpd$^{Y6F}$ and GFP-Lpd$^{Y8F}$, were compared with control GFP-Lpd. It was observed that, in contrast to GFP-Lpd, neither of the mutants increased protrusion numbers or speed in cells embedded in matrigel at steady state, or the invasiveness of breast cancer cells through matrigel towards EGF (FIGS. 7D, 7E, 7H and 7O) suggesting that phosphorylation by both Abl and Src kinases is required for Lpd-mediated breast cancer invasion.

Figure 9A:
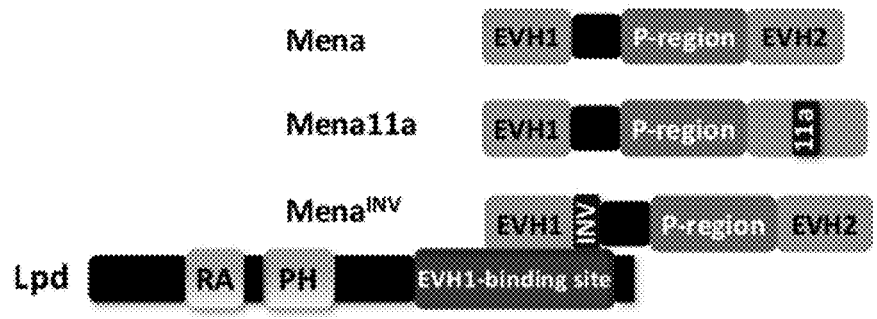
FIG. 9A-9C: Association of Lpd with Mena isoforms.
Figure 9B:
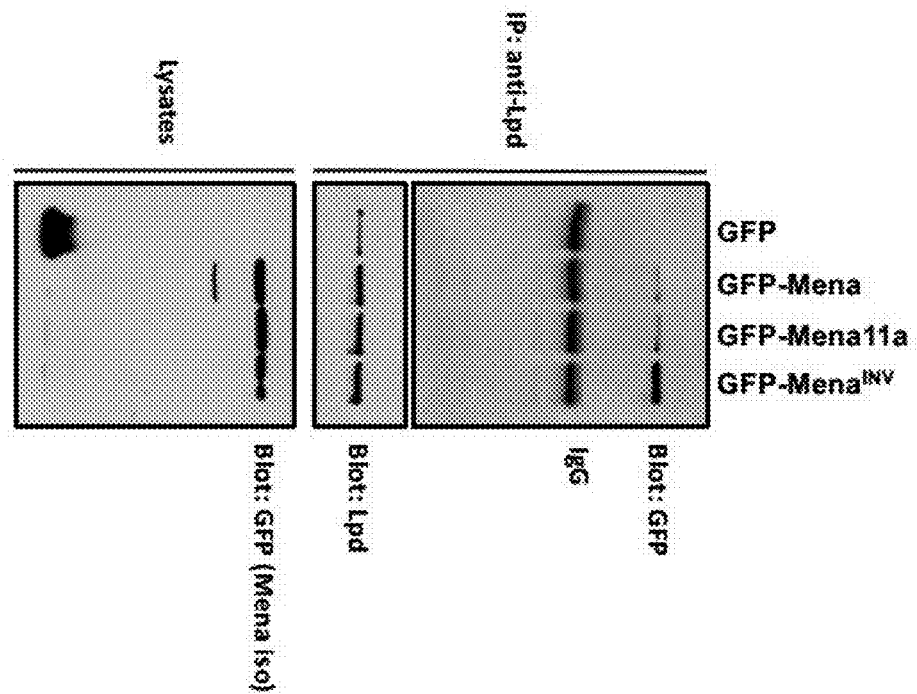
Figure 9C:
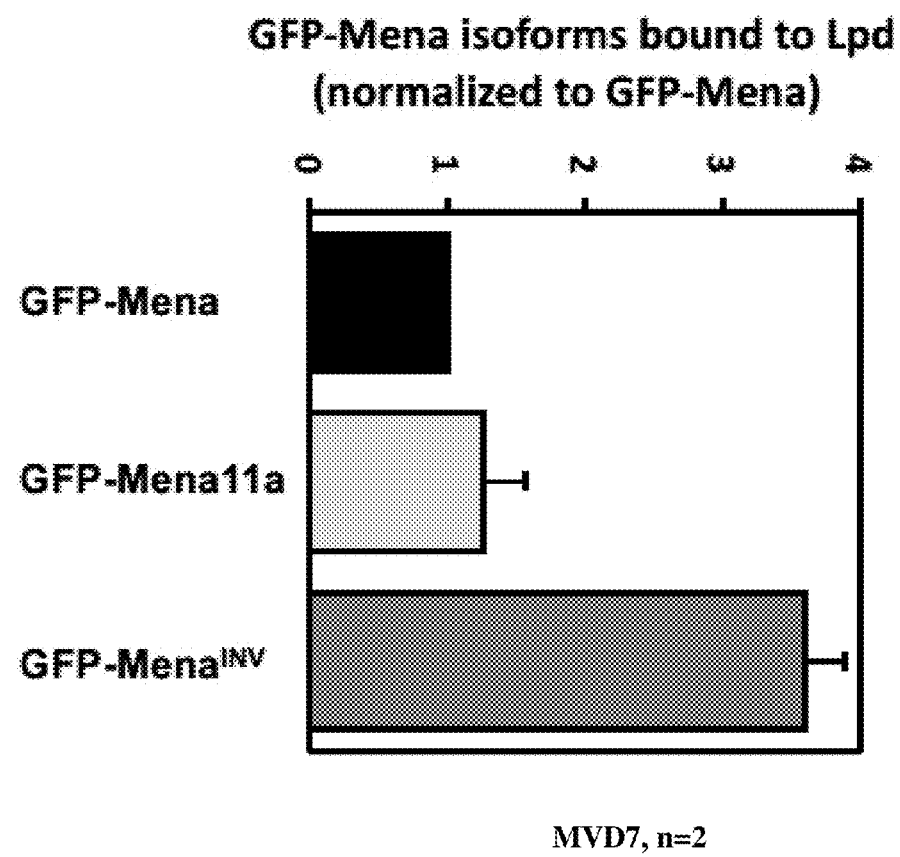

To understand the role of MenaINV, interaction of Mena-INV with Lpd was studied (FIG. 9A-9C). Lpd associates more robustly with MenaINV compared to other Mena isoforms. More MenaINV than Mena or Mena11a was co-immunoprecipitated with Lpd.

Disrupting the Lpd:MenaINV interaction with competing peptides might be useful in blocking tumor progression.

Materials and Methods

Plasmids and shRNAs

GFP-VASP, μmSCV-mRFP1-FP4/AP4-mito, Myc-Pir121, -Nap1, -Abi1d, -WAVE2 in pRK5-Myc-DEST. Lpd in pENTR (Invitrogen), mutated using Quikchange® (Agilent), transferred into pCAG-DEST-EGFP (Gateway®) (pCAG-EGFP; C.Cepko, Addgene,11150). pCB6-Src-WT-EGFP, pCB6-Src-KI(kinase-inactive)-EGFP, (M.Way).

GFP-Lpd$^{S/Wmut}$:AAS82582.1) Site 1:(aa968-978)GKKP (P>A) (P>A) T(P>A)Q(R>A)N; Site2:(aa1119-1129) APP (P>A)TR(P>A)K(R>A)ND; SITE3:(aa1230-1244) RRGP (P>A)A(P>A)(P>A)(K>A)(R>A)DQNT.

GFP-Lpd$^{EVmut}$:(AAS82582.1) FP4-1:aa869 F>A; FP4-2: aa916 F>A; FP4-3:aa927 F>A; FP4-4:aa1064 F>A; FP4-5: aa1073 F>A; FP4-6:aa1082 L>A; FP4-7:aa1202 L>A.

GFP-Lpd$^{Y4F}$: (AAS82582.1) Y>F:aa 426, 456, 513, 1226; GFP-Lpd$^{Y6F}$: (AAS82582.1) Y>F:aa366, 426, 456, 466, 481, 510; GFP-Lpd$^{Y8F}$: (AAS82582.1) Y>F:aa366, 426, 456, 466, 481, 510, 513, 1226;

pLJM1-H2BK-mCherry: histone H2BK amplified from A431 cell by RT-PCR cloned into pLJM1-mCherry (D. Sabatini; Addgene plasmid #19319).

shRNAs were cloned into pLL3.7-Puro, miR30-MLS EGFP/mCherry, or MSCV-ZsG-2A-Puro-miR30 retroviral vector. Cells were FACS sorted or puromycin (Invitrogen) selected and knockdown tested by Western blot. shRNA (5'-3') used:

FIG. 2-6;

```
humanLpd-shRNA1:
TTTCCCCAAAAGATAATTCTG humanLpd-shRNA2:
TTCCCATACTTTGCAATGCGG ratLpd-shRNA2:
TAGAGCTCACAGTACTTTGGG ratLpd-shRNA3:
AAGAGGTCCAATCATAAGCTG Control-shRNA (targeting luciferase):
TTAATTAAAGACTTCAAGCGG
```

FIG. 2, 5, 6

```
Human Lpd-shRNA-1:
GCGTCAAATCACAGAAACG

Human Lpd-shRNA-2:
GCTCTGAATCAGGGAGAGA

Control-shRNA (Lpd-scrambled):
GCCGATAACCGAGAATACC
```

Cell Culture and Transfection

HEK293, BT549, MCF7, T47D cells from ATCC and maintained according to ATCC's protocol. SUM-159 and MTLn3 cells cultured as described. HEK cells expressing GST-Abi2 and GFP-Src were treated for one hour with 100 μM KB SRC 4 (Tocris) before lysis. Abl1/Abl2 double knockout MEF's (gift of T. Koleske, Yale), MDA-MB-231 cells (gift of A. Ridley) and MDA-MB-231 LM2 cells (gift from J. Massague, MSKCC) were cultured in high-glucose DMEM, penicillin, streptomycin, 10% FBS. MTLn3 and MDA-MB-231 transfection: Lipofectamine2000 (Invitrogen). Abl1/2DKO MEFs were serum starved (18 h) and treated with 10 μM Bosutinib (Cambridge Biosciences) (2 hours) in DMSO or DMSO (control), then stimulated with 20 ng/ml PDGF-BB (2 minutes).

Antibodies

Lpd pab 3917, Mena mab A351F7D9, Wave2 (Cell Signaling Technology), p34Arc (Millipore, 07-227), Tubulin (DM1A), Hsc70 mab (Santa Cruz), GFP mab (Roche), Myc mab (Sigma, 9E10), pTyr mab (Millipore, 4G10), Vimentin (550513, Biosciences). Alexa-conjugated secondary antibodies, phalloidin (Invitrogen, Biotium) diluted 1:50-1000.

Immunoprecipitation, GST-Pulldowns and Western Blotting

Was performed as described[20].

Cells were harvested in lysis buffer (50 mM Tris HCL; 200 mM NaCl; 1% NP-40; 2 mM MgCl2; 10% Glycerol (pH 7.4); 1 mM Na3VO4; 10 mM NaF; protease inhibitors (complete mini without EDTA, Roche). Lysates were incubated on ice for 30 min, centrifuged at 17,000×g at 4° C. for 15 min and protein concentration determined (Pierce® BCA protein assay kit (Thermo Fisher). Lysates were precleared with protein A beads (Thermo Fisher), incubated with glutathione beads for GST pulldowns or with antibody or control IgG, followed by 1% BSA blocked protein A beads for IP. Beads were washed with lysis buffer, separated on SDS-PAGE gels, transferred onto Immobilon-P membranes (Millipore), blocked in 5% BSA and probed with the indicated antibodies, followed by HRP-secondary antibodies (DAKO). Blots were developed with the ECL kit (Pierce or GE Healthcare) and X-ray film or the Immun-Star WesternC™ ECL kit using the Biorad Imager and quantified using ImageLab and ImageJ software.

Peptide Array Assay

Was done using Src kinase (NEB) as described[19]. Custom-made immobilized peptide arrays (CR-UK) were incubated overnight at room temperature in kinase buffer (50 mM Tris-Hcl, 10 mM MgCl2, 1 mM EGTA, 2 mM DTT, 0.01% Brij 35) with 0.2 mg/ml bovine serum albumin (BSA) and 10 mM NaCl, were blocked for 45 min at 30° C. in kinase buffer with 1 mg/ml BSA and 100 mM NaCl, and were incubated with kinase buffer+0.2 mg/ml BSA+120 units Src (NEB)+24 μCi γ-32P-ATP for 2 hr at 30° C. Washed membranes (10×15 min 1 M NaCl, 3×5 min H2O, 3×5 min H3P04, 3×5 min H2O, 2×2 min ethanol) were dried and analyzed with a Phosphorimager Typhoon 9200 (Amersham).

Immunofluorescence Microscopy

Cells were fixed with 4% paraformaldehyde-PHEM medium for 15 minutes, rinsed in PBS, permeabilized in 0.2% Triton X-100-PBS, blocked with 10% BSA in PBS, and labeled with primary and secondary antibodies. Cells were imaged on a Deltavision microscope (Applied Precision, Olympus IX71, 60×/1.4NA Plan Apo objective) and processed using Softworx software (SGI, Mountain View, Calif.).

Imaged: Deltavision microscope (Applied Precision, Olympus IX71, 60×/1.4NA, Softworx software) (SGI, Mountain View, Calif.). Olympus IX-81 microscope (Metamorph, Photometrics Cascadell 512B camera, 40× UPlanFL, 60× PlanApoNA1.45, or 100× UPlanApoS NA1.4 objectives) was used. Leading edge localization (FIG. 6N) was quantified by two blinded observers from 3 independent datasets (n=32-38 cells for each mutant).

Inverted Invasion Assay

5×10$^5$ MDA-MB-231 cells stably expressing mCherry-H2B were seeded onto underside of 8 μm pore-size transwell inserts (Greiner Bio-One Ltd) containing matrigel ((BD Biosciences, UK) polymerised 30 min (37° C.)). Inserts were inverted after cells adhered (4 hours), placed in serum-free medium, and normal growth medium containing EGF (25 ng/ml) placed on top. Inhibitors used: 10 µM GM6001; STI571 10 µM; Dasatinib 10 nM. 72 hours later, cells that did not cross the transwell filter were removed, invading cells visualised by confocal microscopy; 2.5 µm sections. The number of nuclei of invading cells above 40 µm or 80 µm was automatically quantified using Volocity software.

Inverted Invasion Assay on Collagen

Cells were suspended in serum-free collagen 1 (2.3 mg/ml) supplemented with fibronectin (25 pg/ml) to a final concentration of 2×103 cells/100 µl. Aliquots (100 µl) were dispensed into 96-well Costar plates coated with 3% heat-inactivated bovine serum albumin. Plates were centrifuged at 300×g and incubated at 37° C./5% CO2 for 30 mm, and EGF was added; cells were fixed after 24 hours in 4% paraformaldehyde in PBS and stained with 5 µg/ml Hoechst 33258 (Molecular Probes-Invitrogen). Samples were run in duplicate, and analyzed on a confocal microscope by taking optical z sections every 5 pm, starting at the bottom of the well. Two random microscopic fields were counted for each replicate. Nuclear staining was analyzed with the Imaris Cell and Imaris MeasurementPro of Imaris 6 software (Bitplane Scientific Software), and 3D reconstructions of invaded cells were made using the Spot component of this module. The invasion index (number of cells >30 µm divided by the total number of cells) was calculated.

Extravasation Metastasis Assay

For the experimental lung metastasis assay, 5×104 cells in 100 µl of Hank's Balanced Salt Solution were injected into the lateral tail vein of 6- to 8-week-old female NOD/SCID/IL2RV-null mice. The mice were sacrificed 28 days post-injection and lungs were inflated with 3.8% formaldehyde imaged with a fluorescence microscope and subsequently fixed overnight with 3.8% formaldehyde. ZsGreen-positive foci were counted in the left pulmonary lobe using ImageJ and counts were manually curated as needed.

Membrane Protrusion Assays

Membrane protrusion assay for EGF treated cells was performed as described. Kymographic analysis was performed to analyze the protrusion parameters including: protrusion persistence, distance, velocity and protrusion initiation after EGF stimulation.

For membrane protrusion assay in 3D matrigel, MDA-MB-231 cells were stained with CellTracker Green dye (ThermoFisher, UK) embedded in matrigel (BD Biosciences, UK) in µ-slide chambers (81506 Ibidi, Germany). 4 hours after plating, 5 minute movies, one frame every 15 sec; 40×; Olympus IX-81 were generated and protrusive activity around the entire circumference between frames automatically quantified from thresholded movies using ImageJ plugin ADAPT.

Micropipette Assay

The micropipette assay was performed as described[53,56].

A Femtojet Micromanipulator 5171 (Eppendorf-Brinkman Instruments) and a pump (model Femtojet; Eppendorf) were used to control the position of the micropipette and the pressure required for the chemoattractant flow, as described (Mouneimne et al., 2006). To induce protrusions, a micropipette was filled with 25 nM EGF, was placed approximately 10 µm away from the edge of a quiescent cell, and was pressure-exerted to induce flow. Time-lapse series were recorded using a 20× objective, and analyzed as above. By defining the centroid, the cells were grouped into those with a front part or a back part: the front was designated the area of cell facing the micropipette, by drawing a line through the centroid and the tip of the micropipette, while the back of the cell referred to the other side of the cell. The chemotactic index, cosine θ, was also measured, with the angle θ defined as the angle made by the maximal protrusion (at the end of the movie—8 min) relative to the line connecting the cell centroid to the pipette tip. Front/back area protrusions and fold change were quantified by cell tracing and use of ImageJ. Front and back areas for each cell were standardized over the front and back areas, respectively, of the corresponding cell at time=0 (introduction of the pipette); these areas were averaged and plotted over time after EGF stimulation. Correlative microscopy was used to analyze leading edge staining in chemotactic cells. Briefly, MTLn3 cells were stimulated with an EGF micropipette for 1 min, fixed with 4% paraformaldehyde-PHEM medium, and immunostained as described in Immunofluorescence Microscopy section above. Cells stimulated (identified by fiduciary marks prior to fixation) with an EGF micropipette were imaged on a Deltavision microscope (Applied Precision, Olympus IX71, 60×/1.4NA Plan Apo objective) and processed with a Softworx software (SGI, Mountain View, Calif.).

Barbed-End Assay

G-actin was extracted from rabbit muscle acetone powder and standard techniques used to gel-filter over a Superdex-200 gel filtration column. The G-actin was polymerized to F-actin in F actin buffer (1 mM ATP, 5 mM $MgCl_2$, 50 mM KCl, 50 mM Tris/HCl, pH 8.0), labeled with Rhodamine-X succinimidyl ester (Invitrogen; following manufacturer's instructions), depolymerized in G-actin buffer (0.2 mM ATP, 0.5 mM DTT, 0.2 mM $CaCl_2$, 2 mM Tris/HCl, pH 8.0) to G-actin, and passed through PD-10 columns (GE Healthcare) to eliminate free rhodamine. The barbed-end assay in MTLn3 cells was performed as described[16]. Images taken with deconvolution microscope; the ratio of the barbed-end intensity to phalloidin intensity along the edge (the zone between 0 and 0.66 µm inside the cell) quantified as described above.

Invadopodium Degradation and Immunofluorescence.

MDA-MB-231 cells used in this study were cultured on FN/gelatin matrix (for 8 hours) or thin gelatin matrix (for 4 hours), and treated as described[57].

MDA-MB-231 cells used in this study were cultured on FN/gelatin matrix (for 8 hours) or thin gelatin matrix (for 4 hours), and treated as described (Sharma et al., 2013). Cells were plated on labeled gelatin matrix, fixed, stained with appropriate antibodies, and imaged on a Delta Vision epifluorescence microscope (Applied Precision Inc.). Invadopodium precursors were identified as cortactin and Tks5 positive puncta without the degradation hole. Mature invadopodia were identified as cortactin and Tks5 positive puncta colocalizing with degradation hole.

Zebrafish Tumor Cell Dissemination Assay.

The zebrafish tumor cell dissemination assay was done as described (Lee et al., 2009): Fertilized zebrafish (*Danio rerio*) eggs were collected and incubated at 28° C. under standard laboratory conditions. At 48 hours post fertilizations, zebrafish embryos were dechorionated with two sharp tip forceps and then anaesthetized in 0.04 mg/ml of tricaine (Sigma-Aldrich) solution.

Tumor cells were labeled with 2 µg/ml of 1,1-Dioctadecyl-3,3,3,3-tetramethylindocarbocyanine perchlorate (red fluorescent dye) prior to injection. Approximately 5 nl containing 100-500 MDA-MB-231 cells were injected into the perivitelline cavity of each embryo with non-filamentous borosilicate glass capillary needles (1.0 mm in diameter, World Precision Instruments, Inc. USA) connected to a micromanipulator (MN-151, Narishige, Japan) and an Eppendorf microinjector (FemtoJet 5247, Eppendorf, Germany). Cells were implanted into the perivitelline space of the embryo and subsequently kept under standard condition. Tumor cell dissemination to the trunk, 2 days post injection, was imaged using a fluorescent microscope (Nikon, Japan) and quantified using ImageJ.

Mouse Models

Tumor growth and spontaneous metastasis formation assayed by injecting tumor cells orthotopically into inguinal mammary fat pads (6-8 week-old female NOD/SCID/IL2Rγ-null mice) (Jackson Laboratory, Bar Harbor, Me.). Mice anesthetized with isoflurane, injected with $1.5 \times 10^5$ cells in Hank's Balanced Salt Solution (Gibco); sacrificed 6±0.5 weeks post-injection; tumors dissected, weighed, flash frozen, stored (−80° C.) or fixed: 3.8% formaldehyde, imaged with a fluorescence microscope, and embedded in paraffin and sectioned. Lungs were collected, fixed: 3.8% formaldehyde, embedded in paraffin, sectioned and stained with hematoxylin and eosin (H&E). ZsGreen-positive foci were counted in left pulmonary lobe using ImageJ.

Intravital Imaging

Female NOD/SCID/IL2Rγ-null mice (6-8 week-old) injected in the mammary fat pad with Ctrl-shRNA or Lpdh-sRNA2-expressing LM2 cells. Experiments were performed as described previously[58]. 5 mice per group. Collagen I fibers imaged by second harmonic generated polarized light. Cell motility observed by time-lapse imaging: 30 min in 2-min cycles. Three-dimensional time-lapse videos analysed: Image J. Tumour cell motility quantified manually. A cell was scored as motile if the translocation of the cell body was visible over the course of a 30 min video within a visual field that is defined in three dimensions as 50 μm by 512×512 pixels. Protrusion was defined as tumors cells showing a dynamic lamellipodia-like morphology. A protrusion was defined to be at least 5 μm long, but less than half the length of the cell. Directionality was calculated as described[58].

Statistics

Statistical analysis performed by ANOVA with appropriate posthoc tests (see FIGURE legends), or Student's t-test using Prism 5 (GraphPAD Software). P values <0.05 considered significant.

Clinical Data Sets Analysis

Oncomine for Lpd mRNA expression from microarray data. Statistical survival analysis (Kaplan-Meier plots): ROCK. Expression value of Lpd: upper quartile (25% against rest) for the NKI295 and Loi data sets, or upper tertile (33% against rest) for the Miller data set. The log rank p-value was used for statistical significance.

Tissue Microarrays

TMAs: 0.6 mm$^2$ cores of formalin-fixed, paraffin-embedded invasive breast tumor samples (312 consecutive patients) with clinicopathological data (King's Health Partners Cancer Biobank, London, UK). Automated immunohistochemistry (IHC) (VENTANA Discovery UTLRA) of 3 μm TMA sections, deparaffinized (EZ prep; Ventana Medical) (30 minutes, 72° C.), antigen retrieval: automated slide stainer (ULTRA CC2 solution, Ventana Medical) (68 minutes, 91° C.). Affinity purified polyclonal rabbit Lpd antibody in PBS (1:250) (32 minutes, room temperature). Slides counterstained with hematoxylin II and bluing reagent (Ventana Medical) (4 minutes each), dehydrated: 1×70% IMS, 1 minute, 2×100% IMS, 1.5 minutes, 3× xylene, 1 minute, mounted (Eukitt®) and imaged (Leica microscope, 40×).

Intensity of Lpd in cytoplasm and membrane assessed on TMAs using weighted histoscore (H-Score) method: Intensity in majority of cells assessed as negative and weak (1), or moderate and strong (2), then multiplied by the percentage of cells within this category. The weighted histoscore: 0-200; divided into thirtiles. Cytoplasma: histoscore 1 (0-88.75); histoscore 2 (88.75-170); histoscore 3 (170-200). Membrane: histoscore 1 (0-25); histoscore 2 (25-95); histoscore 3 (95-200). TMA's were assessed by two independent observers (U.P. and C.G.). Intensity scores that varied by more than a factor of one or a proportion by more than 20% were jointly reassessed and consensus reached. For all other cases, the mean score was used. Disease specific survival curves generated using Kaplan-Meier method. The log-rank test was used to compare statistically significant differences between subgroups. Univariate and multivariate analyses Cox proportional hazards regression models used to evaluate overall and breast cancer-specific death by histoscore of Lpd intensity in cytoplasm and at membrane. All analyses: Statistical Analysis Systems (SAS); 9.4 (SAS Institute, Cary, N.C.).

Lpd is required for metastasis in an orthotopic breast cancer mouse model, and that increased Lpd levels correlate with reduced metastasis free survival in breast cancer patients. Lpd promotes metastasis in vivo by supporting tumor invasion and intravasation. Lpd function in metastasis may be mediated via both ENa/VASP and the Scar/WAVE-complex because it was observed that Lpd mediates breast cancer invasion via both actin effectors. Both ENa/VASP and SCAR/WAVE are implicated in breast cancer metastasis by multiple lines of evidence. Results presented here suggest that the pro-metastatic function of Lpd may, in part, involve coordinating the activities of these two distinct types of actin regulators to optimize chemotactic invasion and matrix degradation by invading tumor cells.

The experimental results provide evidence that Lpd is a substrate of Src kinases and that phosphorylation of Lpd by Src positively regulates the Lpd-Scar/WAVE-complex interaction, but not the Lpd-ENa/VASP interaction, whereas c-Abl mediated phosphorylation of Lpd positively regulates both Lpd-ENa/VASP and Lpd-Scar/WAVE interaction. This differential regulation of Lpd-ENa/VASP or Lpd-Scar/WAVE recruitment may allow Lpd to fine-tune actin cytoskeletal dynamics via ENa/VASP-mediated actin filament elongation and Scar/WAVE-Arp2/3-mediated nucleation/branching. Lpd driven random 2D cell migration requires Scar/WAVE, but not ENa/VASP, Lpd-dependent chemosensing in 2D requires ENa/VASP, and interactions with both SCAR/WAVE and ENa/VASP are required for 3D chemotaxis and migration. These findings lead to the interesting possibility that Lpd balances actin nucleation/branching and filament elongation activities to optimize protrusion morphology and dynamics during cellular responses to growth factors and ECM composition and organization.

Surprisingly, it was observed from the experimental results that only moderately, but not highly increased levels of Lpd correlate with increased risk of breast cancer-associated mortality suggesting that not all of Lpd functions (cell invasion, cell proliferation and EGFR endocytosis) induced by high but not medium levels of Lpd may be beneficial for tumors cells. However, in agreement with its role in metastasis, it was found that highly increased Lpd abundance at the plasma membrane of cancer cells in breast tumors correlates with reduced disease- and metastasis-free interval. The increased membrane accumulation of Lpd protein observed in TMA analysis may reflect the role of Lpd in regulating membrane protrusion in migrating cells. Furthermore, consistent with the TMA analysis, it was found that increased Lpd mRNA levels correlate with reduced metastasis-free survival of breast cancer patients.

Based on these findings, it can be inferred that Lpd functions as an essential component of a pro-metastatic signaling pathway composed of Src and Abl kinases, Lpd, ENa/VASP, and Scar/WAVE that promotes metastatic progression.

INCORPORATION BY REFERENCE

The entire contents of all patents, published patent applications and other references cited herein are hereby expressly incorporated herein in their entireties by reference.

EQUIVALENTS

Those skilled in the art will recognize, or be able to ascertain using no more than routine experimentation, numerous equivalents to the specific procedures described herein. Such equivalents are considered to be within the scope of this invention and are covered by the following claims.

The invention claimed is:

1. A method for diagnosing and treating a metastatic breast cancer in a subject, the method comprising
obtaining a breast tissue sample from a subject;
detecting the amount or level of Lamellipodin (Lpd) protein in the sample with an anti-Lpd antibody or Lpd-binding polypeptide;
comparing the amount or level of Lpd protein from the sample to a control, wherein an increased amount of Lpd protein is indicative of a metastatic breast cancer or a breast cancer at risk of becoming metastatic;
diagnosing the subject with metastatic breast cancer or as being at risk of developing metastatic breast cancer when the amount of Lpd protein is enhanced as compared to the control; and
treating the subject having metastatic breast cancer or at risk of developing metastatic breast cancer with an effective amount of an anti-cancer therapeutic that includes at least one of: an Abl tyrosine kinase inhibitor; a Src tyrosine kinase inhibitor; a siRNA, shRNA, or a combination thereof that targets a Lpd encoding nucleic acid; or a combination thereof,
wherein the effective amount of an anti-cancer therapeutic is effective at treating, reducing or ameliorating a symptom of metastatic breast cancer, the progression of metastatic breast cancer, or both.

2. The method of claim 1, wherein the amount of Lpd protein is determined by detecting the amount of anti-Lpd antibody bound by surface plasmon resonance.

3. The method of claim 2, wherein, the antibody binds to an epitope encoded by the amino acid sequence of SEQ ID NO:2.

4. A method of treating a metastatic breast cancer in a patient, the method comprising:
administering an effective amount of an anti-cancer therapeutic to a patient having a breast tumor overexpressing Lpd protein,
wherein:
the anti-cancer therapeutic includes at least one of: an Abl tyrosine kinase inhibitor; a Src tyrosine kinase inhibitor; a siRNA, shRNA, or a combination thereof that targets a Lpd encoding nucleic acid; or a combination thereof; and
the effective amount of an anti-cancer therapeutic is effective at treating, reducing or ameliorating a symptom of metastatic breast cancer, the progression of metastatic breast cancer, or both.

5. The method of claim 1, wherein the breast tissue sample is a breast cancer tissue.

6. The method of claim 1, wherein the breast tissue sample is a metastatic breast cancer tissue.

7. A method for diagnosing and treating a metastatic breast cancer in a subject, the method comprising
obtaining a breast tissue sample from a subject;
detecting the amount or level of Lamellipodin (Lpd) gene expression in the sample with a labelled nucleic acid probe that is complementary to an Lpd encoding nucleic acid;
comparing the amount or level of Lpd gene expression from the sample to a control, wherein an increased amount of Lpd gene expression is indicative of a metastatic breast cancer or a breast cancer at risk of becoming metastatic;
diagnosing the subject with metastatic breast cancer or as being at risk of developing metastatic breast cancer when the amount of Lpd gene expression is enhanced as compared to the control; and
treating the subject having metastatic breast cancer or at risk of developing metastatic breast cancer with an effective amount of an anti-cancer therapeutic that includes at least one of: an Abl tyrosine kinase inhibitor; a Src tyrosine kinase inhibitor; a siRNA, shRNA, or a combination thereof that targets a Lpd encoding nucleic acid; or a combination thereof,
wherein the effective amount of an anti-cancer therapeutic is effective at treating, reducing or ameliorating a symptom of metastatic breast cancer, the progression of metastatic breast cancer, or both.

8. The method of claim 7, wherein the breast tissue sample is a breast cancer tissue.

9. The method of claim 7, wherein the breast tissue sample is a metastatic breast cancer tissue.

10. The method of claim 4, wherein the breast tumor is a metastatic breast cancer tissue.

11. The method of claim 1, wherein the therapeutic is selected from Imatinib, Nilotinib, or a combinations thereof.

* * * * *

SEQUENCE LISTING

```
<160> NUMBER OF SEQ ID NOS: 4

<210> SEQ ID NO 1
<211> LENGTH: 5372
<212> TYPE: DNA
<213> ORGANISM: Homo sapiens

<400> SEQUENCE: 1 cccgccccg  ctcccgccgc  cgcccgccag  tcagtcagtc  agtcagtcag  tcagtcagtc      60
agtcagtcag  tcactgagcg  cgcggcgcgg  gagctgctgg  cagtcgctgc  gtctctggcg     120
agggagcgcc  gcgcctgggg  aggaggcgga  ggcagcggct  ggaggagcgc  gagcggcggt     180
ttccttgccc  ggggccgcgg  gaaggccgac  cgactgccgc  gatggagcag  ctatcagatg     240
aagaaattga  tcatggtgct  gaagaagaca  gtgacaagga  agatcaggac  ctggacaaaa     300
tgtttggagc  ctggcttgga  gaactagaca  aactcactca  gagtttggat  tctgacaagc     360
ccatggaacc  agtaaaaaga  tctcctcttc  gccaggaaac  aaacatggcc  aacttttctt     420
accgcttctc  catatacaac  ttgaatgaag  ctctgaatca  gggagagact  gtggatctgg     480
atgccttgat  ggctgatctt  tgctctatag  agcaggagct  cagcagcatt  ggttcaggaa     540
acagtaagcg  tcaaatcaca  gaaacgaaag  ctactcagaa  attgcctgtt  agccgacata     600
cattgaaaca  tggcaccttg  aaaggattat  cttcttcatc  taataggata  gctaaacctt     660
cccatgccag  ctactccttg  gacgacgtca  ctgcacagtt  agaacaggcc  tctttgagta     720
tggatgaggc  tgctcagcaa  tctgtactag  aagatactaa  acccttagta  actaatcagc     780
acagaagaac  cgcgtcagca  ggcacagtga  gtgatgctga  agtacactct  attagtaatt     840
cctcccattc  cagcatcact  tccgcagcct  ccagcatgga  ctctttggat  attgataaag     900
taacacgccc  tcaagagctg  gatttgacac  atcaagggca  gccaattact  gaggaagaac     960
aggcagcaaa  attgaaagct  gagaagatca  gagttgccct  agagaaaatt  aaagaggcac    1020
aagtgaaaaa  gctggtgatc  agagtccaca  tgtctgatga  cagttctaaa  acaatgatgg    1080
tggatgagag  gcagacagta  agacaagtac  tggataacct  gatggacaaa  tcccactgcg    1140
gttatagttt  agactggtca  ctggtagaaa  ccgtttctga  attacaaatg  gagagaatct    1200
ttgaagacca  tgaaaacttg  gttgaaaatc  ttcttaattg  gacaagagat  agccaaaaca    1260
agcttatatt  tatggagcgt  atagaaaaat  atgcacttt  caaaaaccca  cagaattatc    1320
tttttgggaa  aaaggaaaca  gctgagatgg  cagatagaaa  caaagaagtc  ctcttggagg    1380 aatgttttg  tggaagttct  gtaactgtac  cagaaattga  aggagtcctt  tggttgaagg    1440
atgatggcaa  gaagtcctgg  aaaaagcgtt  attttctctt  gcgagcatct  ggtatctact    1500
atgttcccaa  aggaaaagca  aaggtctctc  gggatctggt  gtgctttctc  cagctggatc    1560
atgtcaacgt  ttattatggc  caggactatc  ggaacaaata  caaagcacct  acagactatt    1620
```

-continued

```
gtctggtgct gaagcatcca caaatccaga agaaatctca atatatcaaa tacctttgtt    1680
gtgatgatgt gaggacactg catcagtggg tcaatgggat ccgcattgca aagtatggga    1740
agcagctcta tatgaactac aagaagcct tgaagaggac agagtcagcc tatgattgga     1800
cttccttatc cagctccagc attaaatcgg gatccagttc ttccagcatc ccagagtctc    1860
agtcaaacca ctccaatcag tctgatagcg gagtttctga cacccagcca gcaggacacg    1920
tccgttccca gagcattgtg agctccgtat tctctgaagc ctggaaacga ggcactcagt    1980
tggaagagtc cagcaaggcc agaatggagt ctatgaatcg ccctacact tcacttgtgc     2040
cccctttatc cccgcaacct aagatagtca ccccctacac tgcttcacag ccttcaccac    2100
ctctacctcc tccgccaccc ccacctcctc ctccaccacc ccctccacca cccctcctc     2160
ccccactccc cagccagtct gcaccttctg caggctcagc agcccaatg ttcgtcaagt      2220
acagcacaat aacacggcta cagaatgcgt ctcagcattc aggggccctg tttaagccgc     2280
caacaccccc agtgatgcag tcacagtcag tgaagcctca gatcctggta cccccaatg      2340
gagttgttcc accacccct ccccctcctc cacccccaac cccaggctct gccatggccc      2400
agctaaagcc tgcaccgtgt gccccatccc ttccacagtt cagtgccccg cctcctccac    2460
tgaagatcca tcaagttcag catattactc aggtggctcc cccaacaccc ccccacctc     2520
ctcctatccc tgcaccccctc cctccccaag ctccccaaa acccttgtg accatccccg     2580
caccaaccag caccaagact gtggcacctg ttgtgactca agctgcacca cccacaccta    2640
ctcctccagt gcccccagca aaaaagcagc cagctttccc tgcttcttac attccaccct    2700
ctcccccta ccctcctgtt ccagtaccc cgccaacatt ccccaagcaa cagagcttct       2760
gtgcaaaacc ccctccctct ccactgtcac cggtgccctc ggtcgtgaag cagatagcca    2820
gccagtttcc acccctcca actccccctg ccatggaatc tcagccctta aagcctgtcc     2880
cagcaaatgt agctccacag tcccctcctg cagtaaaagc aaagcccaag tggcagccca    2940
gctccatccc agtcccttct ccggacttcc ctcctccccc tcctgaaagc agcctggtgt    3000
ttcctcctcc acccccatca cctgtcccag cccaccacc gccacctcca cccacagctt    3060
ctcctacccc tgacaaaagt ggatctccag gcaaaaagac cagtaagacg tccagccctg    3120
ggggaaagaa accaccccca accccacagc gcaactccag cattaaatcc agcagtggtg    3180
cagagcaccc cgagcccaag agaccctcgg tggacagtct agtcagcaag tttacaccgc    3240
cagcagaatc agggtctccc agcaaggaga ccctaccacc tcctgcagca cccccaagc     3300
ctggaaaact caatctttct ggagtcaacc ttcctggagt tctccaacaa gggtgtgtgt    3360
cagcaaaagc ccctgttctg agtgggcgtg gaaaggactc cgtggtggaa tttccttctc    3420
ctccatccga ttctgatttt ccacccccctc cacctgaaac agaccttcct ctgcccccca   3480
ttgagattcc agcagttttc tcgggaaaca cctctccaaa agtggcagtc gttaatcctc    3540
aaccacaaca atggtctaaa atgtcagtga agaaggcccc tccacccaca cgacccaaac    3600
ggaatgatag caccccgcctc actcaagctg agattctga gcagccaaca atggccacag    3660
ttgtgccaca agtgcccacc tctcccaaat ccagccttag tgtccagcct ggattcctgg    3720
ctgacctcaa caggacactg caacgaaagt ccatcactcg gcacggctca ctctcctccc    3780
gcatgtccag agcagaacca acagccacca tggatgatat ggcattgcct ccaccacccc    3840
ctgaactgct gtctgatcaa cagaaggctg gttacggagg cagtcatata tcaggctatg    3900
caacgttgcg gagaggaccc cctcctgctc cccccaaaag agaccagaac accaagctct    3960
ccagagactg gtagccacca taggacttta ttttcatgat atctgtaatc actgctacaa    4020
```

-continued

```
tcagctcacc tgatcatctg tgaattcagg tgttcagagc ctcctggtat gatgttattc    4080
aggtagtgtc cagctatatg tgtatgtgtg tgtgtacacg tgcatgtaca cacagctgta    4140
cagtgtgtgt atatatgtat acatatatgt atgtgtatgt gtatatagag agagagctga    4200
gagttattct atttattcct tttctctcct aatctgaaaa tgggtgttct gtattttggg    4260
tggaagaggc atagaagggg atgtgtgttg tctcttaaga tttctatatc atgtggattg    4320
gaccaaaaac ttctaatcac ttatttagaa ggtatttata agtgtctgtc catgtgtagc    4380
ctattcgtgc atgttgtgta ttatataact aaggaataga tgtagaatgt gctatttctg    4440
gttgagaaaa atcaccagaa tgtttggtgt atctataagg cttttgtgtt tgttttcccc    4500
cagttggctg aagttagaat tgcttgactg acacttcatt gctatacatg aagggcact    4560
ttaaatcagg aaaatctctc agcttcatag aacgggtaac tagtgcagga tggggaaatg    4620
ttcacagaca tcatctgtat gtggttgtgc atagaaagta aatacatggc gtaattaact    4680
cagctgttct agctgcagta ctgctgcagt gatccaccca catttaggat gtgctgacag    4740
ataagctctt tgcctacaat acatggataa ttagtgctat aattctggat agttcctttt    4800
tagtactgtt ttatgaagct ttatcaactt ggcttcatga tcctcacttt gattgattt    4860
aagaggatgg ataacacagt tatctctgta atgttctgtc ccagtatgtc tttgggtcac    4920
cagttacctt cttaaaatat gtgctttagg taggtgttat tacatatctg tagacaattg    4980
gtatatgaaa tatacacatc ctgtgcccca atatggtgca ttatgaaaaa caaaatcatt    5040
ttctaaaatg catttttga gcattgctct atagaaggga agggtgatga gagaacagaa    5100
ctggcccctg tacaggtgtc attaatctgg ttgtatatgg gttataatat gtaatacaaa    5160
aagctcatta agtatgggac tacatggaga gggaagacag tttcatttat agctactggg    5220
gctaccagga cccttgctga ctgcagcctg gttgtgatta gttcaggtta ctaggtgttc    5280
tgatggagtg ggacagtcca agtccagtaa ctgacattac gttttatgcg tgtgcagttt    5340
ggtataacgt ggagtcagtg ctctaacgac ac                                  5372
```

<210> SEQ ID NO 2
<211> LENGTH: 1250
<212> TYPE: PRT
<213> ORGANISM: Homo sapiens

<400> SEQUENCE: 2

```
Met Glu Gln Leu Ser Asp Glu Glu Ile Asp His Gly Ala Glu Glu Asp
1               5                   10                  15

Ser Asp Lys Glu Asp Gln Asp Leu Asp Lys Met Phe Gly Ala Trp Leu
            20                  25                  30

Gly Glu Leu Asp Lys Leu Thr Gln Ser Leu Asp Ser Asp Lys Pro Met
        35                  40                  45

Glu Pro Val Lys Arg Ser Pro Leu Arg Gln Glu Thr Asn Met Ala Asn
    50                  55                  60

Phe Ser Tyr Arg Phe Ser Ile Tyr Asn Leu Asn Glu Ala Leu Asn Gln
65                  70                  75                  80

Gly Glu Thr Val Asp Leu Asp Ala Leu Met Ala Asp Leu Cys Ser Ile
                85                  90                  95

Glu Gln Glu Leu Ser Ser Ile Gly Ser Gly Asn Ser Lys Arg Gln Ile
            100                 105                 110

Thr Glu Thr Lys Ala Thr Gln Lys Leu Pro Val Ser Arg His Thr Leu
        115                 120                 125
```

-continued

```
Lys His Gly Thr Leu Lys Gly Leu Ser Ser Ser Asn Arg Ile Ala
    130                 135                 140
Lys Pro Ser His Ala Ser Tyr Ser Leu Asp Asp Val Thr Ala Gln Leu
145                 150                 155                 160
Glu Gln Ala Ser Leu Ser Met Asp Glu Ala Ala Gln Gln Ser Val Leu
                165                 170                 175
Glu Asp Thr Lys Pro Leu Val Thr Asn Gln His Arg Arg Thr Ala Ser
            180                 185                 190
Ala Gly Thr Val Ser Asp Ala Glu Val His Ser Ile Ser Asn Ser Ser
        195                 200                 205
His Ser Ser Ile Thr Ser Ala Ala Ser Ser Met Asp Ser Leu Asp Ile
    210                 215                 220
Asp Lys Val Thr Arg Pro Gln Glu Leu Asp Leu Thr His Gln Gly Gln
225                 230                 235                 240
Pro Ile Thr Glu Glu Glu Gln Ala Ala Lys Leu Lys Ala Glu Lys Ile
                245                 250                 255
Arg Val Ala Leu Glu Lys Ile Lys Glu Ala Gln Val Lys Lys Leu Val
            260                 265                 270
Ile Arg Val His Met Ser Asp Asp Ser Ser Lys Thr Met Met Val Asp
        275                 280                 285
Glu Arg Gln Thr Val Arg Gln Val Leu Asp Asn Leu Met Asp Lys Ser
290                 295                 300
His Cys Gly Tyr Ser Leu Asp Trp Ser Leu Val Glu Thr Val Ser Glu
305                 310                 315                 320
Leu Gln Met Glu Arg Ile Phe Glu Asp His Glu Asn Leu Val Glu Asn
                325                 330                 335
Leu Leu Asn Trp Thr Arg Asp Ser Gln Asn Lys Leu Ile Phe Met Glu
            340                 345                 350
Arg Ile Glu Lys Tyr Ala Leu Phe Lys Asn Pro Gln Asn Tyr Leu Leu
        355                 360                 365
Gly Lys Lys Glu Thr Ala Glu Met Ala Asp Arg Asn Lys Glu Val Leu
    370                 375                 380
Leu Glu Glu Cys Phe Cys Gly Ser Ser Val Thr Val Pro Glu Ile Glu
385                 390                 395                 400
Gly Val Leu Trp Leu Lys Asp Asp Gly Lys Lys Ser Trp Lys Lys Arg
                405                 410                 415
Tyr Phe Leu Leu Arg Ala Ser Gly Ile Tyr Tyr Val Pro Lys Gly Lys
            420                 425                 430
Ala Lys Val Ser Arg Asp Leu Val Cys Phe Leu Gln Leu Asp His Val
        435                 440                 445
Asn Val Tyr Tyr Gly Gln Asp Tyr Arg Asn Lys Tyr Lys Ala Pro Thr
    450                 455                 460
Asp Tyr Cys Leu Val Leu Lys His Pro Gln Ile Gln Lys Lys Ser Gln
465                 470                 475                 480
Tyr Ile Lys Tyr Leu Cys Cys Asp Asp Val Arg Thr Leu His Gln Trp
                485                 490                 495
Val Asn Gly Ile Arg Ile Ala Lys Tyr Gly Lys Gln Leu Tyr Met Asn
            500                 505                 510
Tyr Gln Glu Ala Leu Lys Arg Thr Glu Ser Ala Tyr Asp Trp Thr Ser
        515                 520                 525
Leu Ser Ser Ser Ile Lys Ser Gly Ser Ser Ser Ser Ile Pro
    530                 535                 540
Glu Ser Gln Ser Asn His Ser Asn Gln Ser Asp Ser Gly Val Ser Asp
```

-continued

```
              545                 550                 555                 560
        Thr Gln Pro Ala Gly His Val Arg Ser Gln Ser Ile Val Ser Ser Val
                            565                 570                 575
        Phe Ser Glu Ala Trp Lys Arg Gly Thr Gln Leu Glu Glu Ser Ser Lys
                            580                 585                 590
        Ala Arg Met Glu Ser Met Asn Arg Pro Tyr Thr Ser Leu Val Pro Pro
                            595                 600                 605
        Leu Ser Pro Gln Pro Lys Ile Val Thr Pro Tyr Thr Ala Ser Gln Pro
                            610                 615                 620
        Ser Pro Pro Leu Pro Pro Pro Pro Pro Pro Pro Pro Pro Pro Pro Pro
        625                 630                 635                 640
        Pro Pro Pro Pro Pro Pro Leu Pro Ser Gln Ser Ala Pro Ser
                            645                 650                 655
        Ala Gly Ser Ala Ala Pro Met Phe Val Lys Tyr Ser Thr Ile Thr Arg
                            660                 665                 670
        Leu Gln Asn Ala Ser Gln His Ser Gly Ala Leu Phe Lys Pro Pro Thr
                            675                 680                 685
        Pro Pro Val Met Gln Ser Gln Ser Val Lys Pro Gln Ile Leu Val Pro
                            690                 695                 700
        Pro Asn Gly Val Val Pro Pro Pro Pro Pro Pro Pro Pro Pro Pro Thr
        705                 710                 715                 720
        Pro Gly Ser Ala Met Ala Gln Leu Lys Pro Ala Pro Cys Ala Pro Ser
                            725                 730                 735
        Leu Pro Gln Phe Ser Ala Pro Pro Pro Leu Lys Ile His Gln Val
                            740                 745                 750
        Gln His Ile Thr Gln Val Ala Pro Pro Thr Pro Pro Pro Pro Pro
                            755                 760                 765
        Ile Pro Ala Pro Leu Pro Pro Gln Ala Pro Pro Lys Pro Leu Val Thr
                            770                 775                 780
        Ile Pro Ala Pro Thr Ser Thr Lys Thr Val Ala Pro Val Val Thr Gln
        785                 790                 795                 800
        Ala Ala Pro Pro Thr Pro Thr Pro Pro Val Pro Pro Ala Lys Lys Gln
                            805                 810                 815
        Pro Ala Phe Pro Ala Ser Tyr Ile Pro Pro Ser Pro Thr Pro Pro
                            820                 825                 830
        Val Pro Val Pro Pro Pro Thr Leu Pro Lys Gln Gln Ser Phe Cys Ala
                            835                 840                 845
        Lys Pro Pro Pro Ser Pro Leu Ser Pro Val Pro Ser Val Val Lys Gln
                            850                 855                 860
        Ile Ala Ser Gln Phe Pro Pro Pro Thr Pro Pro Ala Met Glu Ser
        865                 870                 875                 880
        Gln Pro Leu Lys Pro Val Pro Ala Asn Val Ala Pro Gln Ser Pro Pro
                            885                 890                 895
        Ala Val Lys Ala Lys Pro Lys Trp Gln Pro Ser Ser Ile Pro Val Pro
                            900                 905                 910
        Ser Pro Asp Phe Pro Pro Pro Glu Ser Ser Leu Val Phe Pro
                            915                 920                 925
        Pro Pro Pro Pro Ser Pro Val Pro Ala Pro Pro Pro Pro Pro Pro
                            930                 935                 940
        Thr Ala Ser Pro Thr Pro Asp Lys Ser Gly Ser Pro Gly Lys Lys Thr
        945                 950                 955                 960
        Ser Lys Thr Ser Ser Pro Gly Gly Lys Lys Pro Pro Thr Pro Gln
                            965                 970                 975
```

```
Arg Asn Ser Ser Ile Lys Ser Ser Gly Ala Glu His Pro Glu Pro
            980                 985                 990

Lys Arg Pro Ser Val Asp Ser Leu Val Ser Lys Phe Thr Pro Pro Ala
        995                 1000                1005

Glu Ser Gly Ser Pro Ser Lys Glu Thr Leu Pro Pro Ala Ala
    1010                1015                1020

Pro Pro Lys Pro Gly Lys Leu Asn Leu Ser Gly Val Asn Leu Pro
    1025                1030                1035

Gly Val Leu Gln Gln Gly Cys Val Ser Ala Lys Ala Pro Val Leu
    1040                1045                1050

Ser Gly Arg Gly Lys Asp Ser Val Val Glu Phe Pro Ser Pro Pro
    1055                1060                1065

Ser Asp Ser Asp Phe Pro Pro Pro Pro Glu Thr Asp Leu Pro
    1070                1075                1080

Leu Pro Pro Ile Glu Ile Pro Ala Val Phe Ser Gly Asn Thr Ser
    1085                1090                1095

Pro Lys Val Ala Val Val Asn Pro Gln Pro Gln Gln Trp Ser Lys
    1100                1105                1110

Met Ser Val Lys Lys Ala Pro Pro Thr Arg Pro Lys Arg Asn
    1115                1120                1125

Asp Ser Thr Arg Leu Thr Gln Ala Glu Ile Ser Glu Gln Pro Thr
    1130                1135                1140

Met Ala Thr Val Val Pro Gln Val Pro Thr Ser Pro Lys Ser Ser
    1145                1150                1155

Leu Ser Val Gln Pro Gly Phe Leu Ala Asp Leu Asn Arg Thr Leu
    1160                1165                1170

Gln Arg Lys Ser Ile Thr His Gly Ser Leu Ser Ser Arg Met
    1175                1180                1185

Ser Arg Ala Glu Pro Thr Ala Thr Met Asp Asp Met Ala Leu Pro
    1190                1195                1200

Pro Pro Pro Pro Glu Leu Leu Ser Asp Gln Gln Lys Ala Gly Tyr
    1205                1210                1215

Gly Gly Ser His Ile Ser Gly Tyr Ala Thr Leu Arg Arg Gly Pro
    1220                1225                1230

Pro Pro Ala Pro Pro Lys Arg Asp Gln Asn Thr Lys Leu Ser Arg
    1235                1240                1245

Asp Trp
1250

<210> SEQ ID NO 3
<211> LENGTH: 2302
<212> TYPE: DNA
<213> ORGANISM: Homo sapiens

<400> SEQUENCE: 3
cggcggccgg gcgcgcggcc ccggcgggca cccctcaaag ggcggccgag gaagctccgg      60
gaggaggagc agggaccacg agggaggtgg gaggcggcgg ccgcctgggg accagctccg     120
cgcctcggcc tctccgcccc ctccccagcc tttctctcgc cctcttctcc cacactcccg     180
gccggcgcct cggctttgtg cgaggagatg gtgtagcccc ctggccgccg aaggaggagc     240
cggacacttg tctcccgtct ccgagctgct ccccaccccct ggaggagaga ccccccccctc    300 ggctcggcgc cttctgcgtc tcccggctgg tggggaagcc tctgcgccgc cggcaccatg     360
agtgaacaga gtatctgtca ggcaagagct gctgtgatgg tttatgatga tgccaataag    420
```

```
aagtgggtgc cagctggtgg ctcaactgga ttcagcagag ttcatatcta tcaccataca    480
ggcaacaaca cattcagagt ggtgggcagg aagattcagg accatcaggt cgtgataaac    540
tgtgccattc ctaaagggtt gaagtacaat caagctacac agaccttcca ccagtggcga    600
gatgctagac aggtgtatgg tctcaacttt ggcagcaaag gggatgccaa tgtcttcgca    660
agtgccatga tgcatgcctt agaagtgtta aattcacagg aaacagggcc aacattgcct    720
agacaaaact cacaactacc tgctcaagtt caaaatggcc catcccaaga gaattggaa     780 attcaaagaa gacaactaca gaacagcaa cggcaaaagg agctggagcg ggaaaggctg     840
gagcgagaaa gaatggaaag agaaaggttg gagagagaga ggttagaaag ggaaaggctg    900
gagagggagc gactggaaca gaacagctg gagagagaga gacaagaacg ggaacggcag     960
gaacgcctgg agcggcagga acgcctggag cggcaggaac gcctgagcg gcaggaacgc   1020 ctggatcggg agaggcaaga aagacaagaa cgagagaggc tggagagact ggaacgggag   1080
aggcaagaaa gggagcgaca gagcagtta gaaagggaac agctggaatg ggagagagag   1140
cgcagaatat caagtgctgc tgcccctgcc tctgttgaga ctcctctaaa ctctgtgctg    1200
ggagactctt ctgcttctga gccaggcttg caggcagcct ctcagccggc cgagactcca    1260
tcccaacagg gcattgtctt gggaccactt gcacctccac ctcctccacc actcccacca    1320
gggcctgcac aggcttcagt agccctccct cctcccccag ggcccctcc acctcctcca    1380 ctcccatcca ccgggcctcc accgccccct cctcccctc tctccctaa tcaagtaccc    1440 cctcctcctc caccacctcc tgccccaccc ctccctgcat ctggattctt tttggcatcc    1500
atgtcagaag acaatcgccc tttaactgga cttgcagctg caattgccgg agcaaaactt    1560
aggaaagtgt cacggatgga ggatacctct ttcccaagtg gagggaatgc tattggtgtg    1620
aactccgcct catctaaaac agatacaggc cgtggaaatg gaccccttcc tttagggggt    1680
agtggtttaa tggaagaaat gagtgccctg ctggccagga ggagaagaat tgctgaaaag    1740
ggatcaacaa tagaaacaga acaaaaagag gacaaaggtg aagattcaga gcctgtaact    1800
tctaaggcct cttcaacaag tacacctgaa ccaacaagaa aaccttggga agaacaaat    1860 acaatgaatg gcagcaagtc acctgttatc tccagaccaa aatccacacc ttatcacag    1920 cccagtgcca atggagtcca gacggaagga cttgactatg acaggctgaa gcaggacatt   1980
ttagatgaaa tgagaaaaga attaacaaag ctaaagaag agctcattga tgcaatcagg    2040
caggaactga gcaagtcaaa tactgcatag aggaacagac taaggagaga taggacttta    2100
atctggagga aaaatatcct acaaacaaca actgttcaca acagcaaacc cctacattta    2160
tgagctgtaa gaagaaaatg gagacaaaca gaaggaggga aaaaccaacc tactctgaaa    2220
gccttcagac attatgactc tggtgataag ctctttccct ctccgtttgc tgctttttc    2280 tggcctttac aacagaatgg aa                                            2302
```

<210> SEQ ID NO 4
<211> LENGTH: 570
<212> TYPE: PRT
<213> ORGANISM: Homo sapiens

<400> SEQUENCE: 4

```
Met Ser Glu Gln Ser Ile Cys Gln Ala Arg Ala Ala Val Met Val Tyr
1               5                   10                  15

Asp Asp Ala Asn Lys Lys Trp Val Pro Ala Gly Gly Ser Thr Gly Phe
            20                  25                  30
```

-continued

```
Ser Arg Val His Ile Tyr His His Thr Gly Asn Asn Thr Phe Arg Val
         35                  40                  45
Val Gly Arg Lys Ile Gln Asp His Gln Val Val Ile Asn Cys Ala Ile
 50                  55                  60
Pro Lys Gly Leu Lys Tyr Asn Gln Ala Thr Gln Thr Phe His Gln Trp
 65                  70                  75                  80
Arg Asp Ala Arg Gln Val Tyr Gly Leu Asn Phe Gly Ser Lys Glu Asp
                 85                  90                  95
Ala Asn Val Phe Ala Ser Ala Met Met His Ala Leu Glu Val Leu Asn
                100                 105                 110
Ser Gln Glu Thr Gly Pro Thr Leu Pro Arg Gln Asn Ser Gln Leu Pro
        115                 120                 125
Ala Gln Val Gln Asn Gly Pro Ser Gln Glu Glu Leu Glu Ile Gln Arg
130                 135                 140
Arg Gln Leu Gln Glu Gln Gln Arg Gln Lys Glu Leu Glu Arg Glu Arg
145                 150                 155                 160
Leu Glu Arg Glu Arg Met Glu Arg Glu Arg Leu Glu Arg Glu Arg Leu
                165                 170                 175
Glu Arg Glu Arg Leu Glu Arg Glu Arg Leu Glu Gln Glu Gln Leu Glu
        180                 185                 190
Arg Glu Arg Gln Glu Arg Glu Arg Gln Glu Arg Leu Glu Arg Gln Glu
        195                 200                 205
Arg Leu Glu Arg Gln Glu Arg Leu Glu Arg Gln Glu Arg Leu Asp Arg
        210                 215                 220
Glu Arg Gln Glu Arg Gln Glu Arg Glu Arg Leu Glu Arg Glu Leu Arg
225                 230                 235                 240
Glu Arg Gln Glu Arg Glu Arg Gln Glu Gln Leu Glu Arg Glu Gln Leu
                245                 250                 255
Glu Trp Glu Arg Glu Arg Arg Ile Ser Ser Ala Ala Ala Pro Ala Ser
                260                 265                 270
Val Glu Thr Pro Leu Asn Ser Val Leu Gly Asp Ser Ser Ala Ser Glu
        275                 280                 285
Pro Gly Leu Gln Ala Ala Ser Gln Pro Ala Glu Thr Pro Ser Gln Gln
        290                 295                 300
Gly Ile Val Leu Gly Pro Leu Ala Pro Pro Pro Pro Pro Pro Leu Pro
305                 310                 315                 320
Pro Gly Pro Ala Gln Ala Ser Val Ala Leu Pro Pro Pro Pro Gly Pro
                325                 330                 335
Pro Pro Pro Pro Pro Leu Pro Ser Thr Gly Pro Pro Pro Pro Pro Pro
        340                 345                 350
Pro Pro Pro Leu Pro Asn Gln Val Pro Pro Pro Pro Pro Pro Pro Pro
        355                 360                 365
Ala Pro Pro Leu Pro Ala Ser Gly Phe Phe Leu Ala Ser Met Ser Glu
        370                 375                 380
Asp Asn Arg Pro Leu Thr Gly Leu Ala Ala Ile Ala Gly Ala Lys
385                 390                 395                 400
Leu Arg Lys Val Ser Arg Met Glu Asp Thr Ser Phe Pro Ser Gly Gly
                405                 410                 415
Asn Ala Ile Gly Val Asn Ser Ala Ser Ser Lys Thr Asp Thr Gly Arg
                420                 425                 430
Gly Asn Gly Pro Leu Pro Leu Gly Gly Ser Gly Leu Met Glu Glu Met
        435                 440                 445
Ser Ala Leu Leu Ala Arg Arg Arg Arg Ile Ala Glu Lys Gly Ser Thr
```

-continued

```
            450                 455                 460
Ile Glu Thr Glu Gln Lys Glu Asp Lys Gly Glu Asp Ser Glu Pro Val
465                 470                 475                 480

Thr Ser Lys Ala Ser Ser Thr Ser Thr Pro Glu Pro Thr Arg Lys Pro
                485                 490                 495

Trp Glu Arg Thr Asn Thr Met Asn Gly Ser Lys Ser Pro Val Ile Ser
                500                 505                 510

Arg Pro Lys Ser Thr Pro Leu Ser Gln Pro Ser Ala Asn Gly Val Gln
            515                 520                 525

Thr Glu Gly Leu Asp Tyr Asp Arg Leu Lys Gln Asp Ile Leu Asp Glu
            530                 535                 540

Met Arg Lys Glu Leu Thr Lys Leu Lys Glu Glu Leu Ile Asp Ala Ile
545                 550                 555                 560

Arg Gln Glu Leu Ser Lys Ser Asn Thr Ala
                565                 570
```